United States Patent
Shiraishi et al.

(10) Patent No.: US 9,051,339 B2
(45) Date of Patent: Jun. 9, 2015

(54) SULFUR-CONTAINING BICYCLIC COMPOUND

(71) Applicant: Astellas Pharma Inc., Chuo-ku (JP)

(72) Inventors: Nobuyuki Shiraishi, Tokyo (JP); Hiroaki Hoshii, Tokyo (JP); Wataru Hamaguchi, Tokyo (JP); Eriko Honjo, Tokyo (JP); Tomofumi Takuwa, Tokyo (JP); Yuji Kondo, Tokyo (JP); Takayuki Goto, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 14/517,229

(22) Filed: Oct. 17, 2014

(65) Prior Publication Data

US 2015/0111876 A1  Apr. 23, 2015

(30) Foreign Application Priority Data

Oct. 17, 2013  (JP) ................................. 2013-216332

(51) Int. Cl.
| | | |
|---|---|---|
| *C07D 495/04* | (2006.01) | |
| *A61K 31/519* | (2006.01) | |
| *C07D 495/10* | (2006.01) | |
| *C07D 495/08* | (2006.01) | |
| *C07D 513/04* | (2006.01) | |

(52) U.S. Cl.
CPC ............ *C07D 513/04* (2013.01); *C07D 495/04* (2013.01); *C07D 495/10* (2013.01); *C07D 495/08* (2013.01)

(58) Field of Classification Search
CPC ............................ C07D 495/04; A61K 31/519
USPC ......................................... 544/278; 514/260.1
See application file for complete search history.

(56) References Cited

FOREIGN PATENT DOCUMENTS

| JP | 2001-097979 A | 4/2001 |
|---|---|---|
| WO | WO/02/062803 A1 | 8/2002 |
| WO | WO/2004/089312 A2 | 10/2004 |
| WO | WO/2006/008503 A1 | 1/2006 |
| WO | WO/2006/030031 A1 | 3/2006 |
| WO | WO2007/127175 A2 | 11/2007 |
| WO | WO2010/103130 A2 | 9/2010 |
| WO | WO2011/029054 A1 | 3/2011 |
| WO | WO2012/035423 A1 | 3/2012 |

OTHER PUBLICATIONS

Sarah M. Trattnig, et al., The Journal of Biological Chemistry vol. 287, No. 30, pp. 25241-25254, Jul. 20, 2012 © 2012 by The American Society for Biochemistry and Molecular Biology, Inc., Published in the U.S.A. "Discovery of a Novel Allosteric Modulator of 5-HT$_3$ Receptors Inhibition and Potentiation of Cysloop Receptor Signaling Through a Conserved Transmembrane Intersubunit Site".
Form PCT/ISA/210 issued in corresponding PCT/JP2014/077653, dated Oct. 17, 2014, 5 pp.
Form PCT/ISA/237 issued in corresponding PCT/JP2014/077653 with partial English translation, dated Oct. 17, 2014, 7 pp.

*Primary Examiner* — Susanna Moore
(74) *Attorney, Agent, or Firm* — Oblon, McClelland, Maier & Neustadt, L.L.P.

(57) ABSTRACT

A sulfur-containing bicyclic compound having a PAM action of GABA$_B$, and it use for preventing and/or treating schizophrenia, CIAS, cognitive impairment, fragile X syndrome, autism spectrum disorder, spasticity, anxiety disorder, substance addiction, pain, fibromyalgia, or Charcot-Marie-Tooth disease. A pharmaceutical composition for preventing and/or treating schizophrenia, cognitive impairment associated with schizophrenia (CIAS), cognitive impairment, fragile X syndrome, autism spectrum disorder, spasticity, anxiety disorder, substance addiction, pain, fibromyalgia, Charcot-Marie-Tooth disease, or the like, which has a positive allosteric modulator (PAM action) of GABA$_B$.

14 Claims, No Drawings

SULFUR-CONTAINING BICYCLIC COMPOUND

TECHNICAL FIELD

The present invention relates to a sulfur-containing bicyclic compound which is useful as an active ingredient for a pharmaceutical composition, in particular, a pharmaceutical composition for treating schizophrenia, cognitive impairment associated with schizophrenia (CIAS), cognitive impairment, fragile X syndrome, autism spectrum disorder, spasticity, anxiety disorder, substance addiction, pain, fibromyalgia, Charcot-Marie-Tooth disease, or the like.

BACKGROUND ART

γ-Aminobutyric acid (GABA) is a typical inhibitory neurotransmitter which activates both an ionotropic $GABA_A$ and a metabotropic $GABA_B$ receptor. The $GABA_B$ receptor is expressed in most of both presynaptic terminals and postsynaptic portions in the mammalian brain and adjusts the inhibitory synaptic transmission, and it thus has a wide range of physiological and psychopathological actions. The $GABA_B$ receptor is a G protein coupled receptor (GPCR), has a seven-transmembrane domain, and is structurally classified to a Class C. This Class C GPCRs have a particularly large extracellular region and functions by forming a homo- or heterodimer(s) (Neuropharmacology, 2011, January, vol. 60 (1), p. 82-92). The $GABA_B$ receptor forms a hetero-dimer of $GABA_{B1}$ and $GABA_{B2}$, and exerts a function as a receptor by the cooperation between the subunits. That is, only the $GABA_{B1}$ has a function for allowing a ligand of an orthosteric $GABA_B$ receptor to bind, and promotes the coupling and activating function of a G protein of $GABA_{B2}$. The activated $GABA_B$ receptor inhibits an adenylate cyclase and controls the openings of $K^+$ channels (GIRK) conjugated with G protein and voltage-dependent calcium channels.

From the recent studies, there have been reports that mental disorders such as a cognitive impairment and the like are caused by dysfunction of GABA-mediated nerves in a patient (Trends in Neurosciences, 2012, vol. 35 (1), p. 57-67; Molecular Psychiatry, 2003, vol. 8 (8), p. 721-737, 715; Frontiers in Psychiatry, 2012, vol. 3, p. 51; and Neuroscience & Biobehavioral Reviews, 2012, October, vol. 36 (9), p. 2044-2055).

Baclofen is a $GABA_B$ receptor-selective agonist and is clinically used. In preclinical trials, it has been reported that baclofen improves methanephetamine-induced cognitive impairment in mice (European Journal of Pharmacology, 2009, vol. 602 (1), p. 101-104); methanephetamine- and MK-801-induced prepulse inhibition disorder (Neuropsychopharmacology, 2008, December, vol. 33 (13), p. 3164-3175); and social behavioral disorder, spatial memory disorder, and γ-band brain waves in genetically modified mice with NMDA receptor hypofunction (Translational Psychiatry, 2012, Jul. 17, vol. 2, p. e142).

It has been reported that R-baclofen is effective in a fragile X syndrome patient and an autism spectrum disorder (Science Translational Medicine, 2012, Sep. 19, vol. 4 (152), p. 152ra127; and Journal of Autism and Development Disorders., 2014, April, vol. 44 (4), p. 958-964). It has also been reported that FMR1, a gene causing a fragile X syndrome, has a significant effect on the expression of numerous genes associated in an autism spectrum disorder (Nature, 2012, December, vol. 492, p. 382-386; and Cell, 2011, July, vol. 146 (2), p. 247-261).

Baclofen has been clinically used for the treatment of spasticity, contracture, or rigidity, which is caused from spinocerebellar degeneration, spinal cord injury, multiple sclerosis, amyotrophic lateral sclerosis, cerebral palsy, stroke, head trauma, or the like (Neurology, 2004, Oct. 26, vol. 63 (8), p. 1357-1363). It has also been reported that baclofen is effective in anxiety disorder (Journal of Pharmacology and Experimental Therapeutics, 2004, vol. 310, P. 952-963); substance addiction, for example, addiction to drugs such as nicotine, cocaine, morphine, and the like, or alcoholism (Advances in Pharmacology, 2010, vol. 58, p. 373-396; Drug and Alcohol Dependence, 2002, Feb. 1, vol. 65 (3), p. 209-220; and Synapse, 2003, October, vol. 50 (1), p. 1-6); pain, for example, neuropathic pain (European Journal of Pain, 2004, August, vol. 8(4), p. 377-383); and reflux esophagitis (Neurogastroenterology and Motility, 2012, June, vol. 24 (6), p. 553-559, e253).

There is a report that γ-hydroxybutyric acid (GHB), a $GABA_B$ agonist, also improves the fatigue in fibromyalgia patients and is thus effective for fibromyalgia (Pain, 2011, vol. 152, p. 1007-1017). The symptom of fibromyalgia is similar to that of a chronic fatigue syndrome. The $GABA_B$ agonist is expected to be effective for the chronic fatigue syndrome.

It has been reported that when $GABA_B$ signals are activated, the overexpression of PMP22 genes causing Charcot-Marie-Tooth disease type 1A is inhibited (European Journal of Neuroscience, 2004, May, vol. 19(10), p. 2641-2649; and Nature Reviews Drug Discovery, 2012, vol. 11, p. 589).

It has been reported that a $GABA_B$ receptor is also present in the peripheral organs, such as spleen, lung, liver, intestine, stomach, esophagus, bladder, and the like (Neuroscience, 2000, vol. 100 (1), p. 155-170; and The Journal of Biological Chemistry, 2000, Oct. 13, vol. 275 (41), p. 32174-32181). Therefore, the $GABA_B$ receptor ligand is expected to be applied in the treatment of diseases in the peripheral organs.

Thus, it is believed that a compound activating a $GABA_B$ receptor is useful for the prevention or treatment of schizophrenia, CIAS, cognitive impairment, fragile X syndrome, autism spectrum disorder, spasticity, anxiety disorder, substance addiction, pain, fibromyalgia, Charcot-Marie-Tooth disease, or the like.

On the other hand, baclofen has a narrow therapeutic window due to adverse side effects such as sedation, muscle weakness, and the like, and thus, its use is limited. A decrease in motor coordination, a decrease in a body temperature, and the like are also the side effects in baclofen therapy.

A plurality of reports on a positive allosteric modulator (PAM) exist (Molecular Pharmacology, 2001, vol. 60 (5), p. 963-971; Journal of Pharmacology and Experimental Therapeutics, 2004, September, vol. 310 (3), p. 952-963; and Psychopharmacology (Berl), 2011, May, vol. 215(1), p. 117-128). The PAM of the $GABA_B$ receptor binds to a receptor at a site different from a site for binding to an endogenous ligand, thereby improving the function of the receptor. The PAM of the $GABA_B$ receptor does not exhibit an agonistic activity alone, but increases the affinity to a receptor of an endogenous GABA, and thus, it has an action to increase the Potency and Efficacy of the $GABA_B$ receptor. It is believed that due to these properties, the PAM of the $GABA_B$ receptor does not exhibit the side effects of the $GABA_B$ agonist (for example, the side effects of baclofen as described above) and has useful therapeutic effects.

Therefore, the PAM of the $GABA_B$ receptor has little side effects and is expected to be useful for the prevention or treatment of schizophrenia, CIAS, cognitive impairment, fragile X syndrome, autism spectrum disorder, spasticity, anxiety disorder, substance addiction, pain, fibromyalgia, Charcot-Marie-Tooth disease, or the like.

Patent Document 1 discloses a compound of the following general formula, which includes a compound represented by Ex60 as a drug for treating schizophrenia.

[Chem. 1]

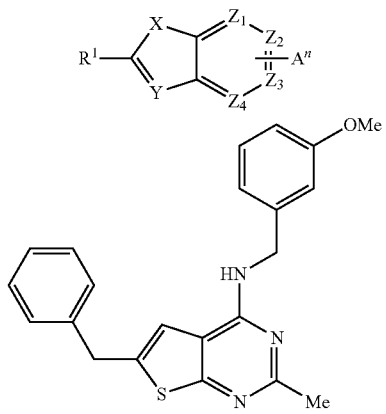

(In the formula, definition of $R^1$ includes many groups. As one of those groups, $R^1$ is a cycloalkyl group which may be substituted, or the like. Definition of $A''$ includes many groups. As one of those groups, $A''$ is an alkyl group which may be substituted, or the like. For the other symbols in the formula, refer to Patent Document 1.)

Patent Document 2 discloses that an mGluR1 inhibitor represented by the following general formula is useful for Parkinson's disease, migraine, or the like.

[Chem. 2]

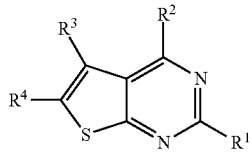

(In the formula, $R^2$ represents —$N(R^{2a})R^{2b}$, —O—$R^{2a}$, or —S—$R^{2a}$. For the other symbols in the formula, refer to Patent Document 2.)

Patent Document 3 discloses that a 5-HT antagonist represented by the following general formula is useful as a drug for treating for a neuropathological disease.

[Chem. 3]

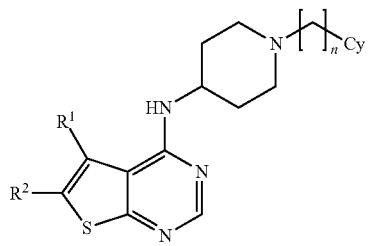

(For the symbols in the formula, refer to Patent Document 3.)

RELATED ART

Patent Document

[Patent Document 1] International Publication WO 2006/030031
[Patent Document 2] International Publication WO 02/062803 [Patent Document 3] International Publication WO 2004/089312

DISCLOSURE OF INVENTION

Problems to be Solved by the Invention

The present invention provides a sulfur-containing bicyclic compound which is useful as an active ingredient for a pharmaceutical composition, in particular, a pharmaceutical composition for treating schizophrenia, CIAS, cognitive impairment, fragile X syndrome, autism spectrum disorder, spasticity, anxiety disorder, substance addiction, pain, fibromyalgia, Charcot-Marie-Tooth disease, or the like.

Means for Solving the Problems

The present inventors have conducted extensive studies on PAM of a $GABA_B$ receptor, and as a result, they have found that a sulfur-containing bicyclic compound is the PANM of the $GABA_B$ receptor, thereby completing the present invention.

That is, the present invention relates to a compound of the formula (I) or a salt thereof, as well as a pharmaceutical composition comprising a compound of the formula (I) or a salt thereof and an excipient.

[Chem. 4]

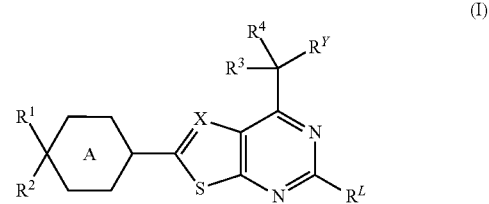

(in the formula,
X is CH,
$R^1$ is lower alkyl,
$R^2$ is lower alkyl,
in which $R^1$ and $R^2$ may form a cycloalkane together with carbon atoms to which they are bonded,
$R^3$ is —H,
$R^4$ is —H,
A ring is a cyclohexane ring,
$R^Y$ is —$NR^AR^B$,
$R^A$ and $R^B$ form cyclic amino which may be substituted, together with a nitrogen atom to which they are bonded,
in which the cyclic amino is a group represented by the following formula (III):

[Chem. 5]

Y is NH, O, S, S(=O)$_2$, or CH$_2$, and

R$^L$ is lower alkyl).

In addition, unless otherwise specified, when symbols in a certain chemical formula in the present specification are also used in another chemical formula, the same symbol represents the same meaning.

Further, the present invention relates to:

(1) a pharmaceutical composition for preventing or treating schizophrenia, CIAS, cognitive impairment, fragile X syndrome, autism spectrum disorder, spasticity, anxiety disorder, substance addiction, pain, fibromyalgia, or Charcot-Marie-Tooth disease, comprising a compound of the formula (I) or a salt thereof; where the pharmaceutical composition includes an agent for treating schizophrenia, CIAS, cognitive impairment, fragile X syndrome, autism spectrum disorder, spasticity, anxiety disorder, substance addiction, pain, fibromyalgia, or Charcot-Marie-Tooth disease, comprising a compound of the formula (I) or a salt thereof;

(2) use of a compound of the formula (I) or a salt thereof for the preparation of a pharmaceutical composition for preventing or treating schizophrenia, CIAS, cognitive impairment, fragile X syndrome, autism spectrum disorder, spasticity, anxiety disorder, substance addiction, pain, fibromyalgia, or Charcot-Marie-Tooth disease;

(3) use of a compound of the formula (I) or a salt thereof for preventing or treating schizophrenia, CIAS, cognitive impairment, fragile X syndrome, autism spectrum disorder, spasticity, anxiety disorder, substance addiction, pain, fibromyalgia, or Charcot-Marie-Tooth disease;

(4) a compound of the formula (I) or a salt thereof for preventing or treating schizophrenia, CIAS, cognitive impairment, fragile X syndrome, autism spectrum disorder, spasticity, anxiety disorder, substance addiction, pain, fibromyalgia, or Charcot-Marie-Tooth disease;

(5) a method for preventing or treating schizophrenia, CIAS, cognitive impairment, fragile X syndrome, autism spectrum disorder, spasticity, anxiety disorder, substance addiction, pain, fibromyalgia, or Charcot-Marie-Tooth disease, comprising administering to a subject an effective amount of a compound of the formula (I) or a salt thereof.

Meanwhile, the term "subject" is a human being or another animal in need of prevention or treatment thereof, and according to a certain embodiment, a human being in need of prevention or treatment thereof.

Effects of the Invention

The compound of the formula (I) or a salt thereof has a PAM action of a GABA$_B$ receptor, and can be used as an agent for preventing and/or treating schizophrenia, CIAS, cognitive impairment, fragile X syndrome, autism spectrum disorder, spasticity, anxiety disorder, substance addiction, pain, fibromyalgia, Charcot-Marie-Tooth disease, or the like.

EMBODIMENTS FOR CARRYING OUT THE INVENTION

Hereinafter, the present invention will be described in detail.

The "lower alkyl" is straight or branched chain alkyl having 1 to 6 carbon atoms (hereinafter simply referred to as C$_{1-6}$), for example, methyl, ethyl, n-propyl, isopropyl, n-butyl, isobutyl, sec-butyl, tert-butyl, n-pentyl, n-hexyl, or the like, in another embodiment, C$_{1-4}$ alkyl, and in a further embodiment, methyl.

The "lower alkylene" is straight or branched C$_{1-6}$ alkylene, for example, methylene, ethylene, trimethylene, tetramethylene, pentamethylene, hexamethylene, methylmethylene, ethylethylene, 1,2-dimethylethylene, 1,1,2,2-tetramethylethylene, or the like, in another embodiment, C$_{1-4}$ alkylene, and in a further embodiment, ethylene.

The "halo-lower alkyl" is C$_{1-6}$ alkyl substituted with one or more halogen atoms, in another embodiment, lower alkyl substituted with 1 to 5 halogen atoms, in a further embodiment, lower alkyl substituted with 1 to 3 halogen atoms, and in a still further embodiment, —CF$_3$.

The "halogen" means F, Cl, Br, or I.

The "cycloalkane" is a C$_{3-8}$ saturated hydrocarbon ring, for example, cyclopropane, cyclobutane, cyclopentane, cyclohexane, cycloheptane, or cyclooctane, in another embodiment, C$_{5-6}$ cycloalkane, in a further embodiment, cyclohexane, and in a still further embodiment, cyclopropane.

The "cycloalkyl" is a C$_{3-8}$ saturated hydrocarbon ring group, for example, cyclopropyl, cyclobutyl, cyclopentyl, cyclohexyl, cycloheptyl, or cyclooctyl, in another embodiment, C$_{5-6}$ cycloalkyl, in a further embodiment, cyclohexyl, and in a still further embodiment, cyclopropyl.

In the present specification, the expression "which may be substituted" means "which is not substituted" or "which is substituted with 1 to 5 substituents", and in another embodiment, "which is not substituted" or "which is substituted with 1 to 3 substituents". Further, if it has a plurality of substituents, the substituents may be the same as or different from each other.

In the present specification, with respect to the expression "R$^A$ and R$^B$ form cyclic amino which may be substituted, together with a nitrogen atom to which they are bonded", examples of the substituent which may be used for substitution in cyclic amino include the groups selected from the following Group Z.

Group Z:

(1) =O, (2) —OH, (3) —O-lower alkyl, (4) halogen, (5) —CN, (6) lower alkyl, (7) halo-lower alkyl, (8) lower alkylene-OH, (9) lower alkylene-O-lower alkyl,

(10) —C(=O)-lower alkyl,

(11) —C(=O)-lower alkylene-OH,

(12) —C(=O)-lower alkylene-CN, and

(13) cycloalkyl.

In a certain aspect, examples of the "group selected from the Group Z" include the groups selected from the following Group Z1.

Group Z1:

(1) —OH, (2) lower alkyl, and (3) —C(=O)-lower alkylene-OH.

Certain aspects of the present invention are shown below.

[1] A compound represented by the formula (I) or a salt thereof, in which

R$^Y$ is —NR$^A$R$^B$,

R$^A$ and R$^B$ form cyclic amino which may be substituted with R$^0$, together with a nitrogen atom to which they are bonded, in which the cyclic amino is a group represented by the following formula (III):

[Chem. 6]

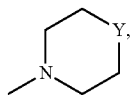

(III)

and

R⁰ is a group selected from the following Group Z:
Group Z:
(1) =O,
(2) —OH,
(3) —O-lower alkyl,
(4) halogen,
(5) —CN,
(6) lower alkyl,
(7) halo-lower alkyl,
(8) lower alkylene-OH,
(9) lower alkylene-O-lower alkyl,
(10) —C(=O)-lower alkyl,
(11) —C(=O)-lower alkylene-OH,
(12) —C(=O)-lower alkylene-CN, and
(13) cycloalkyl.

[2] The compound or a salt thereof as described in [1], in which the group selected from the Group Z is a group selected from:
Group Z1:
(1) —OH,
(2) lower alkyl, and
(3) —C(=O)-lower alkylene-OH.

[3] The compound of the formula (I) or a salt thereof, in which Y is O, S, or S(=O)₂.

[4] The compound of the formula (I) or a salt thereof, in which $R^L$ is CH₃.

[5] The compound or a salt thereof, which is a combination of two or more groups of the groups described in the embodiments [1] to [4].

Examples of the combination of the present invention are shown below.

[6] The compound of the formula (I) or a salt thereof, in which X is CH, Ring A is a cyclohexane ring, $R^1$ is lower alkyl, $R^2$ is lower alkyl, $R^3$ is —H, $R^4$ is —H, $R^Y$ is represented by the following formula (III) which may be substituted:

[Chem. 7]

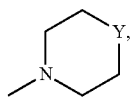

(III)

Y is O, S, or S(=O)₂, and $R^L$ is lower alkyl.

Examples of the specific compounds included in the present invention include the following compounds or salts thereof:

6-(4,4-dimethylcyclohexyl)-4-[(1,1-dioxo-1λ⁶-thiomorpholin-4-yl)methyl]-2-methylthieno[2,3-d]pyrimidine,
trans-1-{[6-(4,4-dimethylcyclohexyl)-2-methylthieno[2,3-d]pyrimidin-4-yl]methyl}piperidine-3,4-diol,
1-{[6-(4,4-dimethylcyclohexyl)-2-methylthieno[2,3-d]pyrimidin-4-yl]methyl}piperidin-4-ol,
6-(4,4-dimethylcyclohexyl)-2-methyl-4-(thiomorpholin-4-ylmethyl)thieno[2,3-d]pyrimidine,
6-(4,4-dimethylcyclohexyl)-4-[(3,3-dimethylmorpholin-4-yl)methyl]-2-methylthieno[2,3-d]pyrimidine, or
1-{[6-(4,4-dimethylcyclohexyl)-2-methylthieno[2,3-d]pyrimidin-4-yl]methyl}-2,2-dimethylpiperidin-4-ol.

The group "1,1-dioxo-1λ⁶-thiomorpholin-4-yl" means the same group as "1,1-dioxidothiomorpholin-4-yl".

In the present specification, the "PAM" is a compound that binds to a receptor at a site different from a site for binding to an endogenous ligand, thereby improving the function of the receptor. The compound does not exhibit an agonistic activity alone, but has an action to increase the Potency and Efficacy of the receptor.

In the present specification, the "PAM action" is an action which the PAM as described above has. For example, in Test Example 1, it means a compound that left-shifts or up-shifts a GABA dose-response reaction curve having a horizontal axis as a dose and a vertical axis as a response. When a test drug has the "Potency", the compound left-shifts the GABA dose-response curve leftwards, whereas when a test drug has "Efficacy", the compound up-shits GABA dose-response curve.

In the present specification, the symptoms of disease are not completely independent and may overlap each other. For example, the symptoms of schizophrenia, CIAS, and cognitive impairment may overlap each other.

Further, in the present specification, the name of disease is based on the references of "ICD10", which is the International Classification of Diseases of WHO (World Health Organization), 4th edition (DSM-4) and 5th edition (DSM-5) Statistical Manual of Mental Diagnosis in American Psychiatric Association (APA), and/or Guidelines of the Japanese Society of Neurology guidelines, or the like.

The compound of the formula (I) may exist in the form of tautomers or geometrical isomers depending on the kind of substituents. In the present specification, the compound of the formula (I) may be described in only one form of isomer, yet the present invention includes such an isomer, isolated forms of the isomers, or a mixture thereof.

In addition, the compound of the formula (I) may have asymmetric carbon atoms or axial asymmetry in some cases, and correspondingly, it may exist in the form of optical isomers. The present invention includes an isolated form of the optical isomers of the compound of the formula (I) or a mixture thereof.

Moreover, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Progress in Medicine, 1985, p. 2157-2161 and "Pharmaceutical Research and Development" (Hirokawa Publishing Company) 1990, Vol. 7, Drug Design, p. 163-198.

Moreover, the salt of the compound of the formula (I) is a pharmaceutically acceptable salt of the compound of the formula (I) and may form an acid addition salt depending on the kind of substituents. Specific examples thereof include acid addition salts with inorganic acids such as hydrochloric acid, hydrobromic acid, hydroiodic acid, sulfuric acid, nitric acid, and phosphoric acid; and acid addition salts with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditolyltartaric acid, citric acid, methanesulfonic acid, ethanesulfonic acid, benzenesulfonic acid, p-toluenesulfonic acid, aspartic acid, and glutamic acid.

The present invention further includes various hydrates or solvates, and polymorphic crystal substances of the compound of the formula (I) and a salt thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituent thereof and by applying various known synthesis methods. At this time, depending on the type of the functional groups, it is effective in some cases, from the viewpoint of the preparation techniques, to substitute the functional group with an appropriate protective group (a group which is capable of being easily converted into the functional group), at the stage from starting materials to intermediates. Examples of such a protective group include those described in by P. G. M. Wuts and T. W. Greene, "Greene's Protective Groups in Organic Synthesis ($4^{th}$ edition), 2006", and the like, and one of these may be appropriately selected and used as necessary depending on reaction conditions. In this kind of method, a desired compound can be obtained by introducing the protective group to carry out a reaction, and then by eliminating the protective group as necessary.

In addition, the prodrug of the compound of the formula (I) can be produced by introducing a specific group or by further carrying out the reaction using the obtained compound of the formula (I) at the stage from a starting material to an intermediate, just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below.

The following abbreviations may be used in some cases in the present specification, Examples, Preparation Examples, and Tables below.

PAM=positive allosteric modulator, PAM action=positive allosteric modulating action, CIAS=cognitive impairment associated with schizophrenia.

AcOH=acetic acid, BINAP=2,2'-bis(diphenylphosphino)-1,1'-binaphthyl, brine=saturated physiological saline, CBB=Coomassie Brilliant Blue, CHAPS=3-[(3-chloramidopropyl)dimethylammonio]propanesulfonate, DABCO=1,4-diazabicyclo[2.2.2]octane, DCE=1,2-dichloroethane, DCM=dichloromethane, CDI=1,1'-carbonyldiimidazole, D-MEM=Dulbecco's Modified Eagle's Medium, DIBAL=diisobutylaluminum, DIBOC=di-tert-butyl bicarbonate, DIPEA=N,N-diisopropylethylamine, DME=dimethoxyethane, DMF=N,N-dimethylformamide, DMSO=dimethylsulfoxide, DPPA=diphenylphosphoryl azide, DPPF=1,1'-bis(diphenylphosphino)ferrocene, EGTA=glycol ether diamine tetraacetic acid, $Et_2O$=diethylether, EtOAc=ethyl acetate, EtOH=ethanol, GABA=$\gamma$-aminobutyric acid, HATU=1-[bis(dimethylamino)methylene]-1H-1,2,3-triazolo[4,5-b]pyridin-1-ium 3-oxide hexafluorophosphate, HCl/EtOAc=hydrogen chloride/EtOAc solution, HCl/dioxane=hydrogen chloride/dioxane solution, HBSS=Hanks' balanced salt solution, Hepes=4-(2-hydroxyethyl)-1-piperazineethanesulfonic acid, HOBt=1-hydroxybenzotriazole, IPE=diisopropylethylether, $KOBu^t$=potassium tert-butoxide, LAH=lithiumaluminum hydride, MeCN=acetonitrile, MeOH=methanol, $MgSO_4$=anhydrous magnesium sulfate, Ms=methanesulfonyl, MsCl=methanesulfonyl chloride, NaOEt=sodium methoxide, $Na_2SO_4$=anhydrous sodium sulfate, $NaBH(OAc)_3$=sodium triacetoxyborohydrie, $NaOBu^t$=sodium tert-butoxide, NBS=N-bromosuccinimide, NCS=N-chlorosuccinimide, n-BuLi=n-butyllithium, NMO=N-methylmorpholine, NMP=N-methyl-2-pyrrolidone, ORF=open reading frame, $Pd(OAc)_2$=palladium (II) acetate, Pd/C=palladium on carbon, $Pd_2dba_3$=tris(dibenzylideneacetone) dipalladium (0), $Pd(PPh_3)_4$=tetrakis(triphenylphosphine) palladium (0), Red-Al=sodium bis(2-methoxyethoxy)aluminum hydride, TEA=triethylamine, THF=tetrahydrofuran, TTIP=titanium (N) isopropoxide, WSC=1-ethyl-3-(3-dimethylaminopropyl) carbodiimide, silica gel column=silica gel column chromatography, basic silica gel column=basic silica gel column chromatography, supercritical chromatography=supercritical chromatography, saturated aqueous sodium bicarbonate=saturated aqueous $NaHCO_3$ solution.

In the structural formulae, the following abbreviations may be used in some cases.

Ac=acetyl, Bn=benzyl, Boc=tert-butoxycarbonyl, Et=ethyl, Me=methyl, Ms=$SO_2CH_3$, Ph=phenyl, $^tBu$ or $Bu^t$=tert-butyl.

Furthermore, for the sake of convenience, a concentration mol/L is expressed as M. For example, a 1 M aqueous NaOH solution means a 1 mol/L aqueous NaOH solution.

(Production Process 1)

[Chem. 8]

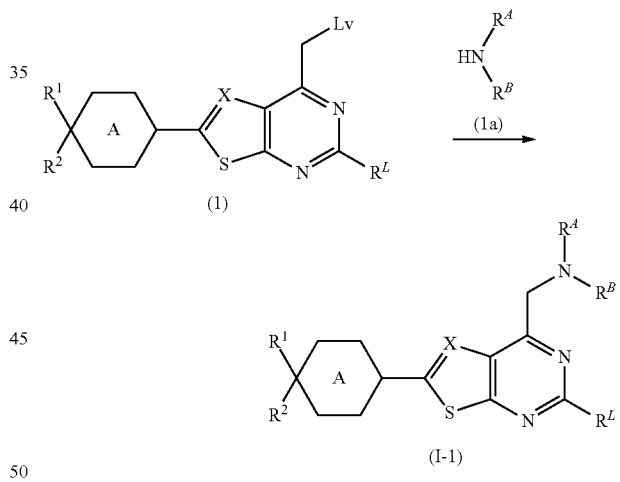

(In the formula, Lv represents a leaving group. The same shall apply hereinafter.)

The compound (I-1) of the present invention can be prepared from a compound (1) and a compound (1a).

The leaving group is, for example, halogen, an OMs group, or the like. This reaction can be carried out using the compound (1) and the compound (1a) in equivalent amounts, or with either thereof in an excess amount, by stirring a mixture thereof under any temperature condition from cooling to heating, preferably at 0° C. to 80° C., usually for 0.1 hours to 5 days, in a solvent which is inert to the reaction or without a solvent. The solvent is not particularly limited as long as it does not interfere with the reaction, but examples thereof include aromatic hydrocarbons such as toluene, xylene and the like, ethers such as $Et_2O$, THF, DME, dioxane and the like, halogenated hydrocarbons such as DCM, DCE, chloroform and the like, DMF, DMSO, EtOAc, MeCN, and a mixed solvent thereof. It may be advantageous in some cases for the smooth progress of the reaction to carry out the reaction in the presence of an organic base such as TEA, DIPEA, and NMO, or an inorganic base such as $K_2CO_3$, $Na_2CO_3$, and KOH.

DOCUMENTS

S. R. Sandler and W. Karo, "Organic Functional Group Preparations", $2^{nd}$ edition, Vol. 1, Academic Press Inc., 1991

"Jikken Kagaku Koza (Courses in Experimental Chemistry) ($5^{th}$ edition)", Vol. 14 (2005), edited by The Chemical Society of Japan, Maruzen.

(Production Process 2)

[Chem. 9]

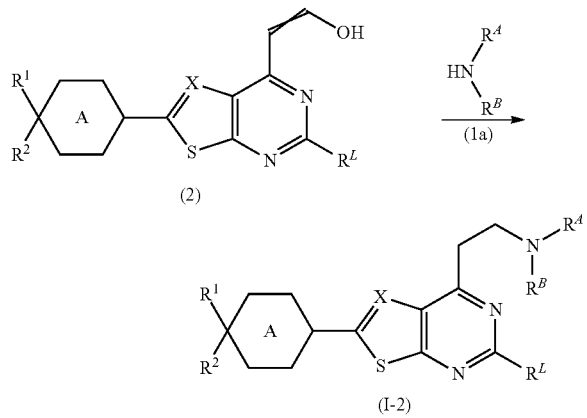

(In the formula, the crossing double bonds indicate a cis- or trans-configuration.)

The compound (I-2) of the present invention can be prepared from a compound (2) and the compound (1a).

In this reaction, the compound (2) and the compound (1a) are used in equivalent amounts, or with either thereof in an excess amount, and a mixture thereof is stirred under any temperature condition from $-30°$ C. to heating to reflux, preferably at $0°$ C. to room temperature, usually for 0.1 hours to 5 days, in a solvent which is inert to the reaction, in the presence of a reducing agent. The solvent is not particularly limited as long as it does not interfere with the reaction, but examples thereof include alcohols such as MeOH and the like, ethers, and a mixed solvent thereof. As the reducing agent, $NaBH(OAc)_3$, $NaBH_3CN$, $NaBH_4$, or the like can be used. It may be advantageous in some cases for the smooth progress of the reaction to add a dehydrating agent such as molecular sieves, AcOH, hydrochloric acid, a TTIP complex, or the like. By condensation of the compound (2) with the compound (1a), an imine is produced, and can be isolated as a stable intermediate in some cases. This imine intermediate can be subjected to reduction to prepare a compound (I-2). Further, instead of use of the reducing agent, a reduction catalyst (for example, Pd/C and a Raney nickel) can be used at normal pressure to 50 atm in a hydrogen atmosphere, in the presence or absence of an acid such as AcOH and hydrochloric acid in a solvent such as MeOH, EtOH, and EtOAc. This reaction can be carried out under any temperature condition from cooling to heating.

DOCUMENTS

"Comprehensive Organic Functional Group Transformations II", A. R. Katritzky and R. J. K. Taylor, Vol. 2, Elsevier Pergamon, 2005

"Courses in Experimental Chemistry ($5^{th}$ edition)", edited by The Chemical Society of Japan, Vol. 14 (2005) (Maruzen)

(Production Process 3)

[Chem. 10]

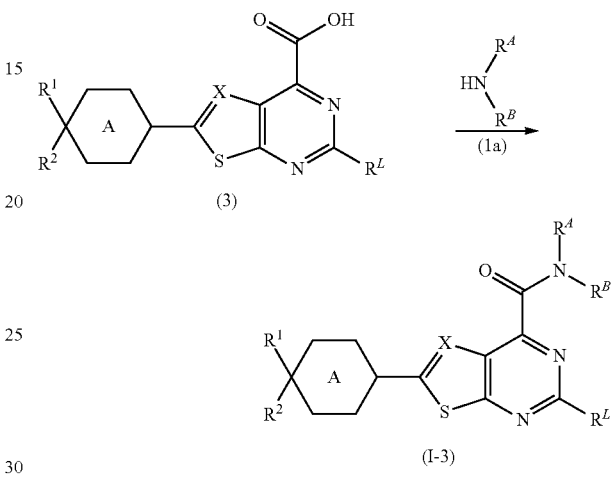

The compound (I-3) of the present invention can be prepared from a compound (3) and the compound (1a).

In this reaction, the compound (3) and the compound (1a) are used in equivalent amounts, or with either thereof in an excess amount, and a mixture thereof is stirred under any temperature condition from cooling to heating, preferably at $-20°$ C. to $60°$ C., usually for 0.1 hours to 5 days, in a solvent which is inert to the reaction, in the presence of a condensing agent. The solvent is not particularly limited as long as it does not interfere with the reaction, but examples thereof include aromatic hydrocarbons, halogenated hydrocarbons such as DCM and the like, ethers, DMF, DMSO, EtOAc, $CH_3CN$, or water, and a mixed solvent thereof. The condensing agent is, for example, WSC, CDI, DPPA, HATU, phosphorous oxychloride, or the like. With an additive such as HOBt or the like, smooth progress of the reaction may be allowed in some cases. With an organic base such as pyridine, TEA, DIPEA, NMO or the like, or an inorganic base such as $K_2CO_3$, $Na_2CO_3$, KOH or the like, smooth progress of the reaction may be allowed in some cases.

Furthermore, the compound (I-3) of the present invention can also be prepared from a reactive derivative of a carboxylic acid (3) and the compound (1a). Examples of the reactive derivative include acid halides obtained by the reaction with a halogenating agent such as phosphorus oxychloride, thionyl chloride, and the like; mixed acid anhydrides obtained by the reaction with isobutyl chloroformate or the like; and active esters obtained by condensation with HOBt or the like. In the reaction of the reactive derivative with the compound (1a), a mixture thereof can be stirred under any temperature condition from cooling to heating, preferably at $-20°$ C. to $60°$ C. usually for 0.1 hours to 5 days, with an organic base such as pyridine, TEA, DIPEA, NMO, and the like, in a solvent which is inert to the reaction. The solvent is not particularly limited as long as it does not interfere with the reaction, but halogenated hydrocarbons, aromatic hydrocarbons, ethers, or the like can be used. Further, the organic base can be used in combination with the solvent.

DOCUMENTS

S. R. Sandler and W. Karo, "Organic Functional Group Preparations", 2$^{nd}$ edition, Vol. 1, Academic Press Inc., 1991

"Jikken Kagaku Koza (Courses in Experimental Chemistry) (5$^{th}$ edition)", Vol. 16 (2005), edited by The Chemical Society of Japan (Maruzen)

formate in equivalent amounts or in an excess amount can be used as a hydrogen source, relative to the compound (4).

DOCUMENTS

M. Hudlicky, "Reductions in Organic Chemistry, 2$^{nd}$ edition (ACS Monograph: 188)", ACS, 1996

"Jikken Kagaku Koza" (Courses in Experimental Chemistry) (5$^{th}$ edition), edited by The Chemical Society of Japan, Vol. 19 (2005) (Maruzen)

(Starting Material Synthesis 1)
[Chem. 12]

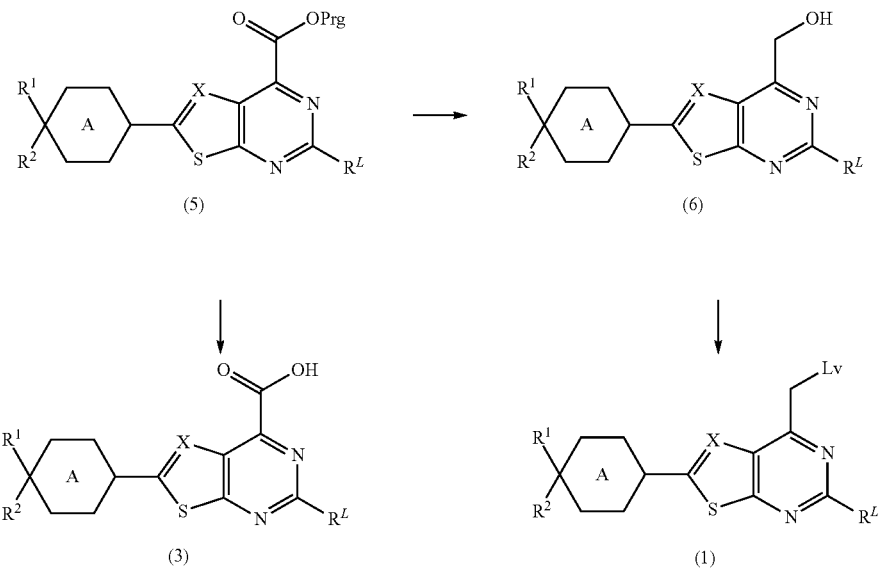

(Production Process 4)
[Chem. 11]

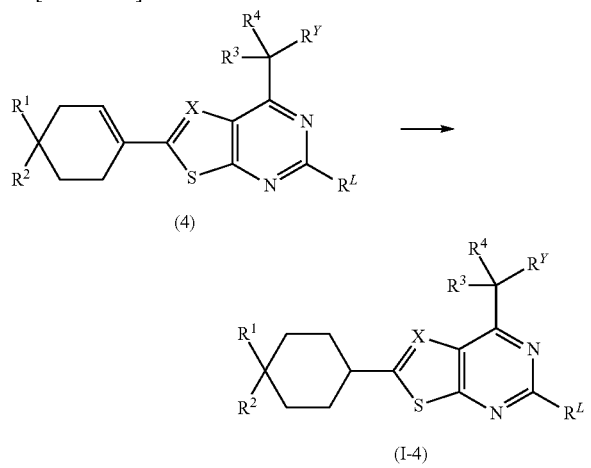

The compound (I-4) of the present invention can be prepared by the hydrogenation reaction of a compound (4).

In this reaction, the compound (4) is stirred under any temperature condition from cooling to heating, preferably at room temperature usually for 1 hour to 5 days, with a metal catalyst, in a solvent which is inert to the reaction under a hydrogen atmosphere. The solvent is not particularly limited as long as it does not interfere with the reaction, but examples thereof include alcohols, ethers, and the like. The metal catalyst is, for example, a palladium catalyst such as Pd(OH)$_2$ and the like. Instead of a hydrogen gas, formic acid or ammonium (In the formula, Prg means a protective group. The same shall apply hereinafter.)

A starting compound (1) can be prepared from a compound (6).

(i) The starting compound (1) in which Lv is halogen can be prepared by the halogenations of a compound (6). This reaction can be carried out under any temperature condition from heating to heating to reflux with a halogenating agent such as SO$_2$Cl$_2$, phosphorous oxychloride or the like, and DMF. The solvent is not particularly limited as long as it does not interfere with the reaction, but toluene or the like can be used. As the halogenating agent, PBr$_3$, NBS, or the like can be used.

(ii) The starting compound (1) in which Lv is an OMs group can be prepared by adding an organic base and MsCl to the compound (6) under any temperature condition from 0° C. to at room temperature in a solvent which is inert to the reaction under a hydrogen atmosphere. The solvent is not particularly limited as long as it does not interfere with the reaction, but DCM or the like can be used.

The compound (6) can be prepared by the reduction of a compound (5).

In this reaction, the compound (5) is treated with a reducing agent in an equivalent amount or in an excess amount, under any temperature condition from cooling to heating, preferably at −20° C. to 80° C., usually for 0.1 hours to 3 days, in a solvent which is inert to the reaction. The solvent is not particularly limited as long as it does not interfere with the reaction, but examples thereof include ethers, aromatic hydrocarbons, alcohols, and a mixed solvent thereof. As the reducing agent, NaBH$_4$, borane (BH$_3$), or a reducing agent in the following documents is used. When as the reducing agent, for example, NaBH$_4$ is used, calcium chloride may allow the smooth progress of the reaction in some cases.

DOCUMENTS

M. Hudlicky, "Reductions in Organic Chemistry, $2^{nd}$ edition (ACS Monograph: 188)", ACS, 1996

R. C. Larock, "Comprehensive Organic Transformations", $2^{nd}$ edition, VCH Publishers, Inc., 1999

T. J. Donohoe, "Oxidation and Reduction in Organic Synthesis (Oxford Chemistry Primers 6)", Oxford Science Publications, 2000

"Jikken Kagaku Koza" (Courses in Experimental Chemistry) ($5^{th}$ edition), edited by The Chemical Society of Japan, Vol. 14 (2005) (Maruzen)

The starting compound (3) can be prepared by the deprotection of the compound (5). This reaction can be carried out with reference to "Protective Groups in Organic Synthesis", Greene and Wuts, $3^{rd}$ edition, John Wiley & Sons Inc, 1999.

(Starting Material Synthesis 2)

[Chem. 13]

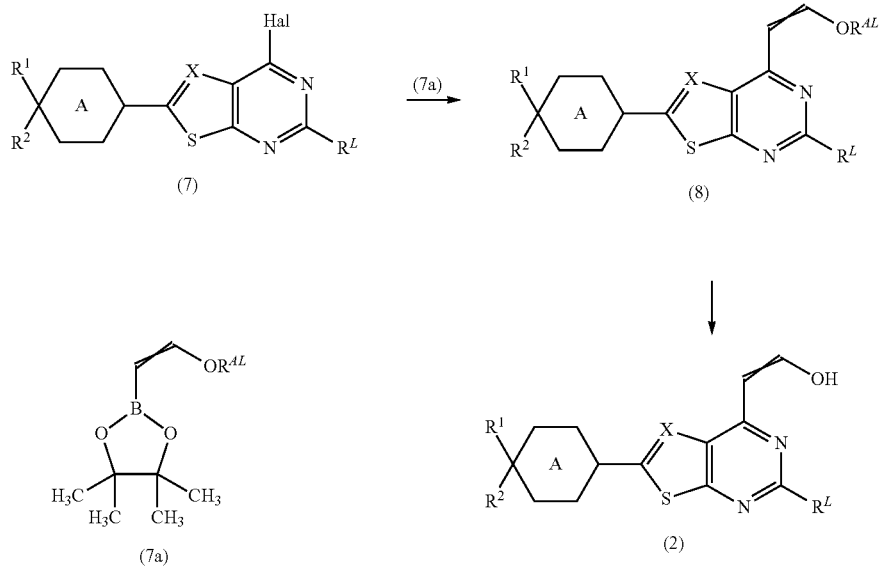

(In the formula, Hal represents halogen, $R^{AL}$ represents lower alkyl, and —$OR^{AL}$ represents lower alkyloxy. The same shall apply hereinafter.)

The compound (2) can be prepared by the deprotection of a compound (8). This reaction can be carried out with reference to "Protective Groups in Organic Synthesis", Greene and Wuts, $3^{rd}$ edition, John Wiley & Sons Inc, 1999.

The compound (8) can be prepared from a compound (7) and a lower alkyloxyetheneboronic acid pinacol ester (7a). This reaction is a so-called Suzuki coupling between the compound (7) and a boronic acid compound. This reaction can be carried out by adding palladium, a phosphine ligand, and a metal base as a reagent under any temperature condition from at room temperature to heating to reflux. The solvent is not particularly limited as long as it does not interfere with the reaction, but a solvent which is inert to the reaction, such as aromatic hydrocarbons, ethers, halogenated hydrocarbons, aprotic solvents, and AcOH may be used or a solvent may not be used. As the palladium, for example, Pd(OAc)$_2$, Pd$_2$dba$_3$, or the like can be used. As the phosphine ligand, for example, BINAP, DPPF, P(Bu$^t$)$_3$, or the like can be used. As the metal base, K$_2$CO$_3$, Cs$_2$CO$_3$, NaOBu$^t$, or the like can be used.

(Starting Material Synthesis 3)

[Chem. 14]

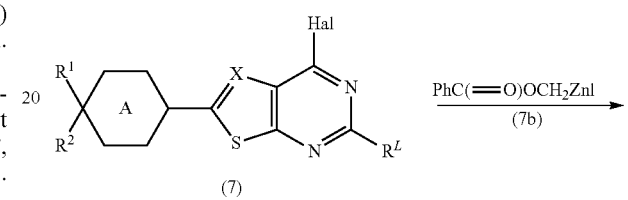

-continued

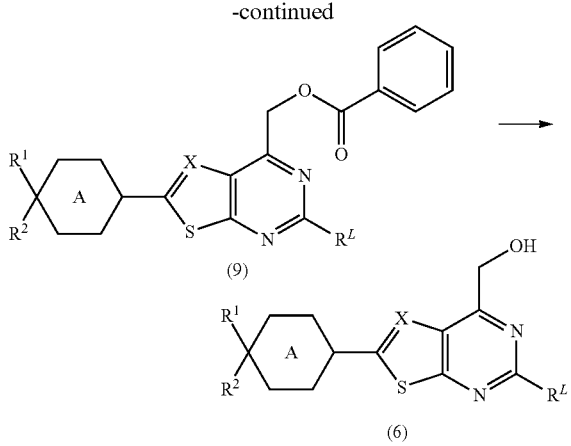

The starting compound (6) can be prepared by the hydrolysis of a compound (9).

The compound (9) can be prepared from the compound (7) and a compound (7b). This reaction is Negishi coupling, in which an organic zinc compound and an organic halide are condensed with a palladium or nickel catalyst to prepare a carbon-carbon bonding product. The solvent is not particularly limited as long as it does not interfere with the reaction, but THF or the like can be used. As the catalyst, for example, Pd(PPh$_3$)$_4$ can be used. Usually, the reaction can be carried out at room temperature.

DOCUMENTS

Negishi, E. Acc. Chem. Res. 1982, vol. 15, p. 340-348,
"Metal-Catalyzed Cross-Coupling Reactions", edited by A. de Meijere and F. Diederich, 2$^{nd}$ edition, VCH Publishers Inc., 2004, "Jikken Kagaku Koza" (Courses in Experimental Chemistry) (5$^{th}$ edition), edited by The Chemical Society of Japan, Vol. 13 (2005) (Maruzen)
Organic Letters, 2004, p. 3225, Synlett, 2008, p. 543
(Starting Material Synthesis 4)
[Chem. 15]

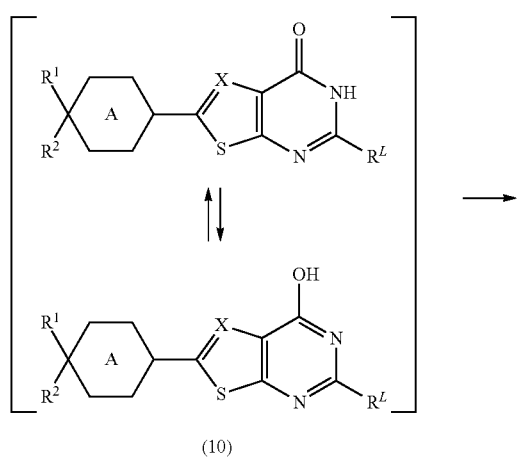

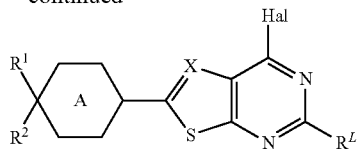

(The compound (10) is present as a tautomer as a ketoenol as described above. In the present specification, the compound (10) and Preparation Example Pr 23 and so on as described below, for the sake of convenience, are denoted by either of a keto form or an enol form.)

The compound (7) can be prepared by the halogenations of the compound (10).

This reaction can be carried out in the same manner as the method described in Starting Material Synthesis 1 above.

(Starting Material Synthesis 5)
[Chem. 16]

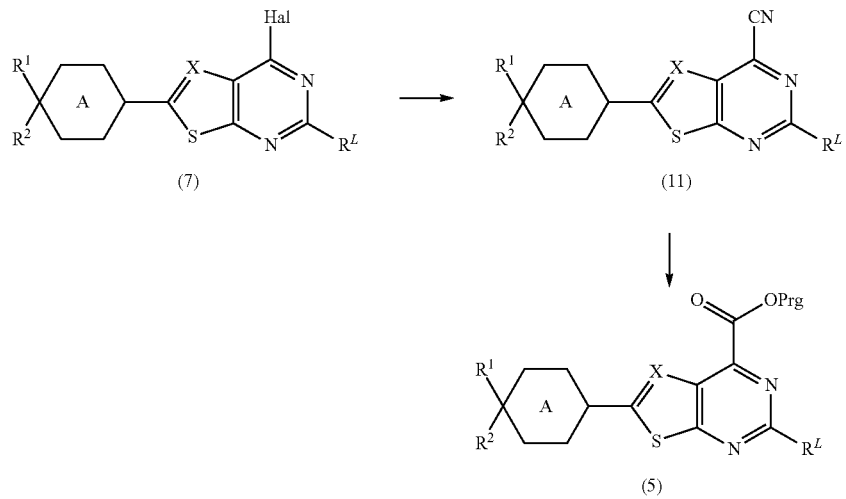

The starting compound (5) can be prepared from a compound (11). Prg is lower alkyl such as Me and Et.

This reaction can be carried out by using an alcohol (Prg-OH) as a solvent and a reagent, and stirring a mixture thereof with a compound (11) and hydrogen hydride such as HCl/dioxane and HCl/EtOAc, under any temperature condition from room temperature to heating, for several hours to overnight.

The compound (11) can be prepared by the cyanation of the compound (7). This reaction can be carried out with a CN source such as NaCN, KCN, Zn (CN)$_2$ or the like, and CH$_3$SO$_2$Na or the like, under any temperature condition from 50° C. to 80° C., for several hours to overnight under stirring. The solvent is not particularly limited as long as it does not interfere with the reaction, but DMF or the like can be used.

(Starting Material Synthesis 6)
[Chem. 17]

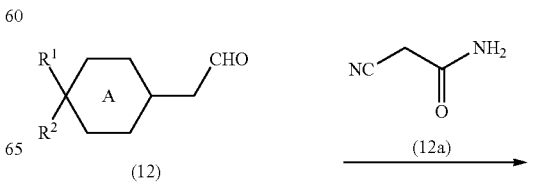

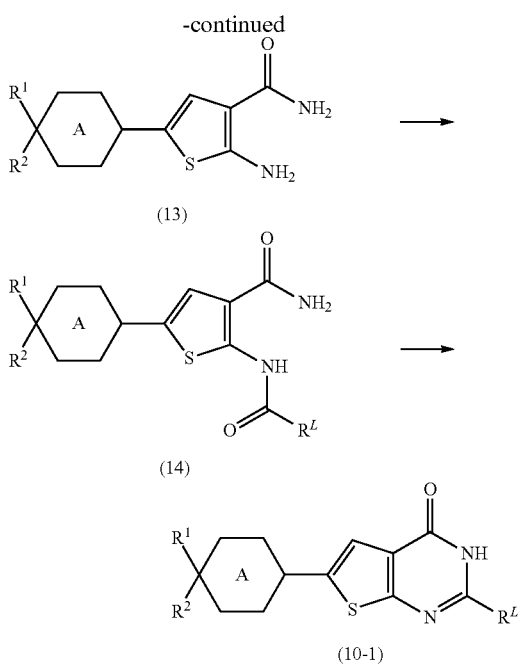

The starting compound (10-1) can be prepared from a compound (14).

This reaction can be carried out by heating and stirring the compound (14) with an aqueous inorganic base solution such as an aqueous NaOH solution or the like, in a solvent which is inert to the reaction. The solvent is not particularly limited as long as it does not interfere with the reaction, but alcohols such as EtOH and the like can be used.

The compound (14) can be prepared from a compound (13).

This reaction is amidation in which the compound (13) is reacted with an acid halide of a formula $R^L$—C(C=O)-Hal. For the reaction, the same method as Production Process 3 can be used.

The compound (13) can be prepared from the compound (12) with an organic base such as 2-cyanoacetamide (12a), sulfur, TEA, and the like in a solvent, usually by heating. The solvent is not particularly limited as long as it does not interfere with the reaction, but DMF or the like can be used.

(Starting Material Synthesis 7)
[Chem. 18]

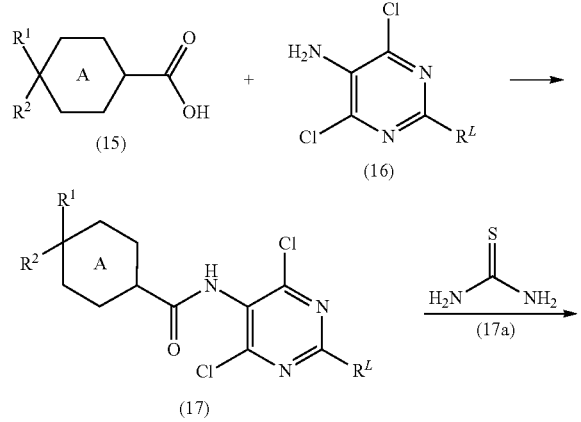

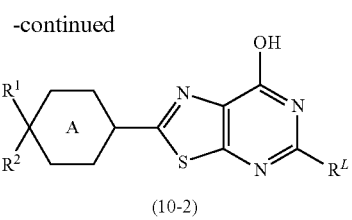

The starting compound (10-2) can be prepared from a compound (17) and a compound (17a).

This reaction can be carried out by adding formic acid to the compound (17) and the compound (17a), in a solvent which is inert to the reaction, and heating and stirring. The solvent is not particularly limited as long as it does not interfere with the reaction, but an alcohol or the like can be used.

The compound (17) can be prepared by the amidation of the compound (15) and the compound (16).

This reaction can be carried out in the same manner as the method described in Production Process 3.

(Starting Material Synthesis 8)
[Chem. 19]

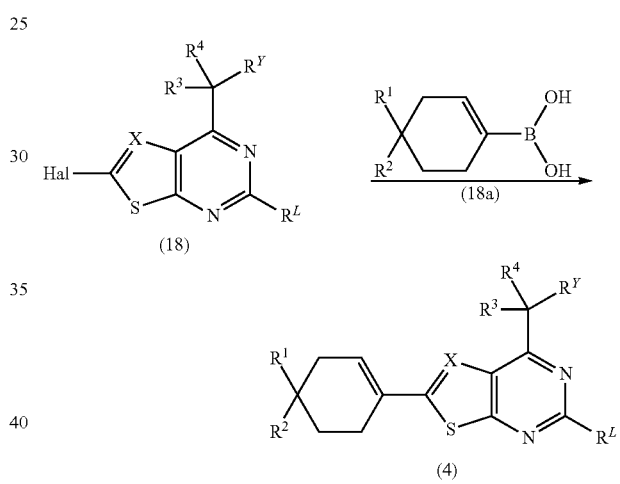

The starting compound (4) can be prepared from a compound (18) and a compound (18a).

This production process is a so-called Suzuki coupling, and can be carried out in the same manner as the method for preparing the compound (7) from the compound (8) of Starting Material Synthesis 2 as described above.

The compound of the formula (I) is isolated and purified as a free compound, a salt, a hydrate, a solvate, or a polymorphic crystal substance thereof. A salt of the compound of the formula (I) can be prepared by carrying out a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic compounds (for example, fractional crystallization for inducing diastereomer salts with optically active bases or acids, chromatography using a chiral column or the like, and others), and further, the isomers can also be prepared from an appropriate optically active starting material.

The pharmacological activity of the compound of the formula (I) or a salt thereof was confirmed by the tests below.

(Materials)

The medium composition and the buffer composition used in the following Test Examples are shown below (the concentration of each reagent represents a final concentration).

KH Buffer (Krebs-Henseleit Buffer): Aqueous solution containing 119 mM NaCl, 4.8 mM KCl, 1.2 mM $KH_2PO_4$, 1.2 mM $MgSO_4$, 2.5 mM $CaCl_2$, 25 mM $NaHCO_3$, 10 mM Glucose, and 20 mM Tris-HCl (pH=7.4).

A Buffer: Aqueous solution containing 0.32 M sucrose, 1 mM $MgCl_2$, and 1 mM $K_2HPO_4$.

B Buffer: Aqueous solution containing 50 mM Tris-HCl (pH=7.7), 100 mM NaCl, 10 mM $MgCl_2$, 2 mM $CaCl_2$, 0.2 mM EGTA, and 30 μM GDP.

C Buffer: Aqueous solution containing 20 mM Tris-HCl (pH=7.7) and 5 mM $MgCl_2$.

Base buffer: Aqueous solution containing 2.5 mM probenecid, 20 mM Hepes-NaOH (pH=7.5), and a Hanks' balanced salt solution (HBSS) containing 0.02% CHAPS.

Fluo-4 loaded solution: Base buffer containing 1 μM Fluo-4 AM (Dojindo Molecular Technologies, Inc.), 0.067% DMSO and 0.0033% Pluronic F-127 (Life Technologies).

Test Example 1

Confirmation of PAM Action by GTPγS Binding Test

The function of the $GABA_B$ receptor of the compound of the present invention was evaluated using a [$^{35}$S] GTPγS binding test. This method is used for the detection of the PAM action of the compound on the $GABA_B$ receptor (Journal of Pharmacology and Experimental Therapeutics, 2003, vol. 307(1), p. 322-330; and Molecular Pharmacology, 2001, vol. 60(5), p. 963-971).

(Membrane Preparations)

The mouse brain cortical membrane was prepared with reference to a method for preparing a rat brain membrane (European Journal of Pharmacology, 1990, vol. 187 (1), p. 27-38).

The cortex (about 30 g) was cut out of the brains of 90 ddY mice (Japan SLC, Inc.). An A buffer was added to the cortex (cortex/A buffer=about 1:3 (wt/vol)), and homogenized with a glass Teflon-lined homogenizer (Teflon: registered trademark) on ice. The homogenate was centrifuged (750 g, 10 min, 4° C.) and a supernatant was then obtained. An A buffer (90 mL) was added to pellets and homogenized on ice, and a supernatant (750 g, 10 min, 4° C.) was then obtained. By repeating this operation, the supernatant was collected.

The supernatant was centrifuged (18000 g, 15 min, 4° C.). Ultrapure water (54 mL) was added to the pellets, left to stand for 30 min on ice, and then centrifuged (39000 g, 20 min, 4° C.). The pellets were suspended in a KH buffer (54 mL), repeatedly frozen and thawed, and centrifuged (18000 g, 15 min) at 4° C. The buffer was added to the pellets and then frozen and thawed, and this operation was repeated until the centrifugation. By a Bradford method using a protein assay (Protein assay CBB solution; Nacalai Tesque, Inc.), a KH buffer suspension of the pellet was prepared at a protein concentration of 10 mg/mL.

(GTPγS Binding Test)

The PAM action of the $GABA_B$ receptor in the mouse brain cortex of a test drug was evaluated. To each of wells of a 96-well microplate, a test drug diluted with a B buffer at each concentration (3 nM to 30 μM), a mouse brain cortex membrane (4 μg), [$^{35}$S] GTPγS (final concentration of 0.34 nM, Muromachi Yakuhin Co., Ltd.; Institute of Isotopes Co., Ltd.), GABA (final concentration of 0.3 μM; Sigma) were added in this order, followed by standing at room temperature for 1 hour. With a harvester (Filtermate, Perkin-Elmer, Inc.), the suspension was suction-filtered through a glass filter (UniFilter 96-well GF/B filter plates, Perkin-Elmer, Inc.). The glass filter was washed with a C buffer that had been ice-cooled. After drying the glass filter, a liquid scintillation cocktail (50 μL, MicroScinti-PS; PerkinElmer, Inc.) was added to each well. The amount of [$^{35}$S] GTPγS bound to the membrane was measured on a plate reader (TopCount, PerkinElmer, Inc.).

(Data Analysis)

The maximum reaction rate of 100 μM GABA was taken as 100%. The reaction rate when GABA and the test drug did not exist was taken as 0%. At a time when the test drug was not added, the concentration of the test drug that increased the reaction rate from 20% with 0.3 μM GABA to 50% was taken as a PAM Potency (μM) of the $GABA_B$ of the test drug. In the presence of 0.3 μM GABA, the maximum reaction rate of the effect on the $GABA_B$ receptor when the test drug was administered up to maximum 30 μM was taken as a PAM Efficacy (%) of the $GABA_B$ of the test drug.

The Potency and Efficacy of several representative Example Compounds of the present invention are shown in Table below (In the Table, Ex represents Example Compound No. The "Potency" represents the PAM Potency of $GABA_B$ of the test drug, and the "Efficacy" represents PAM Efficacy (%) of $GABA_B$ of the test drug. These shall apply hereinafter).

TABLE 1

| No. | Potency (μM) | Efficacy (%) |
|---|---|---|
| Ex2 | 0.11 | 207 |
| Ex4 | 0.20 | 161 |
| Ex5 | 0.24 | 176 |
| Ex7 | 0.24 | 139 |
| Ex12 | 0.23 | 377 |
| Ex31 | 0.11 | 300 |
| Ex31-1 | 0.18 | 191 |
| Ex39 | 0.42 | 165 |
| Ex40 | 0.53 | 203 |
| Ex43 | 0.26 | 118 |
| Ex44 | 0.27 | 119 |
| Ex45 | 0.44 | 134 |
| Ex46 | 0.18 | 188 |
| Ex47 | 0.12 | 240 |
| Ex48 | 0.26 | 238 |
| Ex50 | 0.54 | 222 |
| Ex51 | 0.15 | 249 |
| Ex52 | 0.17 | 259 |
| Ex54 | 0.32 | 88 |
| Ex55 | 0.25 | 175 |
| Ex61 | 0.24 | 160 |
| Ex72 | 0.089 | 289 |
| Ex73 | 0.085 | 272 |
| Ex74 | 0.19 | 244 |
| Ex79 | 0.046 | 230 |
| Ex101 | 0.38 | 134 |
| Ex102 | 0.40 | 127 |
| Ex104 | 0.079 | 218 |
| Ex108 | 0.20 | 176 |
| Ex127 | 0.11 | 338 |
| Ex132 | 0.15 | 218 |
| Ex142 | 0.0071 | 214 |
| Ex143 | 1.2 | 182 |
| Ex144 | 0.31 | 182 |
| Ex146 | 0.10 | 258 |
| Ex151 | 0.12 | 168 |

TABLE 1-continued

| No. | Potency (μM) | Efficacy (%) |
|---|---|---|
| Ex153 | 0.059 | 180 |
| Ex155 | 0.046 | 159 |

Test Example 2

Confirmation of PAM Action Using Cells that Stably Express $GABA_B$ Receptor

A natural $GABA_B$ receptor has a heterodimeric structure consisting of two kinds of subunits of $GABA_{B1}$ and $GABA_{B2}$ (Nature, 1997, vol. 386, p. 239-246) In the subunit of $GABA_{B1}$, two major splice variants referred to as $GABA_{B1a}$ and $_{1b}$ exist. However, the two variants have no difference in the pharmacological effects in the receptor-downstreaming signals (Nature, 1998, vol. 396, p. 683-687).

In HEK293 cells expressing the heterodimers of $GABA_{B1b}$ and $GABA_{B2}$, the PAM action in the presence of GABA was measured over time with a change in the intracellular $Ca^{2+}$ concentration using RFU (relative fluorescence units) as an index, and evaluated.

(Establishment of Cell Lines Expressing $GABA_B$ Receptors)

All vectors, wherein each vector was formed by human $GABA_{B1b}$ (NM_021903. 2), $GABA_{B2}$ (NM_005458. 7), or Gαqo chimera, were incorporated by lipofection to establish stably expressing human embryonic kidney-derived cell lines, HEK293 cells (ATCC).

The Gαqo chimera was fabricated by the following method. The genes coding human Gαq (NM_002072.3) were cloned, and C-terminal 15 base pairs (1107-1121 bp) of ORF (41-1121 bp) of Gaq was substituted with C-terminal 15 base pairs (1948-1962 bp) of ORF (898-1962 bp) of human Gao (NM_138736. 2) into a Gαqo chimera.

(Measurement of Intracellular Calcium Mobilization Due to $GABA_B$ Receptor Activation by FLIPR)

A change in the intracellular concentration of calcium mobilized due to activation of a $GABA_B$ receptor was measured with a Fluorometric Imaging Plate Reader (FLIPR, Molecular Devices). The stably expressing cells established as described above were proliferated in a D-MEM medium containing a screening agent (0.5 mg/mL G418 Disulfate and 0.2 mg/mL Hydromycin B solution), 1% penicillin/streptomycin, and 10% FCS. About $1 \times 10^4$ cells/well were diluted and seeded in a black-wall, 384-well poly-D-lysin-coated plate (Becton Dickinson) in a D-MEM medium containing 10% FCS, but not a selective agent and 1% penicillin/streptomycin. After 24 hours, the medium was removed from the plate, and a Fluo-4 loaded solution (20 μL) was added to each well, followed by incubation at room temperature for 2 hours. The fluorescent reagent loaded solution was removed from each well, the cells were washed with a base buffer three times, and then a base buffer (20 μL) was added thereto, followed by analysis with FLIPR TETRA (Molecular Devices). The base buffer (10 μL) solution of the test drug was added thereto to a final concentration (1 nM to 30 μM) and the measurement of a change in the fluorescence was initiated. Thereafter, GABA (1 μM, 20 μL) was added thereto and the measurement was continued. The change in the fluorescence was measured every two or five seconds.

(Data Analysis)

The maximum reaction rate of 100 μM GABA was taken as 100%. The reaction rate when GABA and the test drug did not exist was taken as 0%. At a time when the test drug was not added, the concentration of the test drug that increased the reaction rate from 5% with 1 μM GABA to 50% was taken as a PAM Potency (μM) of the $GABA_B$ of the test drug. In the presence of 1 μM GABA, the maximum reaction rate of the effect on the $GABA_B$ receptor when the test drug was administered up to maximum 30 μM was taken as a PAM Efficacy (%) of the $GABA_B$ of the test drug.

The evaluation test results in FLIPR of several representative Example Compounds of the present invention are shown in Table below.

TABLE 2

| No. | Potency (μM) | Efficacy (%) |
|---|---|---|
| Ex2 | 0.059 | 470 |
| Ex31 | 0.22 | 273 |

Test Example 3

Y-Maze Test: Improvement Effect on Cognitive Impairment

The effect on the improvement of short-term memory impairment of the compound of the present invention was evaluated using a Y-maze test that is an experimental system of spontaneous alternation behavior.

(Experiment Device)

As the Y maze, a maze, in which three runways having a length of one arm of 40 cm, a height of a wall of 13 cm, a width of a floor of 3 cm, and a width of a top of 10 cm are each joined at 120 degrees in a Y shape, was used.

(Test Method)

The test drugs were orally administered once to 5- to 6-week old ddY male mice (n=8) at 30 minutes before the initiation of the Y-maze test, and further, MK-801 (Sigma) which is an NMDA receptor antagonist inducing cognitive impairment was intraperitoneally administered thereto at a dose of 0.15 mg/kg at 20 minutes before the initiation of the Y-maze test.

Further, for the mice in a control group, a vehicle (0.5% methyl cellulose) was used instead of the test drug, and physiological saline was used instead of MK-801.

For the mice in the MK-801 control group, a vehicle (0.5% methyl cellulose) was used instead of the test drug.

The mouse was placed at one end of a certain place in the runway in the Y maze, and then freely explored for 8 minutes, and the runways into which the mice invaded and the order thereof were recorded. The number of the entries of the mice within a measurement time was counted and defined as a total number of entries. Among these, a combination when the mice invaded into different three runways (for example, in a case where the three arms are referred to as a, b, and c, respectively, and the order of the arms with entries is abccba-cab, the number was counted as 4, including the repetition) was defined as the number of spontaneous alternation behaviors. For the spontaneous alternation rate, a spontaneous alternation rate calculated by the following equation was taken as an index of spontaneous alternation behavior:

Spontaneous alternation rate=number of spontaneous alternation behaviors/(total number of entries−2)×100.

A higher value of this index indicates that more short-term memory is retained.

(Data Analysis) The measured value was expressed in an average value±a standard error. A significant difference assay between the control group and the MK-801 control group was carried out by a Student's t-test. Further, a Dunnett's multi-comparison test was carried out in a significant difference assay between the group administered with the test drug and the MK-801 control group, and it was thus determined that the test drug has an action to improve the learning disorder. In each test, if p<0.05 was satisfied, it was determined that there was a significant difference.

The MED (mg/kg) of several representative Example Compounds in the present invention are shown in Table below.

TABLE 3

| No. | MED (mg/kg) |
| --- | --- |
| Ex2 | 0.1 |
| Ex31 | 1.0 |

Test Example 4

Effect on Pressure Pain Threshold in Model with Reserpine-Induced Muscle Pain

This model is a model that mimics the pathological conditions of fibromyalgia. This test was carried out on the basis of the description in Pain, 2009, vol. 146, p. 26-33. Reserpine (1 mg/kg) was subcutaneously administered to the male SD rat (Japan SLC, Inc.)) once per day for 3 days. After 5 days, the solvent or the test drug was orally administered. After 30 minutes, the pressure pain threshold value was measured using a Randall-Selitto instrument (Muromachi Kikai Co., Ltd.) in the gastrocnemius muscle. The significant difference assay between the solvent group and the group administered with the test drug was carried out by comparison between the groups using a Student's t-test or a Dunnett's multiple comparison test. Here, the value obtained by administering a solvent to a normal rat not administered with reserpine was taken as 100%, and the value of the reserpine group administered with a solvent was taken as 0%. In each assay, if p<0.05 was satisfied, it was determined that there was a significant difference.

TABLE 4

| No. | MED (mg/kg) |
| --- | --- |
| Ex2 | 0.03 |

As a result of the tests above, it was found that the compound of the present invention has a PAM action of the $GABA_B$ receptor. Accordingly, the compound is useful for preventing or treating $GABA_B$ receptor-related diseases or disorders, for example, schizophrenia, CIAS, cognitive impairment, fragile X syndrome, autism spectrum disorder, spasticity, anxiety disorder, substance addiction, pain, fibromyalgia, Charcot-Marie-Tooth disease, or the like.

A pharmaceutical composition containing one or two or more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration injections, such as intraarticular, intravenous, or intramuscular injections, and the like, suppositories, ophthalmic solutions, eye ointments, transdermal liquid preparations, ointments, transdermal patches, transmucosal liquid preparations, transmucosal patches, inhalers, and the like.

As the solid composition for oral administration, tablets, powders, granules, or the like are used. In such a solid composition, one or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, and antiseptics.

The injections for parenteral administration include sterile aqueous or non-aqueous solution preparations, suspensions and emulsions. The aqueous solvent includes, for example, distilled water for injection and physiological saline. Examples of the non-aqueous solvent include alcohols such as EtOH. Such a composition may further contain a tonicity agent, an antiseptic, a moistening agent, an emulsifying agent, a dispersing agent, a stabilizing agent, or a solubilizing aid. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

Examples of the agent for external use includes ointments, plasters, creams, jellies, patches, sprays, lotions, eye drops, eye ointments, and the like. The agents contain generally used ointment bases, lotion bases, aqueous or non-aqueous liquid preparations, suspensions, emulsions, or the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For the administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like, or other forms.

In general oral administration, the daily dose is suitably from about 0.001 mg/kg to 100 mg/kg, preferably from 0.1 mg/kg to 30 mg/kg, and more preferably from 0.1 mg/kg to 10 mg/kg, per body weight, administered in one portion or in 2 to 4 divided portions. In the case of intravenous administration, the daily dose is suitably from about 0.0001 mg/kg to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

Although varying depending on administration routes, dosage forms, administration sites, or the types of excipients and additives, the pharmaceutical composition of the present invention contains 0.01% by weight to 100% by weight, and in a certain embodiment, 0.01% by weight to 50% by weight of one or more kinds of the compound of the formula (I) or a salt thereof, which is an active ingredient.

The compound of the formula (I) can be used in combination with various agents for treating or preventing the diseases for which the compound of the formula (I) is considered to be effective. The combined preparation may be administered simultaneously, or separately and continuously, or at a desired time interval. The preparations to be co-administered may be a blend, or may be prepared individually.

EXAMPLES

Hereinbelow, the preparation methods for the compound of the formula (I) will be described in more detail with reference to Examples. Further, the present invention is not limited to the compounds described in the Examples as described below. Furthermore, the production processes for the starting compounds will be described in Preparation Examples. Further, the preparation methods for the compound of the formula (I) are not limited to the preparation methods of the specific Examples as below, but the compound of the formula (I) can be prepared by any combination of the preparation methods or the methods that are apparent to a person skilled in the art.

The compounds shown in the following Table were prepared by using the above-mentioned preparation methods and the methods that are apparent to a person skilled in the art, or modified methods thereof. The tables show the structures and physicochemical data of the Example Compounds and methods for preparing the compounds. Further, the symbols in the tables represent the following meanings.

No.=Example No. or Preparation Example No.

No./Inf=(Example No. or Preparation Example No. of the compound)/(salt information of the compound). /Inf, for example, /HCl denotes that the Example Compound is a monohydrochloride. Further, a case where /2HCl is described means that the compound is a dihydrochloride. In addition, /FUM denotes that the compound is fumarate. A case where nothing is described indicates that the compound is a free form. In the tables, Chiral denotes that the compound is an optically active form.

Pr=Preparation Example No., Ex=Example No., Ref=preparation method (the numeral shows that the Example Compound was prepared by the same preparation method as that for a compound having its number as the Example No. Further, in the tables, for example, in Ex86, a case where Pr8+Ex85 is described denotes that a material is prepared by the same method as for the preparation of Preparation Example Compound 8 (Pr8), and then, by using the obtained material as starting material. A desired product is prepared by the same method as for the preparation of Example Compound 85 (Ex85). Further, in Tables, for example, in Pr26, a case where Pr8+Ex1 is described denotes that a material is prepared by the same method as for the preparation of Preparation Example Compound 8 (Pr8), and then, by using the obtained material as starting material. A desired product is prepared by the same method as for the preparation of Example Compound 1 (Ex1)).

Str=Structural formula, Data=Physicochemical data.

NMR (CDCl$_3$)=Chemical shift δ value in $^1$H-NMR, as measured using CDCl$_3$ as a solvent, NMR (DMSO-d$_6$)= Chemical shift δ value in $^1$H-NMR, as measured using DMSO-d$_6$ as a solvent, EI=m/z value measured by EI-MS, ESI=m/z value measured by ESI-MS, APCI=m/z value measured by APCI-MS, APCI/ESI=m/z value measured by APCI and ESI at once, CI=m/z value measured by CI-MS. Further, in a case where + or − is described as a suffix in ESI or the like, + means a MS value measured in a positive ion mode and − means a MS value measured in a negative ion mode.

Preparation Example 3

To a mixture of 2-acetamide-5-(4,4-dimethylcyclohexyl) thiophene-3-carboxamide (37.3 g) and EtOH (200 mL) was added a 2 M aqueous NaOH solution (200 mL), followed by heating and stirring at 80° C. for 2 hours. The reaction mixture was left to be cooled to room temperature, and then, 1 M hydrochloric acid (500 mL) was added thereto, followed by stirring at room temperature. The precipitate was collected by filtration to obtain 6-(4,4-dimethylcyclohexyl)-2-methylthieno[2,3-d]pyrimidin-4(3H)-one (26.3 g).

Preparation Example 4

To a mixture of 6-cyclohexyl-2-methylthieno[2,3-d]pyrimidin-4(3H)-one (25.0 g) and toluene (300 mL) were added phosphorous oxychloride (14 mL) and DMF (200 μL), followed by heating to reflux at 150° C. for 14 hours. The reaction mixture was left to be cooled to room temperature and concentrated under reduced pressure. To the residue were added chloroform, water, and saturated aqueous sodium bicarbonate, followed by stirring. The reaction mixture was extracted with chloroform. The organic layer was washed sequentially with water and brine. To the organic layer were added MgSO$_4$, activated carbon (2 g), and silica gel (100 mL), followed by stirring. The mixture was filtered through Celite and then concentrated under reduced pressure to obtain 4-chloro-6-cyclohexyl-2-methylthieno[2,3-d]pyrimidine (27.4 g).

Preparation Example 4-1

To a mixture of 6-(4,4-dimethylcyclohexyl)-2-methylthieno[2,3-d]pyrimidin-4(3H)-one (30.0 g) and toluene (240 mL) were added phosphorous oxychloride (40 mL) and DMF (1.0 mL), followed by heating to reflux at 130° C. for 2 hours. The reaction mixture was left to be cooled to room temperature and concentrated under reduced pressure. To the residue were added chloroform and saturated aqueous sodium bicarbonate, followed by stirring. The organic layer was washed sequentially with water and brine. To the organic layer were added MgSO$_4$, activated carbon (10 g), and silica gel (100 mL), followed by stirring. The mixture was filtered through Celite and then concentrated under reduced pressure to obtain 4-chloro-6-(4,4-dimethylcyclohexyl)-2-methylthieno[2,3-d]pyrimidine (31.3 g).

Preparation Example 4-6

To a mixture of 2-(4,4-dimethylcyclohexyl)-5-methyl[1,3] thiazolo[5,4-d]pyrimidin-7-ol (16.2 g) and toluene (160 mL)

were added DMF (10 mL) and phosphorous oxychloride (11 mL), followed by stirring at 95° C. for 30 minutes. The reaction mixture was concentrated under reduced pressure. To the residue was added chloroform, and the mixture was neutralized with a 1 M aqueous NaOH solution in an ice bath and extracted with chloroform. The organic layer was dried over MgSO$_4$ and then concentrated under reduced pressure. The residue was purified by silica gel column (hexane/EtOAc) to obtain 7-chloro-2-(4,4-dimethylcyclohexyl)-5-methyl[1,3]thiazolo[5,4-d]pyrimidine (13.2 g).

Preparation Example 5

To a mixture of 4-chloro-6-(4,4-dimethylcyclohexyl)-2-methylthieno[2,3-d]pyrimidine (31.1 g) and DMF (220 mL) were added CH$_3$SO$_2$Na (11 g) and KCN (10 g), followed by heating and stirring at 70° C. for 15 hours. The reaction mixture was concentrated to about a half of the amount under reduced pressure, diluted with water (300 mL), and then stirred. The precipitate was collected by filtration. To the precipitate was added chloroform, followed by dissolving therein, and MgSO$_4$, activated carbon (10 g), and silica gel (100 mL) were added thereto, followed by stirring. The mixture was filtered through Celite and then concentrated under reduced pressure to obtain 6-(4,4-dimethylcyclohexyl)-2-methylthieno[2,3-d]pyrimidine-4-carbonitrile (27.4 g).

Preparation Example 6

To a mixture of 6-cyclohexyl-2-methylthieno[2,3-d]pyrimidine-4-carbonitrile (23.5 g) and EtOH (100 mL) was added 4 M HCl/dioxane (100 mL), followed by stirring at 80° C. for 2 days. The reaction mixture was left to be cooled to room temperature and concentrated under reduced pressure. To the residue was added chloroform, followed by dissolving therein, and activated carbon (2 g) and basic silica gel (100 mL) were further added thereto, followed by stirring. The mixture was filtered through Celite and then concentrated under reduced pressure to obtain ethyl 6-cyclohexyl-2-methylthieno[2,3-d]pyrimidine-4-carboxylate (30.8 g).

Preparation Example 6-1

To a mixture of 6-(4,4-dimethylcyclohexyl)-2-methylthieno[2,3-d]pyrimidine-4-carbonitrile (27.4 g) and EtOH (200 mL) was added 4 M HCl/dioxane (200 mL), followed by stirring at 80° C. overnight. The reaction mixture was left to be cooled to room temperature and then concentrated under reduced pressure. To the residue were added EtOH (200 mL) and water (200 mL), followed by stirring. The precipitate was collected by filtration. To the obtained precipitate was added chloroform, followed by dissolving therein, and MgSO$_4$, activated carbon (10 g), and basic silica gel (100 mL) were added thereto, followed by stirring. The mixture was filtered through Celite and then concentrated under reduced pressure to obtain ethyl 6-(4,4-dimethylcyclohexyl)-2-methylthieno[2,3-d]pyrimidine-4-carboxylate (23.3 g).

Preparation Example 7

To a mixture of ethyl 6-cyclohexyl-2-methylthieno[2,3-d]pyrimidine-4-carboxylate (29.3 g), calcium chloride (18 g), and THF (200 mL) was added NaBH$_4$ (5.5 g) in small divided portions at room temperature, and then EtOH (200 mL) was slowly added thereto over 5 minutes, followed by stirring at room temperature for 4 hours. To the reaction mixture was added ice water, followed by stirring, adding 1 M hydrochloric acid until the suspension becomes a solution state, and then extracting with EtOAc. The organic layer was washed sequentially with water, saturated aqueous sodium bicarbonate, and brine. To the organic layer were added MgSO$_4$, activated carbon, and basic silica gel, followed by stirring. The mixture was filtered through Celite and then concentrated under reduced pressure. The residue was purified by silica gel column (chloroform/EtOAc) to obtain (6-cyclohexyl-2-methylthieno[2,3-d]pyrimidin-4-yl)methanol (12.7 g).

Preparation Example 7-1

To a mixture of ethyl 6-(4,4-dimethylcyclohexyl)-2-methylthieno[2,3-d]pyrimidine-4-carboxylate (13.0 g), THF (150 mL), and EtOH (150 mL) was added calcium chloride (6.6 g), followed by stirring at room temperature for 30 minutes and then adding NaBH$_4$ (1.8 g) in small divided portions over 15 minutes under ice-cooling. After stirring at room temperature for 4.5 hours, to the reaction mixture were added water (100 mL) and EtOAc (100 mL) under ice-cooling. 1 M Hydrochloric acid (100 mL) was added thereto until the suspension became a solution, followed by concentration under reduced pressure and extracting with EtOAc. The organic layer was washed sequentially with water, saturated aqueous sodium bicarbonate, and brine, dried over MgSO$_4$, and then concentrated under reduced pressure. The residue was purified by silica gel column (chloroform/EtOAc) to obtain [6-(4,4-dimethylcyclohexyl)-2-methylthieno[2,3-d]pyrimidin-4-yl]methanol (9.35 g).

Preparation Example 8

To a mixture of [6-(4,4-dimethylcyclohexyl)-2-methylthieno[2,3-d]pyrimidin-4-yl]methanol (16.0 g), TEA (10 mL) and DCM (200 mL) was added dropwise MsCl (5.0 mL) at 0° C. for 15 minutes, followed by stirring at the same temperature for 1 hour. To the reaction mixture was added saturated aqueous sodium bicarbonate, followed by extraction with chloroform. The organic layer was washed sequentially with saturated aqueous sodium bicarbonate and brine. To the organic layer were added MgSO$_4$, activated carbon (5 g), and basic silica gel (20 mL), followed by stirring. The mixture was filtered through Celite and then concentrated under reduced pressure to obtain [6-(4,4-dimethylcyclohexyl)-2-methylthieno[2,3-d]pyrimidin-4-yl]methyl methanesulfonate (18.9 g).

Preparation Example 8-7

To a mixture of [2-(4,4-dimethylcyclohexyl)-5-methyl[1,3]thiazolo[5,4-d]pyrimidin-7-yl]methanol (6.42 g) and EtOAc (65 mL) were added dropwise TEA (4.5 mL) and MsCl (2.1 mL) under ice-cooling, followed by stirring at 0° C. for 1 hour. The reaction mixture was filtered and then to the liquid was added saturated aqueous sodium bicarbonate, followed by extraction with EtOAc. The organic layer was dried over MgSO$_4$ and then concentrated under reduced pressure to obtain [2-(4,4-dimethylcyclohexyl)-5-methyl[1,3]thiazolo[5,4-d]pyrimidin-7-yl]methyl methanesulfonate (9.3 g).

Preparation Example 9

To a mixture of N-(4,6-dichloro-2-methylpyrimidin-5-yl)-4,4-dimethylcyclocarboxamide (23.8 g) and EtOH (200 mL) were added thiourea (6 g) and formic acid (900 µL), followed by heating and stirring at 85° C. for 15 hours. To the reaction mixture was added water, followed by extraction with chloroform. The organic layer was dried over MgSO$_4$ and then concentrated under reduced pressure. The residue was purified by silica gel column (chloroform/MeOH) to obtain 2-(4,4-dimethylcyclohexyl)-5-methyl[1,3]thiazolo[5,4-d]pyrimidin-7-ol (16.2 g).

Preparation Example 10

Under an argon atmosphere, to a suspension of zinc powder (7.5 g) in THF (50 mL) were added dibromoethane (200 µL) and trimethylsilylchloride (200 µL), and then a solution of iodomethyl benzoate (15 g) in THF (50 mL) was added thereto, followed by stirring at room temperature for 1 hour. Then, a solution of 7-chloro-2-(4,4-dimethylcyclohexyl)-5-methyl[1,3]thiazolo[5,4-d]pyrimidine (10.9 g) in THF (50 mL) and Pd(PPh$_3$)$_4$ (4.25 g) were added thereto, followed by stirring at room temperature for 15 hours. The reaction mixture was filtered through Celite and then concentrated under reduced pressure. To the residue was added a 1 M aqueous NH$_4$Cl solution, followed by extraction with EtOAc. To the organic layer were added MgSO$_4$ and basic silica gel, followed by stirring, filtrating, and then concentrating under reduced pressure. The residue was purified by silica gel column (hexane/EtOAc) to obtain [2-(4,4-dimethylcyclohexyl)-5-methyl[1,3]thiazolo[5,4-d]pyrimidin-7-yl]methyl benzoate (13.8 g).

Preparation Example 11

To a mixture of [2-(4,4-dimethylcyclohexyl)-5-methyl[1,3]thiazolo[5,4-d]pyrimidin-7-yl]methyl benzoate (13.8 g) and MeOH (250 mL) was added a 28% NaOCH$_3$ solution (670 µL) in MeOH, followed by stirring at room temperature for 3 hours. The reaction mixture was neutralized by the addition of 4 M HCl/EtOAc (870 µL), and concentrated under reduced pressure. To the residue was added water, followed by extraction with EtOAc. To the organic layer were added MgSO$_4$ and basic silica gel, followed by stirring. The mixture was filtered through Celite and then concentrated under reduced pressure. The residue was purified by silica gel column (hexane/EtOAc) to obtain [2-(4,4-dimethylcyclohexyl)-5-methyl[1,3]thiazolo[5,4-d]pyrimidin-7-yl]methanol (7.9 g).

Preparation Example 12

To a mixture of 2-amino-5-cyclohexylthiophene-3-carboxamide (53.5 g) and THF (500 mL) were added dropwise acetyl chloride (18 mL) and TEA (36 mL) under ice-cooling, followed by stirring at room temperature for 17 hours. The reaction mixture was concentrated under reduced pressure. To the residue were added EtOH (500 mL) and a 1 M aqueous NaOH solution (500 mL), followed by stirring at 80° C. for 24 hours. The reaction mixture was left to be cooled to room temperature, and 1 M hydrochloric acid (500 mL) was added thereto, followed by stirring. The precipitate was collected by filtration, washed with water, and dried by blowing air to obtain 6-cyclohexyl-2-methylthieno[2,3-d]pyrimidin-4(3H)-one (57.0 g).

Preparation Example 13

To a mixture of (6-cyclohexyl-2-methylthieno[2,3-d]pyrimidin-4-yl)methanol (1.28 g) and DCM (20 mL) were added thionyl chloride (1 mL) and DMF (50 µL), followed by stirring at room temperature for 2 hours. The reaction mixture was concentrated under reduced pressure, azeotroped with toluene, and dried. To the residue was added EtOAc. The organic layer was washed sequentially with saturated aqueous sodium bicarbonate and brine. The organic layer was dried over MgSO$_4$ and then concentrated under reduced pressure. The residue was purified by silica gel column (chloroform/EtOAc) to obtain 4-(chloromethyl)-6-cyclohexyl-2-methylthieno[2,3-d]pyrimidine (663 mg).

Preparation Example 14

To a mixture of 4-chloro-6-cyclohexyl-2-methylthieno[2,3-d]pyrimidine (1.0 g) and DMF (40 mL) were added (E)-1-ethoxyethene-2-boronic acid pinacol ester (900 mg) and K$_3$PO$_4$ (4.3 g), and Pd(PPh$_3$)$_4$ (500 mg) was added thereto under an argon atmosphere, followed by heating and stirring at 85° C. for 2 hours. To the reaction mixture was added water, followed by extraction with EtOAc. The organic layer was washed with brine, dried over Na$_2$SO$_4$, then concentrated under reduced pressure, and purified by silica gel column (hexane/EtOAc) to obtain 6-cyclohexyl-4-[(E)-2-ethoxyvinyl]-2-methylthieno[2,3-d]pyrimidine (885 mg).

Preparation Example 15

To tert-butyl 4-{[6-(4,4-dimethylcyclohexyl)-2-methylthieno[2,3-d]pyrimidin-4-yl]methyl}-3,3-dimethylpiperazine-1-carboxylate (645 mg) and dioxane (6.45 mL) was added 4 M HCl/EtOAc (1.66 mL), followed by stirring at room temperature for 1 hour. The reaction mixture was concentrated under reduced pressure. To the residue was added EtOAc, followed by stirring. The precipitate was filtered and dried under reduced pressure to obtain 6-(4,4-dimethylcyclohexyl)-4-[(2,2-dimethylpiperazin-1-yl)methyl]-2-methylthieno[2,3-d]pyrimidine (422 mg).

Preparation Example 15-1

To tert-butyl (1S,4S)-5-{[2-(4,4-dimethylcyclohexyl)-5-methyl[1,3]thiazolo[5,4-d]pyrimidin-7-yl]methyl}-2,5-diazabicyclo[2.2.1]heptane-2-carboxylate (476 mg) and DCM (10 mL) was added trifluoroacetic acid (2.0 mL), followed by stirring at room temperature for 2 hours. To the reaction mixture was added saturated aqueous sodium bicarbonate, followed by extraction with EtOAc. The organic layer was washed with brine, dried over Na$_2$SO$_4$, and then concentrated under reduced pressure. The residue was purified by silica gel column to obtain 7-[(1S,4S)-2,5-diazabicyclo[2.2.1]hept-2-ylmethyl]-2-(4,4-dimethylcyclohexyl)-5-methyl[1,3]thiazolo[5,4-d]pyrimidine (332 mg).

Preparation Example 16

To a mixture of 6-cyclohexyl-4-[(E)-2-ethoxyvinyl]-2-methylthieno[2,3-d]pyrimidine (300 mg) and THF (3 mL) was added 1 M hydrochloric acid (3 mL), followed by stirring at room temperature for 30 minutes. To the reaction mixture was added saturated aqueous sodium bicarbonate to adjust the pH to 8 to 9, followed by extraction with EtOAc. The organic layer was washed with brine, dried over Na$_2$SO$_4$, and then concentrated under reduced pressure. The residue was purified by silica gel column (chloroform/MeOH) to obtain (Z)-2-(6-cyclohexyl-2-methylthieno[2,3-d]pyrimidin-4-yl)ethenol (248 mg).

Preparation Example 17

To a mixture of (Z)-2-(6-cyclohexyl-2-methylthieno[2,3-d]pyrimidin-4-yl)ethenol (430 mg) and MeOH (10 mL) was added NaBH$_4$ (65 mg) in small divided portions, followed by stirring for 15 minutes. To the reaction mixture was added water, followed by extraction with EtOAc. The organic layer was washed sequentially with a saturated aqueous NH$_4$Cl solution and brine, and dried over Na$_2$SO$_4$, and the residue was purified by silica gel column (hexane/EtOAc) to obtain 2-(6-cyclohexyl-2-methylthieno[2,3-d]pyrimidin-4-yl)ethanol (315 mg).

Preparation Example 18

To a mixture of ethyl 6-(4,4-dimethylcyclohexyl)-2-methylthieno[2,3-d]pyrimidine-4-carboxylate (1.0 g) and EtOH (10 mL) was added a 1 M aqueous NaOH solution (3.9 mL) under ice-cooling, followed by stirring at the same temperature for 1 hour. The reaction mixture was concentrated under reduced pressure, and 1 M hydrochloric acid was added thereto, followed by stirring for 30 minutes. The precipitate was collected by filtration, washed with water and then with hexane, dried by flowing air, and then dried under reduced pressure to obtain 6-(4,4-dimethylcyclohexyl)-2-methylthieno[2,3-d]pyrimidine-4-carboxylic acid (900 mg).

Preparation Example 19

To a mixture of [2-(4,4-dimethylcyclohexyl)-5-methyl[1,3]thiazolo[5,4-d]pyrimidin-7-yl]methanol (500 mg) and DCM (10 mL) was added Dess-Martin periodinane (1.46 g) under ice-cooling, followed by stirring at 0° C. for 3 hours. To the reaction mixture was added an aqueous Na$_2$S$_2$O$_3$ solution, followed by extraction with DCM. The organic layer was washed sequentially with saturated aqueous sodium bicarbonate and brine, dried over Na$_2$SO$_4$, and then concentrated under reduced pressure to obtain 2-(4,4-dimethylcyclohexyl)-5-methyl[1,3]thiazolo[5,4-d]pyrimidine-7-carbaldehyde (492 mg). To a mixture of the obtained aldehyde, NaH$_2$PO$_4$ (245 mg), 2-methyl-2-butene (542 μL), water (5 mL), and acetone (10 mL) was added NaClO$_2$ (231 mg) under ice-cooling, followed by stirring at room temperature for 1 hour. To the reaction mixture were added an aqueous Na$_2$S$_2$O$_3$ solution and Na$_2$SO$_4$, followed by extraction with a mixed solution (1:9) of 2-propanol and chloroform. The organic layer was dried over Na$_2$SO$_4$ and then concentrated under reduced pressure to obtain 2-(4,4-dimethylcyclohexyl)-5-methyl[1,3]thiazolo[5,4-d]pyrimidine-7-carboxylic acid (870 mg).

Preparation Example 20

To a mixture of 4-chloro-6-(4,4-dimethylcyclohexyl)-2-methylthieno[2,3-d]pyrimidine (1.0 g), tributyl(1-ethoxyvinyl)stannane (1.16 mL), and toluene (10.8 mL) was added Pd(PPh$_3$)$_4$ (392 mg), followed by heating to reflux for 5 hours. The reaction mixture was left to be cooled to room temperature, and to the reaction mixture were added a saturated aqueous NH$_4$Cl solution, followed by extraction with EtOAc. The organic layer was washed sequentially with water and brine, dried over MgSO$_4$, and then concentrated under reduced pressure to obtain a crude product (1.12 g) containing 6-(4,4-dimethylcyclohexyl)-4-(1-ethoxyvinyl)-2-methylthieno[2,3-d]pyrimidine. To this crude product were added EtOH (9.0 mL) and 1 M hydrochloric acid (10.2 mL) at room temperature, followed by stirring at 50° C. overnight. The reaction mixture was left to be cooled and concentrated under reduced pressure. To the residue was added water, followed by extraction with EtOAc. The organic layer was washed with brine, dried over MgSO$_4$, and then concentrated under reduced pressure. The residue was purified by silica gel column to obtain 1-[6-(4,4-dimethylcyclohexyl)-2-methylthieno[2,3-d]pyrimidin-4-yl]ethanone (820 mg).

Preparation Example 22

A mixed solution of MeOH (2 mL) and THF (15 mL) was cooled in an ice bath, and NaH (60% oil, 600 mg) was added thereto, followed by stirring for 15 minutes. Then, a solution of 6-bromo-4-chloro-2-methylthieno[2,3-d]pyrimidine (2.0 g) in THF (5 mL) was added thereto, followed by stirring at room temperature for 2 hours. To the reaction mixture was added water, followed by extraction with EtOAc. The organic layer was washed with brine, dried over Na$_2$SO$_4$, and then concentrated under reduced pressure. The residue was purified by silica gel column (hexane/EtOAc) to obtain 6-bromo-4-methoxy-2-methylthieno[2,3-d]pyrimidine (1.8 g).

Preparation Example 23

To a mixture of 2-methylthieno[2,3-d]pyrimidin-4(3H)-one (5.0 g) and AcOH (50 mL) was added NCS (4.8 g), followed by heating and stirring at 40° C. for 2 days. The reaction mixture was concentrated under reduced pressure. To the residue was added water, followed by stirring, and the precipitate was collected by filtration and then dried to obtain 6-chloro-2-methylthieno[2,3-d]pyrimidin-4(3H)-one (5.5 g).

Preparation Example 24

To a mixture of 4-chloro-6-cyclohexyl-2-methylthieno[2,3-d]pyrimidine (27.3 g), DABCO (1.2 g) and DMSO (150 mL) was slowly added an aqueous solution (14 mL) of KCN (8 g), followed by stirring at room temperature for 15 hours. To the reaction mixture was added water (150 mL) under ice-cooling, followed by stirring. The precipitate was collected by filtration and dissolved in chloroform. To the organic layer were added MgSO$_4$, activated carbon (2 g), and basic silica gel (100 mL), followed by stirring. The mixture was filtered through Celite and then concentrated under reduced pressure to obtain 6-cyclohexyl-2-methylthieno[2,3-d]pyrimidine-4-carbonitrile (23.7 g).

Preparation Example 25

Under an argon atmosphere, to DME (12.5 mL) that had been ice-cooled was added NaH (60% oil, 203 mg), followed by stirring for 10 minutes. To this mixture was added dropwise a solution of ethyl 3-(1,1-dioxidothiomorpholin-4-yl)-3-oxopropanoate (1.40 g) in DME (10 mL), followed by stirring at the same temperature for 30 minutes. Then, 4-chloro-6-(4,4-dimethylcyclohexyl)-2-methylthieno[2,3-d]pyrimidine (750 mg) was added thereto, followed by stirring at 60° C. overnight. The reaction mixture was left to be cooled, and then a saturated aqueous NH$_4$Cl solution was added thereto, followed by extraction with EtOAc. The organic layer was washed sequentially with water and brine, dried over MgSO$_4$, and then concentrated under reduced pressure. The residue was purified by silica gel column to obtain ethyl 2-[6-(4,4-dimethylcyclohexyl)-2-methylthieno[2,3-d]pyrimidin-4-yl]-3-(1,1-dioxidothiomorpholin-4-yl)-3-oxopropanoate (559 mg).

Preparation Example 28

To a mixture of 6-bromo-4-[(1,1-dioxidothiomorpholin-4-yl)methyl]-2-methylthieno[2,3-d]pyrimidine (200 mg), 4,4, 5,5-tetramethyl-2-(spiro[2.5]octa-5-en-6-yl)-1,3,2-dioxaborolane (185 mg), and dioxane (4 mL) were added Pd$_2$dba$_3$ (25 mg), dicyclohexyl (2',4',6'-triisopropylbiphenyl-2-yl) phosphine (50 mg), K$_3$PO$_4$ (340 mg), and water (200 μL), followed by heating and stirring at 100° C. overnight. The reaction mixture was cooled to room temperature, and water was added thereto, followed by extraction with EtOAc. The organic layer was dried over MgSO$_4$, and then concentrated under reduced pressure. The residue was purified by a basic silica gel column (hexane/EtOAc) to obtain 4-[(1,1-dioxidothiomorpholin-4-yl)methyl]-2-methyl-6-(spiro[2.5]octa-5-en-6-yl)thieno[2,3-d]pyrimidine (167 mg).

Preparation Example 31

To a mixture of N-[(6-cyclohexyl-2-methylthieno[2,3-d]pyrimidin-4-yl)methyl]cycloheptaneamine (132 mg) and CH$_3$CN (3 mL) were added CH$_3$I (100 μL) and DIPEA (200 μL), followed by stirring at room temperature for 15 hours. To the reaction mixture was added water, followed by extraction with EtOAc. The organic layer was dried over MgSO$_4$ and then concentrated under reduced pressure. The residue was purified by silica gel column (hexane/EtOAc) to obtain N-[(6-cyclohexyl-2-methylthieno[2,3-d]pyrimidin-4-yl)methyl]-N-methylcycloheptaneamine (77 mg).

Preparation Example 32

To a mixture of N-{[6-(4,4-dimethylcyclohexyl)-2-methylthieno[2,3-d]pyrimidin-4-yl]methyl}cyclopentaneamine (128 mg) and DMF (3 mL) were added 3-bromopropan-1-ol (100 μL) and Na$_2$CO$_3$ (110 mg), followed by stirring at 100° C. for 15 hours. The reaction mixture was cooled to room temperature and then water was added thereto, followed by extraction with EtOAc. The organic layer was dried over MgSO$_4$ and then concentrated under reduced pressure. The residue was purified by basic silica gel column (hexane/EtOAc) to obtain 3-(cyclopentyl{[6-(4,4-dimethylcyclohexyl)-2-methylthieno[2,3-d]pyrimidin-4-yl]methyl}amino)propan-1-ol (88 mg).

Preparation Example 33

To a mixture of (6-cyclohexyl-2-methylthieno[2,3-d]pyrimidin-4-yl)methyl methanesulfonate (500 mg) and CH$_3$CN (10 mL) was added cyclopentylamine (1.0 mL), followed by stirring at room temperature for 3 hours. To the reaction mixture was added water, followed by extraction with EtOAc. The organic layer was dried over MgSO$_4$ and then concentrated under reduced pressure. The residue was purified by basic silica gel column (hexane/EtOAc) and silica gel column (hexane/EtOAc) to obtain N-[(6-cyclohexyl-2-methylthieno[2,3-d]pyrimidin-4-yl)methyl]cyclopentaneamine (326 mg).

Preparation Example 34

To a mixture of (6-cyclohexyl-2-methylthieno[2,3-d]pyrimidin-4-yl]methyl methanesulfonate (150 mg), cyclopentylmethylamine (100 mg), and CH$_3$CN (3 mL) was added DIPEA (200 μL), followed by stirring at room temperature overnight. To the reaction mixture was added saturated aqueous sodium bicarbonate, followed by extraction with EtOAc. The organic layer was washed with brine, dried over MgSO$_4$, and then concentrated under reduced pressure, and the residue was purified by silica gel column (hexane/EtOAc) to obtain N-[(6-cyclohexyl-2-methylthieno[2,3-d]pyrimidin-4-yl)methyl]-N-methylcyclopentaneamine (131 mg).

Preparation Example 37

To a mixture of (4,4-dimethylcyclohexyl)acetaldehyde (27.3 g) and DMF (100 mL) were added 2-cyanoacetamide (12 g), sulfur (5 g), and TEA (24 mL), followed by heating and stirring at 60° C. for 12 hours. To the reaction mixture was added water, followed by extraction with EtOAc. The organic layer was washed sequentially with water and brine, and then Na$_2$SO$_4$ and activated carbon (2 g) were added thereto, followed by stirring. The mixture was filtered through Celite and then concentrated under reduced pressure to obtain 2-amino-5-(4,4-dimethylcyclohexyl)thiophene-3-carboxamide (33.0 g).

Preparation Example 38

To a mixture of 2-amino-5-(4,4-dimethylcyclohexyl) thiophene-3-carboxamide (33 g), pyridine (40 mL), and DCM (200 mL) was added dropwise acetyl chloride (14 mL) at 0° C., followed by stirring at room temperature for 1.5 hours. The reaction mixture was concentrated under reduced pressure, and then water and 1 M hydrochloric acid were added thereto, followed by extraction with chloroform. The organic layer was washed sequentially with water, saturated aqueous sodium bicarbonate, and brine. To the organic layer were added MgSO$_4$, activated carbon (2 g), and basic silica gel (100 mL), followed by stirring. The mixture was filtered through Celite and then concentrated under reduced pressure to obtain 2-acetamide-5-(4,4-dimethylcyclohexyl) thiophene-3-carboxamide (37.3 g).

Preparation Example 39

To a mixture of WSC hydrochloride (4.5 g), HOBt (3.2 g), and DMF (50 mL) were added difluoroacetic acid (2 mL) and 2-amino-5-cyclohexylthiophene-3-carboxamide (5.0 g), followed by stirring at room temperature for 3 days. To the reaction mixture was added 50% brine, followed by extraction with EtOAc. The organic layer was washed sequentially with saturated aqueous sodium bicarbonate, water, and brine. To the organic layer were added MgSO$_4$, and basic silica gel was added thereto, followed by stirring. The mixture was filtered through Celite and then concentrated under reduced pressure to obtain 5-cyclohexyl-2-[(difluoroacetyl)amino] thiophene-3-carboxamide (7.0 g).

Preparation Example 40

To a mixture of 4,4-dimethylcyclohexane carboxylic acid (20.4 g) and toluene (150 mL) was added thionyl chloride (19 mL), followed by stirring at 80° C. for 15 hours. The reaction liquid was concentrated under reduced pressure. To the residue was added 4,6-dichloro-2-methylpyrimidine-5-amine (23.3 g), followed by stirring at 90° C. for 10 minutes. DCE (207 mL) was added thereto, followed by stirring at 100° C. for 15 hours. The reaction mixture was cooled to room temperature, and then water was added thereto, followed by extraction with chloroform. The organic layer was dried over MgSO$_4$ and then concentrated under reduced pressure. The residue was purified by silica gel column (hexane/EtOAc) to obtain N-(4,6-dichloro-2-methylpyrimidin-5-yl)-4,4-dimethylcyclohexanecarboxamide (23.8 g).

Preparation Example 41

To a mixture of adamanthane-1-carboxylic acid (2.43 g) and DCM (40 mL) was added 1-chloro-N,N,2-trimethylpropenylamine (2.23 mL) at room temperature, followed by stirring for 1 hour. To this mixture were added 4,6-dichloro-2-methylpyrimidine-5-amine (2.0 g) and pyridine (2.71 mL), followed by stirring at room temperature for additional 1 hour. To the reaction mixture was added water, followed by extraction with EtOAc. The organic layer was washed with brine, dried over MgSO$_4$, and then concentrated under reduced pressure. The residue was purified by silica gel column to obtain N-(4,6-dichloro-2-methylpyrimidin-5-yl)adamanthane-1-carboxamide (3.51 g).

Preparation Example 42

To a mixture of thiomorpholine-1,1-dioxide (3.22 g) and DCM (48 mL) was added ethyl 3-chloro-3-oxopropanoate (2.0 mL) under ice-cooling, followed by stirring at the same temperature for 30 minutes. To the reaction mixture was added water, followed by extraction with chloroform. The organic layer was washed with brine, dried over MgSO$_4$, and then concentrated under reduced pressure to obtain a crude product (3.11 g) of ethyl 3-(1,1-dioxidothiomorpholin-4-yl)-3-oxopropanoate. The crude product was used as it was for the next reaction without purification.

Preparation Example 43

Under an argon atmosphere, to a mixture of 2-(4,4-dimethylcyclohexyl)ethanol (25.3 g) and DCM (200 mL) were added DMSO (50 mL) and TEA (100 mL), and a sulfur trioxide-pyridine complex (77.7 g) was added in small divided portions while maintaining the inner temperature to 10° C. or lower under ice-cooling. After stirring at room temperature for 2 hours, to the reaction mixture was added ice water, followed by concentration under reduced pressure and then extraction with chloroform. The organic layer was washed sequentially with 1 M hydrochloric acid and brine. To the organic layer was added MgSO$_4$, followed by stirring. Then, the mixture was filtered and concentrated under reduced pressure to obtain (4,4-dimethylcyclohexyl)acetaldehyde (27.3 g).

Preparation Example 44

To a mixture of ethyl 1-(3-ethoxy-3-oxopropanoyl)piperidin-4-yl malonate (1.02 g) and EtOH (5.1 mL) was added NaOEt (20% EtOH solution, 105 mg), followed by stirring at room temperature for 30 minutes. To the reaction mixture was added a saturated aqueous NH$_4$Cl solution, followed by extraction with EtOAc. The organic layer was washed with brine, dried over Na$_2$SO$_4$, and then concentrated under reduced pressure. The residue was purified by silica gel column to obtain ethyl 3-(4-hydroxypiperidin-1-yl)-3-oxopropanpate (368 mg).

Preparation Example 45

To a mixture of a 30% hydrogen peroxide solution (2.7 mL) and DCM (100 mL) was added dropwise trifluoroacetate anhydride (4.4 mL) under ice-cooling, and a solution of 1-benzyl-5-methyl-1,2,3,6-tetrahydropyridine (2.1 g) in DCM (5 mL) was added thereto, followed by stirring for 1.5 hours. To the reaction mixture was added a saturated aqueous Na$_2$SO$_3$ solution, followed by extraction with DCM. The organic layer was washed with saturated aqueous sodium bicarbonate, dried over MgSO$_4$, and then concentrated under reduced pressure. The residue was purified by silica gel column (chloroform/MeOH) to obtain trans-1-benzyl-3-methylpiperidine-3,4-diol (2.0 g).

Preparation Example 46

To a solution of 5-benzyl-2,5-diazabicyclo[2.2.2]octan-3-one (400 mg) in EtOH (5 mL) was added 20% Pd(OH)$_2$/C (65 mg), followed by stirring at room temperature overnight at normal pressure under a hydrogen atmosphere. The reaction mixture was filtered through Celite and then concentrated under reduced pressure to obtain 2,5-diazabicyclo[2.2.2]octan-3-one (219 mg).

Preparation Example 47

A mixture of a trans-1-benzyl-4-methylpiperidine-3,4-diolacetate (256 mg), 10% Pd/C (193 mg), acetic acid (5 mL), and EtOH (5 mL) was stirred at room temperature for 12 hours under a hydrogen atmosphere of 3 atm. The reaction mixture was filtered through Celite and then concentrated under reduced pressure to obtain trans-4-methylpiperidine-3,4-diol acetate (212 mg), which was used for the next reaction without purification.

Preparation Example 48

Under a hydrogen atmosphere of 3 atm, a mixture of trans-1-benzyl-3-methylpiperidine-3,4-diol (460 mg), DIBOC (907 mg), 20% Pd(OH)$_2$/C (291 mg), and EtOAc (28 mL) was stirred at room temperature for 12 hours. The reaction mixture was filtered through Celite and then concentrated under reduced pressure to obtain tert-butyl trans-3,4-dihydroxy-3-methylpiperidine-1-carboxylate (80 mg).

Preparation Example 49

To a mixture of 10% Pd/C (409 mg) and MeOH (7 mL) was added a mixture of ammonium formate (2.92 g) and 1-(diphenylmethyl)-2,2-dimethylazetidin-3-ol (1.03 g) in MeOH (7 mL) and THF (14 mL), followed by stirring at 50° C. for 2 hours. The reaction mixture was cooled to room temperature and then concentrated under reduced pressure. The residue was purified by basic silica gel column (chloroform/MeOH) to obtain 2,2-dimethylazetidin-3-ol (378 mg).

Preparation Example 50

To a mixture of a 30% hydrogen peroxide solution (3.6 mL) and DCM (120 mL) were added trifluoroacetic anhydride (6.0 mL) at 0° C., and a solution of 1-benzyl-4-methyl-1,2,3,6-tetrahydropyridine (2.9 g) in DCM (10 mL) was further added thereto, followed by stirring at room temperature for 12 hours and then stirring at 50° C. for additional 3 hours. To the reaction mixture was added an aqueous Na$_2$SO$_3$ solution, followed by stirring until peroxides disappeared, and then extracting with DCM. The organic layer was washed with saturated aqueous sodium bicarbonate, dried over MgSO$_4$, and then concentrated under reduced pressure. The residue was purified by silica gel column (chloroform/MeOH) to obtain 3-benzyl-6-methyl-7-oxa-3-azabicyclo[4.1.0]heptane (1.8 g).

Preparation Example 51

To a mixture of 3-benzyl-6-methyl-7-oxa-3-azabicyclo[4.1.0]heptane (700 mg) in THF (10 mL) was added AcOH (10 mL), followed by stirring at 80° C. for 2 hours. The reaction mixture was concentrated under reduced pressure. The residue was purified by silica gel column (chloroform/MeOH) to obtain trans-1-benzyl-4-methylpiperidine-3,4-diolacetate (256 mg).

Preparation Example 52

To a mixture of tert-butyl trans-3,4-dihydroxy-3-methylpiperidine-1-carboxylate (80 mg) and EtOAc (5 mL) was added 4 M HCl/EtOAc (0.4 mL) at room temperature, followed by stirring for 12 hours. The reaction mixture was concentrated under reduced pressure to obtain trans-3-methylpiperidine-3,4-diol hydrochloride (50 mg).

Example 1

To a mixture of thiomorpholine-1,1-dioxide (65 mg) and DMF (4 mL) were added (6-cyclohexyl-2-methylthieno[2,3-d]pyrimidin-4-yl)methyl methanesulfonate (110 mg) and TEA (150 µL), followed by stirring at room temperature for 24 hours. To the reaction mixture was added water, followed by extraction with EtOAc. The organic layer was washed with brine, dried over $Na_2SO_4$, and then concentrated under reduced pressure. The residue was purified by basic silica gel column (hexane/EtOAc) to obtain 6-cyclohexyl-4-[(1,1-dioxidothiomorpholin-4-yl)methyl]-2-methylthieno[2,3-d]pyrimidine (94 mg).

Example 2

To a mixture of thiomorpholine-1,1-dioxide (70 mg) and DMF (4 mL) were added [6-(4,4-dimethylcyclohexyl)-2-methylthieno[2,3-d]pyrimidin-4-yl]methyl methanesulfonate (120 mg) and TEA (150 µL), followed by stirring at room temperature overnight. To the reaction mixture was added water, followed by extraction with EtOAc. The organic layer was washed with brine, dried over $MgSO_4$, and then concentrated under reduced pressure. The residue was purified by basic silica gel column (hexane/EtOAc) to obtain 6-(4,4-dimethylcyclohexyl)-4-[(1,1-dioxidothiomorpholin-4-yl)methyl]-2-methylthieno[2,3-d]pyrimidine (102 mg).

Example 31, Example 31-1

A racemic compound of trans-1-{[6-(4,4-dimethylcyclohexyl)-2-methylthieno[2,3-d]pyrimidin-4-yl]methyl}piperidine-3,4-diol (321 mg) was purified by supercritical fluid chromatography (column: manufactured by Daicel Corporation, Chiralpak IC 10×250 mm, mobile phase: liquid carbon dioxide gas/0.1% diethylamine-containing MeOH=75/25, flow rate of 10 mL/min, column temperature: 40° C.). To the residue was added IPE, followed by stirring, and then the precipitate was collected by filtration to obtain optically active trans-1-{[6-(4,4-dimethylcyclohexyl)-2-methylthieno[2,3-d]pyrimidin-4-yl]methyl}piperidine-3,4-diol (110 mg) having a retention time of 8.48 minutes and optically active trans-1-{[6-(4,4-dimethylcyclohexyl)-2-methylthieno[2,3-d]pyrimidin-4-yl]methyl}piperidine-3,4-diol (112 mg) having a retention time of 9.44 minutes, respectively.

Example 33

To a mixture of 6-cyclohexyl-4-[(2,2-dimethylmorpholin-4-yl)methyl]-2-methylthieno[2,3-d]pyrimidine (130 mg) and EtOAc (2 mL) was added 4 M HCl/EtOAc (100 µL), followed by stirring at room temperature. The precipitated solid was collected by filtration to obtain 6-cyclohexyl-4-[(2,2-dimethylmorpholin-4-yl)methyl]-2-methylthieno[2,3-d]pyrimidine hydrochloride (90 mg).

Example 52

To a mixture of [6-(4,4-dimethylcyclohexyl)-2-methylthieno[2,3-d]pyrimidin-4-yl]methyl methanesulfonate (120 mg) and DMF (4 mL) were added piperidin-4-ol (70 mg) and TEA (100 µL), followed by stirring at room temperature for 18 hours. To the reaction mixture was added water, followed by extraction with EtOAc. The organic layer was washed with saturated aqueous sodium bicarbonate and brine, dried over $Na_2SO_4$, and then concentrated under reduced pressure. The residue was purified by basic silica gel column (hexane/EtOAc). To the obtained purified product was added EtOAc, and then 4 M HCl/EtOAc (100 µL) was added thereto, followed by stirring at room temperature. The precipitate was collected by filtration to obtain 1-{[6-(4,4-dimethylcyclohexyl)-2-methylthieno[2,3-d]pyrimidin-4-yl]methyl}piperidin-4-ol hydrochloride (115 mg).

Example 85

A suspension of [6-(4,4-dimethylcyclohexyl)-2-methylthieno[2,3-d]pyrimidin-4-yl]methyl methanesulfonate (100 mg), cis-pyrrolidine-3,4-diol hydrochloride (57 mg), and $K_2CO_3$ (75 mg) in DMF (3 mL) was stirred at 50° C. for 12 hours. The reaction mixture was cooled to room temperature, and water was added thereto, followed by extraction with EtOAc. The organic layer was dried over $MgSO_4$ and then concentrated under reduced pressure. The residue was purified by silica gel column (chloroform/MeOH). The obtained purified product was suspended in IPE, and the precipitate was collected by filtration to obtain cis-1-{[6-(4,4-dimethylcyclohexyl)-2-methylthieno[2,3-d]pyrimidin-4-yl]methyl}pyrrolidine-3,4-diol (9 mg).

Example 96

A suspension of [6-(4,4-dimethylcyclohexyl)-2-methylthieno[2,3-d]pyrimidin-4-yl]methyl methanesulfonate (100 mg), 2-(azetidin-3-yl)propan-2-ol hydrochloride (62 mg) and $K_2CO_3$ (94 mg) in DMF (1.0 mL) was stirred at 70° C. for 12 hours. The reaction mixture was cooled to room temperature, and water was added thereto, followed by extraction with EtOAc. The organic layer was dried over $MgSO_4$ and then concentrated under reduced pressure. The residue was purified by silica gel column (chloroform/MeOH) to form a salt with 4 M HCl/EtOAc, and then washed with EtOAc to obtain 2-(1-{[6-(4,4-dimethylcyclohexyl)-2-methylthieno[2,3-d]pyrimidin-4-yl]methyl}azetidin-3-yl)propan-2-ol hydrochloride (32 mg).

Example 105

To a mixture of 5-[(6-cyclohexyl-2-methylthieno[2,3-d]pyrimidin-4-yl)methyl]-2,5-diazabicyclo[2.2.2]octan-3-one (113 mg) and DMF was added NaH (60% oil, 12 mg) under ice-cooling, followed by stirring at the same temperature for 5 minutes, and $CH_3I$ (38 µL) was added thereto, followed by stirring at the same temperature for 20 minutes. To the reaction mixture was added water, followed by extraction with EtOAc. The organic layer was washed sequentially with water and brine, dried over $MgSO_4$, and then concentrated under reduced pressure. The residue was purified by basic silica gel column (hexane/EtOAc). The residue was dissolved in EtOAc, and an excess amount of 4 M HCl/EtOAc was added thereto, followed by concentration under reduced pressure. To the obtained purified product was added Et$_2$O, followed by stirring, and the precipitate was collected by filtration to obtain 5-[(6-cyclohexyl-2-methylthieno[2,3-d]pyrimidin-4-yl)methyl]-2-methyl-2,5-diazabicyclo[2.2.2]octan-3-one hydrochloride (83 mg).

Example 106

To a mixture of (Z)-2-(6-cyclohexyl-2-methylthieno[2,3-d]pyrimidin-4-yl)ethenol (120 mg) and AcOH (12 mL) were added morpholine (400 μL) and NaBH(OAc)$_3$ (200 mg), followed by stirring at room temperature for 15 hours. To the reaction mixture was added saturated aqueous sodium bicarbonate, followed by extraction with chloroform. The organic layer was washed with brine, dried over Na$_2$SO$_4$, and then concentrated under reduced pressure. The residue was purified by basic silica gel column (hexane/EtOAc) to obtain 6-cyclohexyl-2-methyl-4-[2-(morpholin-4-yl)ethyl]thieno[2,3-d]pyrimidine (53 mg).

Example 107

To a mixture of 2-[(6-cyclohexyl-2-methylthieno[2,3-d]pyrimidin-4-yl)methyl]-2,5-diazabicyclo[2.2.2]octan-3-one (67 mg), 1H-benzotriazole-1-methanol (54 mg), and DCE was added NaBH(OAc)$_3$ (115 mg) at room temperature, followed by stirring at the same temperature for 5 hours. To the reaction mixture was added water, followed by extraction with EtOAc. The organic layer was washed with brine, dried over Na$_2$SO$_4$, and then concentrated under reduced pressure. The residue was purified by basic silica gel column (hexane/EtOAc) and the obtained purified product was dissolved in EtOAc. An excess amount of 4 M HCl/EtOAc was added thereto, followed by concentration under reduced pressure. To the residue was added Et$_2$O, followed by stirring, and the precipitate was collected by filtration to obtain 2-[(6-cyclohexyl-2-methylthieno[2,3-d]pyrimidin-4-yl)methyl]-5-methyl-2,5-diazabicyclo[2.2.2]octan-3-one hydrochloride (57 mg).

Example 108

A mixture of 4-[(1,1-dioxidothiomorpholin-4-yl)methyl]-2-methyl-6-(spiro[2.5]octa-5-en-6-yl)thieno[2,3-d]pyrimidine (165 mg), THF (5 mL), and EtOH (5 mL) was allowed to undergo a reaction using H-Cube (registered trademark, 10% Pd/C cartridge, Thalesnano) at 50 bar and 50° C. under a H$_2$ atmosphere. The reaction mixture was concentrated under reduced pressure. The residue was purified by silica gel column chromatorgraphy (chloroform/MeOH) to obtain 4-[(1,1-dioxidothiomorpholin-4-yl)methyl]-2-methyl-6-(spiro[2.5]octa-6-yl)thieno[2,3-d]pyrimidine (59 mg).

Example 109

To a mixture of {(3S)-4-[(6-cyclohexyl-2-methylthieno[2,3-d]pyrimidin-4-yl)methyl]morpholin-3-yl}methanol (132 mg) and DMF was added NaH (60% oil, 15 mg) under ice-cooling, followed by stirring at the same temperature for 5 minutes, and then CH$_3$I (17 μL) was added thereto, followed by stirring at the same temperature for 30 minutes. To the reaction mixture was added water, followed by extraction with EtOAc. The organic layer was washed with brine, then dried over Na$_2$SO$_4$, and concentrated under reduced pressure.

The residue was purified by basic silica gel column (hexane/EtOAc) to obtain 6-cyclohexyl-4-{[(3S)-3-(methoxymethyl)morpholin-4-yl]methyl}-2-methylthieno[2,3-d]pyrimidine (102 mg).

Example 112

To a mixture of piperidin-2-one (100 mg), THF (4 mL), and DMF (1 mL) was added NaH (60% oil, 40 mg), followed by stirring at room temperature for 30 minutes, and then (6-cyclohexyl-2-methylthieno[2,3-d]pyrimidin-4-yl)methyl methanesulfonate (150 mg) was added thereto, followed by further stirring at room temperature for 1 hour. To the reaction mixture were added water and 1 M hydrochloric acid, followed by extraction with EtOAc. The organic layer was washed with brine, dried over MgSO$_4$, and then concentrated under reduced pressure. The residue was purified by silica gel column (hexane/EtOAc) to obtain 1-[(6-cyclohexyl-2-methylthieno[2,3-d]pyrimidin-4-yl)methyl]piperidin-2-one (13 mg).

Example 116

To a mixture of (6-cyclohexyl-2-methylthieno[2,3-d]pyrimidin-4-yl)methyl methanesulfonate (130 mg) and CH$_3$CN (5 mL) were added 3-fluoropiperidinehydrochloride (107 mg) and TEA (200 μL), followed by stirring at room temperature for 15 hours. To the reaction mixture was added water, followed by extraction with EtOAc. The organic layer was washed with brine, dried over Na$_2$SO$_4$, and then concentrated under reduced pressure. The residue was purified by basic silica gel column (hexane/EtOAc). To the obtained purified product were added EtOH and fumaric acid (35 mg), followed by dissolving therein and concentrating under reduced pressure. To the residue was added EtOH:acetone (1:5), followed by heating and dissolving therein, and leaving to be cooled under stirring. The precipitate was collected by filtration to obtain 6-cyclohexyl-4-[(3-fluoropiperidin-1-yl)methyl]-2-methylthieno[2,3-d]pyrimidine fumarate (105 mg).

Example 126

A mixture of [6-(4,4-dimethylcyclohexyl)-2-methylthieno[2,3-d]pyrimidin-4-yl]methyl methanesulfonate (100 mg), 2-oxa-6-azaspiro[3.3]heptaneoxalate (67 mg), K$_2$CO$_3$ (94 mg), and DMF (1.0 mL) was stirred at 80° C. for 12 hours. The reaction mixture was cooled to room temperature, and water was added thereto, followed by extraction with EtOAc. The organic layer was dried over MgSO$_4$ and then concentrated under reduced pressure. The residue was purified by silica gel column (chloroform/MeOH), and fumaric acid (10 mg) was added thereto to form a salt, followed by washing with EtOAc, thereby obtaining 6-(4,4-dimethylcyclohexyl)-2-methyl-4-(2-oxa-6-azaspiro[3.3]hept-6-ylmethy)thieno[2,3-d]pyrimidinefumarate (23 mg).

Example 130

To a mixture of 2-(6-cyclohexyl-2-methylthieno[2,3-d]pyrimidin-4-yl)ethyl methanesulfonate (64 mg) and CH$_3$CN (2 mL) was slowly added piperidine (800 μL), followed by stirring at room temperature for 3 days. To the reaction mixture was added water, followed by extraction with EtOAc. The organic layer was washed with brine, dried over Na$_2$SO$_4$, and then concentrated under reduced pressure. The residue was purified by basic silica gel column (hexane/EtOAc). To a solution of the obtained purified product in chloroform (3 mL) was added 4 M HCl/EtOAc (150 µL), followed by concentration under reduced pressure. To the residue was added EtOAc, followed by heating and washing, and the precipitate was collected by filtration to obtain 6-cyclohexyl-2-methyl-4-[2-(piperidin-1-yl)ethyl]thieno[2,3-d]pyrimidine dihydrochloride (61 mg).

Example 134

To a mixture of (6-cyclohexyl-2-methylthieno[2,3-d]pyrimidin-4-yl)methyl methanesulfonate (150 mg) and CH$_3$CN (2 mL) was slowly added a solution of (2S)-pyrrolidin-2-ylmethanol (100 mg) in CH$_3$CN (1 mL), followed by stirring at room temperature for 15 hours. To the reaction mixture was added water, followed by extraction with EtOAc. The organic layer was washed with brine, dried over Na$_2$SO$_4$, and then concentrated under reduced pressure. The residue was purified by basic silica gel column (hexane/EtOAc). To the obtained purified product were added EtOH and fumaric acid (39 mg), followed by dissolving therein and concentrating under reduced pressure. To the residue was added EtOH/acetone (1:10), followed by heating and dissolving therein. After leaving to be cooled under stirring, the precipitate was collected by filtration to obtain {(2S)-1-[(6-cyclohexyl-2-methylthieno[2,3-d]pyrimidin-4-yl)methyl]pyrrolidin-2-yl}methanolfumarate (76 mg).

Example 150

To a mixture of 6-(4,4-dimethylcyclohexyl)-2-methylthieno[2,3-d]pyrimidin-4-yl]methyl methanesulfonate (150 mg), DIPEA (209 µL), and DMF (2.25 mL) was added 2,2-dimethylazetidin-3-ol (54 mg), followed by stirring at room temperature for 18 hours. To the reaction mixture were added water and EtOAc, followed by extraction with EtOAc. The organic layer was washed with brine, dried over Na$_2$SO$_4$, and then concentrated under reduced pressure. The residue was purified by silica gel column (hexane/EtOAc). The obtained purified product was dissolved in EtOAc (1.5 mL), and then a mixture of fumaric acid (38 mg) and MeOH (300 µL) was added thereto. The precipitate was collected by filtration to obtain 1-{[6-(4,4-dimethylcyclohexyl)-2-methylthieno[2,3-d]pyrimidin-4-yl]methyl}-2,2-dimethylazetidin-3-ol fumarate (106 mg).

Example 152

To a mixture of 2-{[(6-cyclohexyl-2-methylthieno[2,3-d]pyrimidin-4-yl)methyl]amino}-2-methylpropan-1-ol (55 mg) and DCM was added CDI (40 mg), followed by stirring at room temperature for 6 hours. The reaction mixture was concentrated under reduced pressure. The residue was purified by silica gel column (hexane/EtOAc) to obtain 3-[(6-cyclohexyl-2-methylthieno[2,3-d]pyrimidin-4-yl)methyl]-4,4-dimethyl-1,3-oxazolidin-2-one (54 mg).

Example 153

To a mixture of 6-(4,4-dimethylcyclohexyl)-4-[(2,2-dimethylpiperazin-1-yl)methyl]-2-methylthieno[2,3-d]pyrimidine (40 mg), pyridine (83 µL), and DCM (1.2 mL) was added acetic anhydride (49 µL), followed by stirring at room temperature for 30 minutes. To the reaction mixture was added water, followed by extraction with EtOAc. The organic layer was washed with brine, dried over MgSO$_4$, and then concentrated under reduced pressure. The residue was purified by silica gel column. To a solution of the obtained purified product in EtOAc was added dropwise 4 M HCl/dioxane, and the precipitate was collected by filtration and dried to obtain 1-(4-{[6-(4,4-dimethylcyclohexyl)-2-methylthieno[2,3-d]pyrimidin-4-yl]methyl}-3,3-dimethylpiperazin-1-yl)ethanone hydrochloride (35 mg).

Example 155

To a mixture of 6-(4,4-dimethylcyclohexyl)-4-[(2,2-dimethylpiperazin-1-yl)methyl]-2-methylthieno[2,3-d]pyrimidine (222 mg), glycolic acid (52 mg), and NMP (3.2 mL) were added HATU (306 mg) and DIPEA (492 µL), followed by stirring at room temperature overnight. To the reaction mixture was added a saturated aqueous NH$_4$Cl solution, followed by extraction with EtOAc. The organic layer was washed sequentially with water and brine, dried over MgSO$_4$, and then concentrated under reduced pressure. The residue was purified by silica gel column to obtain 1-(4-{[6-(4,4-dimethylcyclohexyl)-2-methylthieno[2,3-d]pyrimidin-4-yl]methyl}-3,3-dimethylpiperazin-1-yl)-2-hydroxyethanone (102 mg).

Example 161

(3S)-1-{[2-(4,4-Dimethylcyclohexyl)-5-methyl[1,3]thiazolo[5,4-d]pyrimidin-7-yl]methyl}pyrrolidin-3-ol (73 mg) was dissolved in EtOH (3 mL), and fumaric acid (24 mg) was added thereto, followed by concentration under reduced pressure. To the residue was added IPE, followed by stirring at room temperature. The precipitate was collected by filtration to obtain (3S)-1-{[2-(4,4-dimethylcyclohexyl)-5-methyl[1,3]thiazolo[5,4-d]pyrimidin-7-yl]methyl}pyrrolidin-3-ol fumarate (81 mg).

Example 163

To a mixture of 5-benzyl-2-[(6-cyclohexyl-2-methylthieno[2,3-d]pyrimidin-4-yl)methyl]-2,5-diazabicyclo[2.2.2]octan-3-one (140 mg) and DCE (5 mL) was added 1-chloroethyl chloroformate (50 µL), followed by stirring at room temperature overnight. The reaction solution was purified by silica gel column (chloroform/MeOH/saturated aqueous NH$_3$) without concentration. The residue was dissolved in MeOH, and heated to reflux for 30 minutes. The reaction mixture was concentrated under reduced pressure and the residue was purified by silica gel column (chloroform/MeOH/saturated aqueous NH$_3$) to obtain 2-[(6-cyclohexyl-2-methylthieno[2,3-d]pyrimidin-4-yl)methyl]-2,5-diazabicyclo[2.2.2]octan-3-one (87 mg).

Example 187

To a mixture of N-[(6-cyclohexyl-2-methylthieno[2,3-d]pyrimidin-4-yl)methyl]cyclohexaneamine (47 mg) and DCM (4 mL) were added dropwise acetyl chloride (20 µL) and TEA (40 µL) at 0° C., followed by stirring at room temperature for 2.5 hours. To the reaction mixture was added water, followed by extraction with EtOAc. The organic layer was washed sequentially with 1 M hydrochloric acid, saturated aqueous sodium bicarbonate, and brine, dried over MgSO$_4$, and then concentrated under reduced pressure to obtain N-cyclohexyl-N-[(6-cyclohexyl-2-methylthieno[2,3-d]pyrimidin-4-yl)methyl]acetamide (50 mg).

Example 188

To a mixture of N-{[6-(4,4-dimethylcyclohexyl)-2-methylthieno[2,3-d]pyrimidin-4-yl]methyl}tetrahydro-2H-pyran-4-amine (60 mg), pyridine (129 μL), and DCM (1.8 mL) was added acetic anhydride (76 μL), followed by stirring at room temperature for 30 minutes. To the reaction mixture was added water, followed by extraction with EtOAc. The organic layer was washed with brine, dried over $Na_2SO_4$, and then concentrated under reduced pressure. The residue was purified by silica gel column to obtain N-{[6-(4,4-dimethylcyclohexyl)-2-methylthieno[2,3-d]pyrimidin-4-yl]methyl}-N-(tetrahydro-2H-pyran-4-yl)acetamide (23 mg).

Example 190

To a mixture of N-{[6-(4,4-difluorocyclohexyl)-2-methylthieno[2,3-d]pyrimidin-4-yl]methyl}-1-methoxy-2-methylpropan-2-amine (110 mg), 1H-benzotriazole-1-methanol (86 mg), and DCE was added $NaBH(OAc)_3$ (182 mg), followed by stirring at room temperature for 4 hours. To the reaction mixture was added water, followed by extraction with EtOAc. The organic layer was washed with brine, dried over $Na_2SO_4$, and then concentrated under reduced pressure. The residue was purified by basic silica gel column (hexane/EtOAc) to obtain N-{[6-(4,4-difluorocyclohexyl)-2-methylthieno[2,3-d]pyrimidin-4-yl]methyl}-1-methoxy-N,2-dimethylpropan-2-amine (93 mg). This product was dissolved in MeOH, and fumaric acid (27 mg) was added thereto, followed by concentration under reduced pressure to obtain N-{[6-(4,4-difluorocyclohexyl)-2-methylthieno[2,3-d]pyrimidin-4-yl]methyl}-1-methoxy-N,2-dimethylpropan-2-aminefumarate (117 mg).

Example 191

To a mixture of N-{[6-(4,4-dimethylcyclohexyl)-2-methylthieno[2,3-d]pyrimidin-4-yl]methyl}tetrahydro-2H-thiopyran-4-amine-1,1-dioxide hydrochloride (100 mg), $CH_3I$ (16 μL) and DMF (2.0 mL) was added $K_2CO_3$ (60 mg), followed by stirring at 50° C. overnight. The reaction mixture was left to be cooled, and a saturated aqueous $NH_4Cl$ solution was added thereto, followed by extraction with EtOAc. The organic layer was washed sequentially with water and brine, and dried over $MgSO_4$. The residue was purified by silica gel column. The obtained purified product was dissolved in EtOAc, and 4 M HCl/EtOAc (55 μL) was added dropwise thereto. The precipitate was collected by filtration and then dried to obtain N-{[6-(4,4-dimethylcyclohexyl)-2-methylthieno[2,3-d]pyrimidin-4-yl]methyl}-N-methyltetrahydro-2H-thiopyran-4-amine 1,1-dioxidehydrochloride (69 mg).

Example 196

To a mixture of N-{[6-(4,4-dimethylcyclohexyl)-2-methylthieno[2,3-d]pyrimidin-4-yl]methyl}tetrahydro-2H-pyran-4-amine (100 mg), 1,4-dioxane-2,5-diol (64 mg), DCE (2 mL), and MeOH (1 mL) was added $NaBH(OAc)_3$ (170 mg) under ice-cooling, followed by stirring at 0° C. for 1 hour. To the reaction mixture were added water and EtOAc, followed by extraction with EtOAc. The organic layer was washed with brine, dried, and then concentrated under reduced pressure. The residue was purified by silica gel column to obtain 2-[{[6-(4,4-dimethylcyclohexyl)-2-methylthieno[2,3-d]pyrimidin-4-yl]methyl}(tetrahydro-2H-pyran-4-yl)amino]ethanol (51 mg).

Example 198

To a mixture of [6-(4,4-dimethylcyclohexyl)-2-methylthieno[2,3-d]pyrimidin-4-yl]methyl methanesulfonate (200 mg), DIPEA (139 μL), and DMF (3.0 mL) was added tetrahydro-2H-thiopyran-4-amine-1,1-dioxide (97 mg), followed by stirring at room temperature for 4 hours. To the reaction mixture was added a saturated aqueous $NH_4Cl$ solution, followed by extraction with EtOAc. The organic layer was washed sequentially with water and brine, dried over $MgSO_4$, and then concentrated under reduced pressure. The residue was purified by silica gel column and dissolved in EtOAc, and 4 M HCl/EtOAc (137 μL) was added dropwise. The precipitate was collected by filtration and then dried to obtain N-{[6-(4,4-dimethylcyclohexyl)-2-methylthieno[2,3-d]pyrimidin-4-yl]methyl}tetrahydro-2H-thiopyran-4-amine-1,1-dioxide hydrochloride (165 mg).

Example 205

To a suspension of N-{[6-(4,4-dimethylcyclohexyl)-2-methylthieno[2,3-d]pyrimidin-4-yl]methyl}-4-methyltetrahydro-2H-thiopyran-4-amine (55 mg) and sodium tungstate (IV) dihydrate (9.0 mg) in MeOH (1.1 mL) were sequentially added dropwise 1 M hydrochloric acid (313 μL) and a 35% hydrogen peroxide solution (56 μL) under ice-cooling, followed by stirring at the same temperature for 10 minutes, and further stirring at room temperature for 6 hours. To the reaction mixture that had been ice-cooled was added an aqueous $Na_2S_2O_3$ solution, followed by stirring at room temperature for 30 minutes. Then, saturated aqueous sodium bicarbonate was added thereto, followed by extraction with chloroform. The organic layer was washed with brine, dried over $MgSO_4$, and then concentrated under reduced pressure. The residue was purified by silica gel column. The obtained purified product was dissolved in EtOAc, and 4 M HCl/dioxane was added dropwise thereto. The precipitate was collected by filtration and then dried under reduced pressure to obtain N-{[6-(4,4-dimethylcyclohexyl)-2-methylthieno[2,3-d]pyrimidin-4-yl]methyl}-4-methyltetrahydro-2H-thiopyran-4-amine-1,1-dioxidehydrochloride (22 mg).

Example 206

To a mixture of 6-(4,4-dimethylcyclohexyl)-2-methylthieno[2,3-d]pyrimidine-4-carboxylic acid (150 mg), 4-methylpiperidin-4-ol (68 mg), HATU (262 mg), and NMP (2.1 mL) was added DIPEA (244 μL), followed by stirring at room temperature overnight. To the reaction mixture was added a saturated aqueous $NH_4Cl$ solution, followed by extraction with EtOAc. The organic layer was washed sequentially with water and brine, dried over $MgSO_4$, and then concentrated under reduced pressure. The residue was purified by silica gel column. The obtained purified product was suspended in IPE, collected by filtration, and then dried under reduced pressure to obtain [6-(4,4-dimethylcyclohexyl)-2-methylthieno[2,3-d]pyrimidin-4-yl](4-hydroxy-4-methylpiperidin-1-yl)methanone (120 mg).

Example 229

To a mixture of ethyl 2-[6-(4,4-dimethylcyclohexyl)-2-methylthieno[2,3-d]pyrimidin-4-yl]-3-(1,1-dioxidothiomorpholin-4-yl)-3-oxopropanpate (520 mg) and THF (16 mL) were added MeOH (2.7 mL) and a 1 M aqueous NaOH solution (3.9 mL) at room temperature, followed by stirring at 60° C. for 8 hours. The reaction mixture was left to be cooled, and then 1 M hydrochloric acid was added thereto, followed by concentration under reduced pressure. To the residue was added EtOAc, followed by extraction. The organic layer was washed with brine, dried over $MgSO_4$, and then concentrated under reduced pressure. The residue was purified by silica gel column to obtain 2-[6-(4,4-dimethylcyclohexyl)-2-methylthieno[2,3-d]pyrimidin-4-yl]-1-(1,1-dioxidethiomorpholin-4-yl)ethanone (322 mg).

In the same manner as the methods of Preparation Examples or Examples above, the compounds of Preparation Examples and Examples in Tables below were prepared.

TABLE 5

| No./Inf | Str |
|---|---|
| Pr1 | [structure] |
| Pr1-1 | [structure] |
| Pr1-2 | [structure] |
| Pr1-3 Chiral | [structure] |
| Pr1-4 | [structure] |
| Pr1-5 | [structure] |
| Pr1-6 | [structure] |
| Pr1-7 | [structure] |
| Pr1-8 | [structure] |
| Pr1-9 | [structure] |

TABLE 6
| No./Inf | Str |
|---|---|
| Pr1-10 | |
| Pr1-11 | |
| Pr1-12 | |
| Pr1-13 | |
| Pr1-14 | |
| Pr1-15 | |
TABLE 6-continued
| No./Inf | Str |
|---|---|
| Pr1-16 Chiral | |
| Pr1-17 | |
| Pr1-18 Chiral | |
| Pr2 | |
TABLE 7
| No./Inf | Str |
|---|---|
| Pr2-1 | 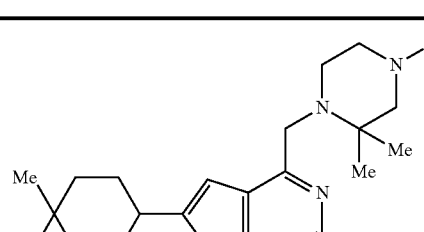 |

TABLE 7-continued

| No./Inf | Str |
|---|---|
| Pr2-2 | (structure) |
| Pr2-3 | (structure) |
| Pr2-4 Chiral | (structure) |
| Pr3 | (structure) |
| Pr3-1 | (structure) |
| Pr4 | (structure) |
| Pr4-1 | (structure) |
| Pr4-2 | (structure) |

TABLE 7-continued

| No./Inf | Str |
|---|---|
| Pr4-3 | (structure) |

TABLE 8

| No./Inf | Str |
|---|---|
| Pr4-4 | (structure) |
| Pr4-5 | (structure) |
| Pr4-6 | (structure) |
| Pr4-7 | (structure) |
| Pr4-8 | (structure) |
| Pr4-9 | (structure) |
| Pr4-10 | (structure) |

TABLE 8-continued

| No./Inf | Str |
|---|---|
| Pr5 | 6-(4,4-dimethylcyclohexyl)-2-methylthieno[2,3-d]pyrimidine-4-carbonitrile |
| Pr5-1 | 6-cyclohexyl-2-(difluoromethyl)thieno[2,3-d]pyrimidine-4-carbonitrile |
| Pr6 | ethyl 6-cyclohexyl-2-methylthieno[2,3-d]pyrimidine-4-carboxylate |
| Pr6-1 | ethyl 6-(4,4-dimethylcyclohexyl)-2-methylthieno[2,3-d]pyrimidine-4-carboxylate |
| Pr6-2 | ethyl 6-bromo-2-methylthieno[2,3-d]pyrimidine-4-carboxylate |

TABLE 9

| No./Inf | Str |
|---|---|
| Pr6-3 | ethyl 6-cyclohexyl-2-(difluoromethyl)thieno[2,3-d]pyrimidine-4-carboxylate |
| Pr6-4 | ethyl 6-(4,4-difluorocyclohexyl)-2-methylthieno[2,3-d]pyrimidine-4-carboxylate |
| Pr7 | [6-cyclohexyl-2-methylthieno[2,3-d]pyrimidin-4-yl]methanol |

TABLE 9-continued

| No./Inf | Str |
|---|---|
| Pr7-1 | [6-(4,4-dimethylcyclohexyl)-2-methylthieno[2,3-d]pyrimidin-4-yl]methanol |
| Pr7-2 | [6-bromo-2-methylthieno[2,3-d]pyrimidin-4-yl]methanol |
| Pr7-3 | [6-(4,4-difluorocyclohexyl)-2-methylthieno[2,3-d]pyrimidin-4-yl]methanol |

| No | Str |
|---|---|
| Pr7-4 | [6-cyclohexyl-2-(difluoromethyl)thieno[2,3-d]pyrimidin-4-yl]methanol |
| Pr8 | [6-(4,4-dimethylcyclohexyl)-2-methylthieno[2,3-d]pyrimidin-4-yl]methyl methanesulfonate |
| Pr8-1 | [6-cyclohexyl-2-methylthieno[2,3-d]pyrimidin-4-yl]methyl methanesulfonate |
| Pr8-2 | 2-[6-cyclohexyl-2-methylthieno[2,3-d]pyrimidin-4-yl]ethyl methanesulfonate |
| Pr8-3 | 1-[6-(4,4-dimethylcyclohexyl)-2-methylthieno[2,3-d]pyrimidin-4-yl]ethyl methanesulfonate |

TABLE 9-continued

| No./Inf | Str |
|---|---|
| Pr8-4 | (structure) |

TABLE 10

| No./Inf | Str |
|---|---|
| Pr8-5 | (structure) |
| Pr8-6 | (structure) |
| Pr8-7 | (structure) |
| Pr8-8 | (structure) |
| Pr8-9 | (structure) |
| Pr8-10 | (structure) |
| Pr9 | (structure) |

TABLE 10-continued

| No./Inf | Str |
|---|---|
| Pr9-1 | (structure) |
| Pr9-2 | (structure) |
| Pr9-3 | (structure) |
| Pr9-4 | (structure) |
| Pr10 | (structure) |

TABLE 11

| No./Inf | Str |
|---|---|
| Pr10-1 | (structure) |
| Pr10-2 | (structure) |
| Pr10-3 | (structure) |

TABLE 11-continued

| No./Inf | Str |
|---|---|
| Pr10-4 | [structure: 2-Me-thiazolopyrimidine with trans-4-Me-cyclohexyl and CH2-O-C(O)-Ph] |
| Pr11 | [structure: 2-Me-thiazolopyrimidine with 4,4-diMe-cyclohexyl and CH2OH] |
| Pr11-1 | [structure: 2-Me-thiazolopyrimidine with cyclohexyl and CH2OH] |
| Pr11-2 | [structure: 2-Me-thiazolopyrimidine with trans-4-Me-cyclohexyl and CH2OH] |
| Pr11-3 | [structure: 2-Me-thiazolopyrimidine with trans-4-CF3-cyclohexyl and CH2OH] |
| Pr12 | [structure: 6-cyclohexyl-2-Me-thieno[2,3-d]pyrimidin-4(3H)-one] |
| Pr12-1 | [structure: 6-(4,4-difluorocyclohexyl)-2-Me-thieno[2,3-d]pyrimidin-4(3H)-one] |

TABLE 12

| No./Inf | Str |
|---|---|
| Pr13 | [structure: 6-cyclohexyl-2-Me-thieno[2,3-d]pyrimidine-4-CH2Cl] |
| Pr14 | [structure: 6-cyclohexyl-2-Me-thieno[2,3-d]pyrimidine-4-CH=CH-OEt] |
| Pr14-1 | [structure: 6-(4,4-diMe-cyclohexyl)-2-Me-thieno[2,3-d]pyrimidine-4-CH=CH-OEt] |
| Pr15 | [structure: 6-(4,4-diMe-cyclohexyl)-2-Me-thieno[2,3-d]pyrimidine-4-CH2-(2,2-diMe-piperazin-1-yl)] |
| Pr15-1 Chiral | [structure: chiral diazabicyclic amine substituted thiazolopyrimidine with 4,4-diMe-cyclohexyl] |

| No | Str |
|---|---|
| Pr15-2 | [structure: 6-(4,4-diMe-cyclohexyl)-2-Me-thiazolo[5,4-d]pyrimidine-CH2-(2,2-diMe-piperazin-1-yl)] |
| Pr16 | [structure: 6-cyclohexyl-2-Me-thieno[2,3-d]pyrimidine-4-CH=CH-OH] |
| Pr16-1 | [structure: 6-(4,4-diMe-cyclohexyl)-2-Me-thieno[2,3-d]pyrimidine-4-CH=CH-OH] |

TABLE 12-continued

| Pr17 | (structure: 6-cyclohexyl-thieno[2,3-d]pyrimidine with 4-(2-hydroxyethyl) and 2-Me) |
| Pr17-1 | (structure: 6-(4,4-dimethylcyclohexyl)-thieno[2,3-d]pyrimidine with 4-(1-hydroxyethyl) and 2-Me) |

TABLE 13

| No./Inf | Str |
|---|---|
| Pr17-2 | (structure: 6-(4,4-dimethylcyclohexyl)-thieno[2,3-d]pyrimidine with 4-(2-hydroxyethyl) and 2-Me) |
| Pr18 | (structure: 6-(4,4-dimethylcyclohexyl)-thieno[2,3-d]pyrimidine-4-carboxylic acid, 2-Me) |
| Pr18-1 | (structure: 2-adamantyl-thiazolo[5,4-d]pyrimidine with 7-hydroxymethyl and 5-Me) |
| Pr19 | (structure: 2-(4,4-dimethylcyclohexyl)-thiazolo[5,4-d]pyrimidine-7-carboxylic acid, 5-Me) |
| Pr20 | (structure: 6-(4,4-dimethylcyclohexyl)-thieno[2,3-d]pyrimidine with 4-acetyl and 2-Me) |

TABLE 13-continued

| No./Inf | Str |
|---|---|
| Pr21 | (structure: 6-cyclohexyl-thieno[2,3-d]pyrimidine with 4-[(5-benzyl-2-oxo-2,5-diazabicyclo)methyl] and 2-Me) |
| Pr22 | (structure: 6-bromo-4-methoxy-2-methyl-thieno[2,3-d]pyrimidine) |
| Pr23 | (structure: 6-chloro-2-methyl-thieno[2,3-d]pyrimidin-4(3H)-one) |
| Pr24 | (structure: 6-cyclohexyl-4-cyano-2-methyl-thieno[2,3-d]pyrimidine) |
| Pr24-1 | (structure: 6-(4,4-difluorocyclohexyl)-4-cyano-2-methyl-thieno[2,3-d]pyrimidine) |

TABLE 14

| No./Inf | Str |
|---|---|
| Pr24-2 | (structure: 6-bromo-4-cyano-2-methyl-thieno[2,3-d]pyrimidine) |
| Pr25 | (structure: 6-(4,4-dimethylcyclohexyl)-2-methyl-thieno[2,3-d]pyrimidine-4-yl, ethyl 2-(thiomorpholine-1,1-dioxide-4-carbonyl) acetate) |

TABLE 14-continued
| No./Inf | Str |
|---|---|
| Pr25-1 | 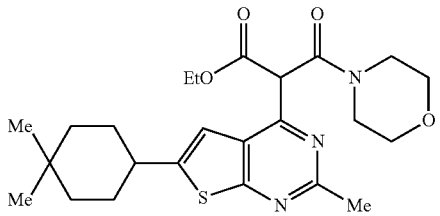 [SMILES: CCOC(=O)C(C(=O)N1CCOCC1)c1nc(C)nc2sc(C3CCC(C)(C)CC3)cc12] |
| Pr25-2 | 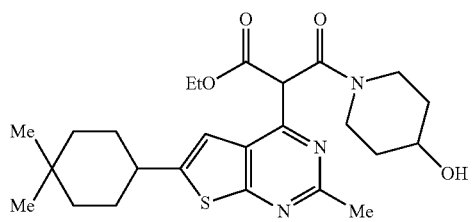 [SMILES: CCOC(=O)C(C(=O)N1CCC(O)CC1)c1nc(C)nc2sc(C3CCC(C)(C)CC3)cc12] |
| Pr26 | 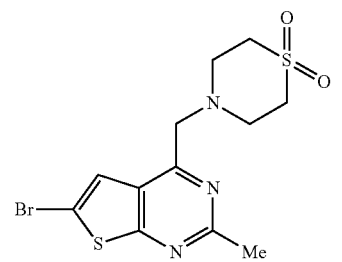 [SMILES: Cc1nc(CN2CCS(=O)(=O)CC2)c2cc(Br)sc2n1] |
| Pr26-1 Chiral | 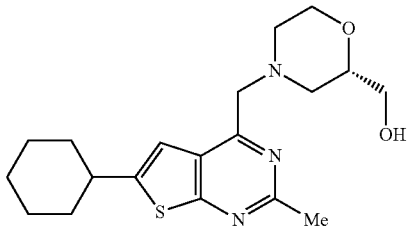 [SMILES: Cc1nc(CN2CCO[C@H](CO)C2)c2cc(C3CCCCC3)sc2n1] |
| Pr27/ 2HCl | 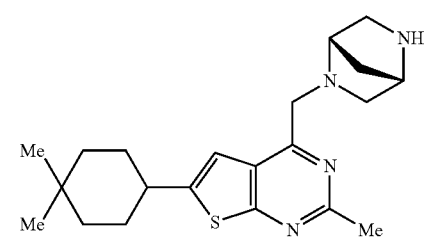 [SMILES: Cc1nc(CN2C[C@@H]3C[C@H]2CN3)c2cc(C3CCC(C)(C)CC3)sc2n1] |
| Pr28 | 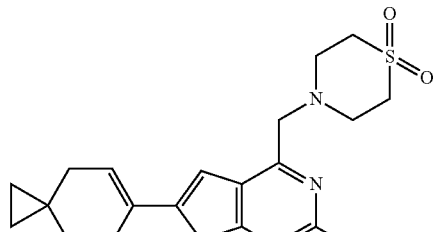 |
TABLE 14-continued
| No./Inf | Str |
|---|---|
| Pr29 | 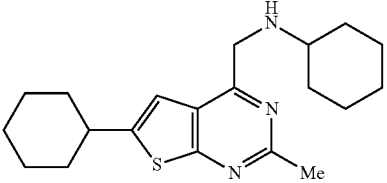 [SMILES: Cc1nc(CNC2CCCCC2)c2cc(C3CCCCC3)sc2n1] |
| Pr30 | 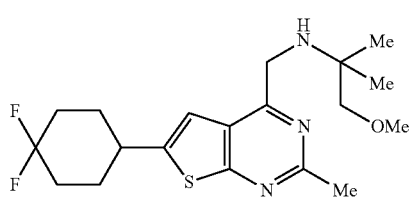 [SMILES: COCC(C)(C)NCc1nc(C)nc2sc(C3CCC(F)(F)CC3)cc12] |
TABLE 15
| No./Inf | Str |
|---|---|
| Pr30-1 | 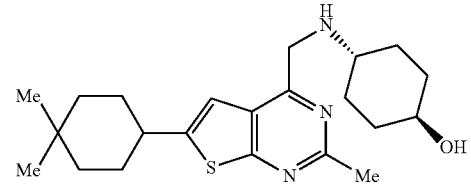 [SMILES: Cc1nc(CN[C@H]2CC[C@H](O)CC2)c2cc(C3CCC(C)(C)CC3)sc2n1] |
| Pr30-2 | 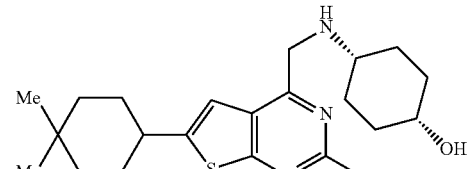 |
| Pr31 | 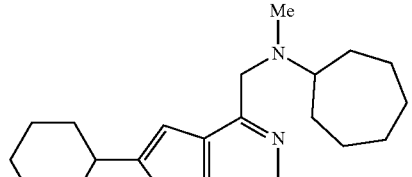 |
| Pr31-1 | 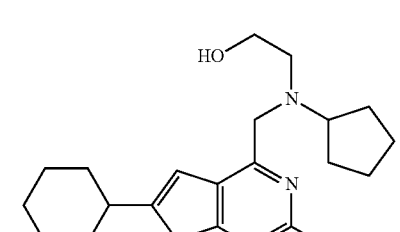 |

TABLE 15-continued
| No./Inf | Str |
|---|---|
| Pr31-2 | 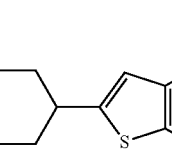 |
| Pr31-3 | 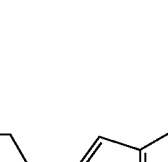 |
| Pr31-4 | 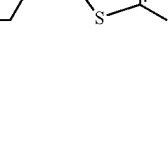 |
| Pr32 | 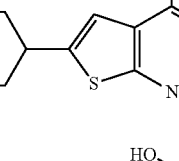 |
| Pr32-1 | 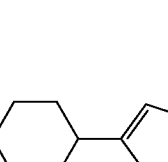 |
| Pr32-2 |  |
TABLE 16
| No./Inf | Str |
|---|---|
| Pr32-3 | 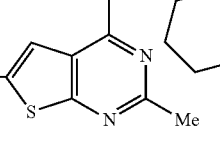 |
| Pr33 | 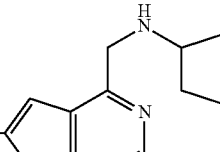 |
| Pr33-1 | 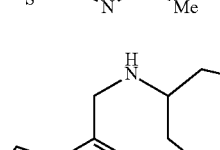 |
| Pr33-2 | 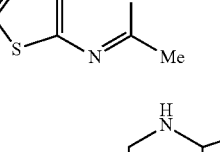 |
| Pr34 | 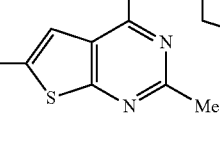 |
| Pr34-1 | 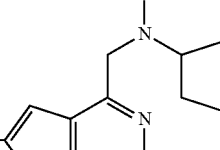 |
| Pr34-2 | 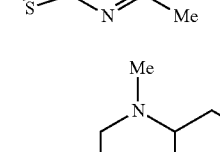 |

TABLE 16-continued

| No./Inf | Str |
|---|---|
| Pr34-3 | (6-cyclohexyl-2-methylthieno[2,3-d]pyrimidin-4-yl)methyl-(4,4-difluorocyclohexyl)amine |
| Pr34-4 | N-[(6-(4,4-dimethylcyclohexyl)-2-methylthieno[2,3-d]pyrimidin-4-yl)methyl]-4-methyltetrahydrothiopyran-4-amine |
| Pr35-5 | (6-cyclohexyl-2-methylthieno[2,3-d]pyrimidin-4-yl)methyl-cyclohexyl-methylamine |

TABLE 17

| No./Inf | Str |
|---|---|
| Pr34-6 | N-[(6-(4,4-dimethylcyclohexyl)-2-methylthieno[2,3-d]pyrimidin-4-yl)methyl]tetrahydropyran-4-amine |
| Pr34-7 | N-[(6-(4,4-dimethylcyclohexyl)-2-methylthieno[2,3-d]pyrimidin-4-yl)methyl]oxetan-3-amine |
| Pr35/HCl | N-[(6-(4,4-difluorocyclohexyl)-2-methylthieno[2,3-d]pyrimidin-4-yl)methyl]ethylamine |
| Pr36/HCl | N-[(6-(4,4-dimethylcyclohexyl)-2-methylthieno[2,3-d]pyrimidin-4-yl)methyl]-1,1-dioxothietan-3-amine |

TABLE 17-continued

| No./Inf | Str |
|---|---|
| Pr37 | 2-amino-5-(4,4-dimethylcyclohexyl)thiophene-3-carboxamide |
| Pr37-1 | 2-amino-5-(4,4-difluorocyclohexyl)thiophene-3-carboxamide |
| Pr37-2 | 2-amino-5-cyclohexylthiophene-3-carboxamide |
| Pr38 | 2-acetamido-5-(4,4-dimethylcyclohexyl)thiophene-3-carboxamide |
| Pr39 | 5-cyclohexyl-2-(2,2-difluoroacetamido)thiophene-3-carboxamide |
| Pr40 | N-(4,6-dichloro-2-methylpyrimidin-5-yl)-4,4-dimethylcyclohexanecarboxamide |
| Pr40-1 | N-(4,6-dichloro-2-methylpyrimidin-5-yl)cyclohexanecarboxamide |
| Pr40-2 | N-(4,6-dichloro-2-methylpyrimidin-5-yl)-4-(trifluoromethyl)cyclohexanecarboxamide |

TABLE 18

| No./Inf | Str |
|---|---|
| Pr40-3 | Me-cyclohexyl-C(=O)-NH-(4,6-dichloro-2-methylpyrimidin-5-yl) |
| Pr41 | 1-adamantyl-C(=O)-NH-(4,6-dichloro-2-methylpyrimidin-5-yl) |
| Pr42 | EtO-C(=O)-CH2-C(=O)-N(thiomorpholine 1,1-dioxide) |
| Pr42-1 | EtO-C(=O)-CH2-C(=O)-N(piperidin-4-yl)-O-C(=O)-CH2-C(=O)-OEt |
| Pr43 | 4,4-dimethylcyclohexyl-CH2-CHO |
| Pr44 | EtO-C(=O)-CH2-C(=O)-N(4-hydroxypiperidinyl) |
| Pr45 | 1-benzyl-3-methyl-piperidine-3,4-diol |
| Pr46 | bicyclic diamine lactam |
| Pr47/AcOH | 4-methyl-piperidine-3,3-diol |
| Pr48 | 1-Boc-3-methyl-piperidine-3,4-diol |
| Pr49 | 2,2-dimethyl-3-hydroxyazetidine |

TABLE 18-continued

| No./Inf | Str |
|---|---|
| Pr50 | 1-benzyl-6-methyl-7-oxa-3-azabicyclo[4.1.0]heptane |
| Pr51/AcOH | 1-benzyl-4-methyl-piperidine-3,4-diol |
| Pr52/HCl | 3-methyl-piperidine-3,4-diol |

TABLE 19

| No./Inf | Str |
|---|---|
| Ex1 | 6-cyclohexyl-4-((1,1-dioxothiomorpholin-4-yl)methyl)-2-methylthieno[2,3-d]pyrimidine |
| Ex2 | 6-(4,4-dimethylcyclohexyl)-4-((1,1-dioxothiomorpholin-4-yl)methyl)-2-methylthieno[2,3-d]pyrimidine |
| Ex3 Chiral | 6-cyclohexyl-4-(((3R)-3-methoxypiperidin-1-yl)methyl)-2-methylthieno[2,3-d]pyrimidine |

TABLE 19-continued

| No./Inf | Str |
|---|---|
| Ex4 | (structure) |
| Ex5 | (structure) |
| Ex6 | (structure) |
| Ex7 | (structure) |
| Ex8 | (structure) |
| Ex9 | (structure) |
| Ex10 | (structure) |

TABLE 20

| No./Inf | Str |
|---|---|
| Ex11 | (structure) |
| Ex12 | (structure) |
| Ex13 | (structure) |
| Ex14 | (structure) |

TABLE 20-continued

| No./Inf | Str |
|---|---|
| Ex15 | (structure) |
| Ex16 | (structure) |
| Ex17 | (structure) |
| Ex18 | (structure) |
| Ex19 Chiral | (structure) |
| Ex20 | (structure) |

TABLE 21

| No./Inf | Str |
|---|---|
| Ex21 | (structure) |
| Ex22 | (structure) |
| Ex23 | (structure) |
| Ex24 | (structure) |
| Ex25 | (structure) |
| Ex26 | (structure) |

TABLE 21-continued

| No./Inf | Str |
|---|---|
| Ex27 | (structure) |
| Ex28 | (structure) |
| Ex29 | (structure) |
| Ex30 | (structure) |

TABLE 22

| No./Inf | Str |
|---|---|
| Ex31 Chiral | (structure) |
| Ex31-1 Chiral | (structure) |
| Ex32 Chiral | (structure) |
| Ex32-1 Chiral | (structure) |
| Ex33/HCl | (structure) |
| Ex34/HCl | (structure) |
| Ex35/HCl Chiral | (structure) |

TABLE 22-continued

| No./Inf | Str |
|---|---|
| Ex36/HCl Chiral | (S)-1-((6-cyclohexyl-2-methylthieno[2,3-d]pyrimidin-4-yl)methyl)piperidin-3-ol |
| Ex37/HCl | 4-((4,4-dimethylpiperidin-1-yl)methyl)-6-cyclohexyl-2-methylthieno[2,3-d]pyrimidine |
| Ex38/HCl | 4-((3,3-dimethylpiperidin-1-yl)methyl)-6-cyclohexyl-2-methylthieno[2,3-d]pyrimidine |

TABLE 23

| No./Inf | Str |
|---|---|
| Ex39/HCl | 4-(((2R,6S)-2,6-dimethylmorpholino)methyl)-6-(4,4-dimethylcyclohexyl)-2-methylthieno[2,3-d]pyrimidine |
| Ex40/HCl | 4-((2,2-dimethylmorpholino)methyl)-6-(4,4-dimethylcyclohexyl)-2-methylthieno[2,3-d]pyrimidine |
| Ex41/HCl | 4-((2,2-dimethylpyrrolidin-1-yl)methyl)-6-(4,4-dimethylcyclohexyl)-2-methylthieno[2,3-d]pyrimidine |
| Ex42/HCl | 4-((2,2-dimethylpyrrolidin-1-yl)methyl)-6-cyclohexyl-2-methylthieno[2,3-d]pyrimidine |
| Ex43/HCl | 6-(4,4-dimethylcyclohexyl)-2-methyl-4-((6-azaspiro[2.5]octan-6-yl)methyl)thieno[2,3-d]pyrimidine |
| Ex44/HCl | 4-((4,4-dimethylpiperidin-1-yl)methyl)-6-(4,4-dimethylcyclohexyl)-2-methylthieno[2,3-d]pyrimidine |
| Ex45/HCl | 4-((3,3-dimethylpiperidin-1-yl)methyl)-6-(4,4-dimethylcyclohexyl)-2-methylthieno[2,3-d]pyrimidine |
| Ex46/HCl | (1-((6-(4,4-dimethylcyclohexyl)-2-methylthieno[2,3-d]pyrimidin-4-yl)methyl)-4-methoxypiperidin-4-yl)methanol |

TABLE 23-continued

| No./Inf | Str |
|---|---|
| Ex47/HCl | (structure) |
| Ex48/HCl | (structure) |

TABLE 24

| No./Inf | Str |
|---|---|
| Ex49/HCl | (structure) |
| Ex50/HCl | (structure) |
| Ex51/HCl | (structure) |

TABLE 24-continued

| No./Inf | Str |
|---|---|
| Ex52/HCl | (structure) |
| Ex53/HCl | (structure) |
| Ex54/HCl | (structure) |
| Ex55/HCl | (structure) |
| Ex56/HCl | (structure) |
| Ex57/HCl | (structure) |

TABLE 24-continued

| No./Inf | Str |
|---|---|
| Ex58/HCl | (6-cyclohexyl-2-methylthieno[2,3-d]pyrimidin-4-yl)methyl-3,3-difluoropiperidine |

TABLE 25

| No./Inf | Str |
|---|---|
| Ex59/HCl Chiral | (2S)-1-[(6-cyclohexyl-2-methylthieno[2,3-d]pyrimidin-4-yl)methyl]-2-methylpyrrolidine |
| Ex60/HCl Chiral | (2R)-1-[(6-cyclohexyl-2-methylthieno[2,3-d]pyrimidin-4-yl)methyl]-2-methylpyrrolidine |
| Ex61/HCl | 1-{[6-(4,4-dimethylcyclohexyl)-2-methylthieno[2,3-d]pyrimidin-4-yl]methyl}-4-(difluoromethyl)piperidine |
| Ex62/HCl | (1-{[6-(4,4-dimethylcyclohexyl)-2-methylthieno[2,3-d]pyrimidin-4-yl]methyl}azetidin-3-yl)methanol |

TABLE 25-continued

| No./Inf | Str |
|---|---|
| Ex63/HCl | 1-{1-[6-(4,4-dimethylcyclohexyl)-2-methylthieno[2,3-d]pyrimidin-4-yl]ethyl}-4-methylpiperidin-4-ol |
| Ex64/HCl | 4-{[(6-cyclohexyl-2-methylthieno[2,3-d]pyrimidin-4-yl)methyl]}morpholine |
| Ex65/HCl | 4-[(6-cyclohexyl-2-methylthieno[2,3-d]pyrimidin-4-yl)methyl]-1-methylpiperazin-2-one |
| Ex66/HCl | 2-[(6-cyclohexyl-2-methylthieno[2,3-d]pyrimidin-4-yl)methyl]-2,3-dihydro-1H-isoindole |
| Ex67/2HCl | 2-[(6-cyclohexyl-2-methylthieno[2,3-d]pyrimidin-4-yl)methyl]-2,3-dihydro-1H-pyrrolo[3,4-b]pyridine |
| Ex68/HCl | 2-[(6-cyclohexyl-2-methylthieno[2,3-d]pyrimidin-4-yl)methyl]-1,2,3,4-tetrahydroisoquinoline |

TABLE 29
| No./Inf | Str |
|---|---|
| Ex69/ 2HCl | 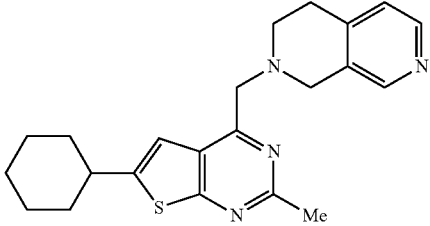 [SMILES: Cc1nc(CN2CCc3ccncc3C2)c2cc(C3CCCCC3)sc2n1] |
| Ex70/ 2HCl | 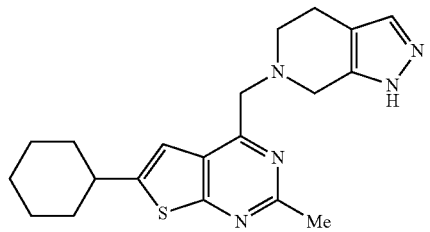 [SMILES: Cc1nc(CN2CCc3cn[nH]c3C2)c2cc(C3CCCCC3)sc2n1] |
| Ex71/ 2HCl | 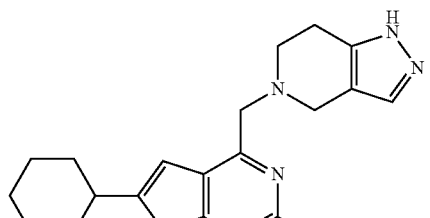 |
| Ex72/ HCl Chiral | 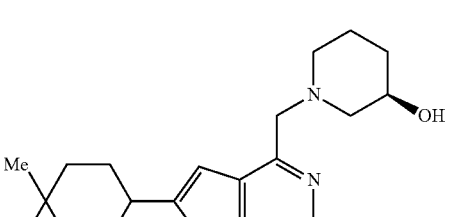 |
| Ex73/ HCl Chiral | 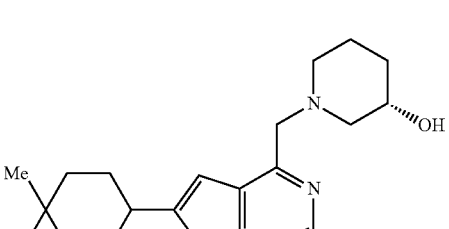 |
| Ex74/ HCl | 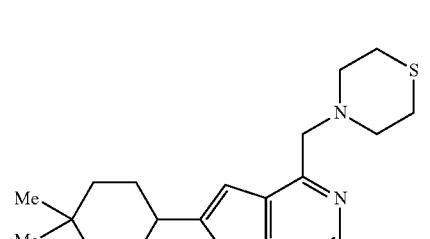 |
TABLE 29-continued
| No./Inf | Str |
|---|---|
| Ex75/ HCl | 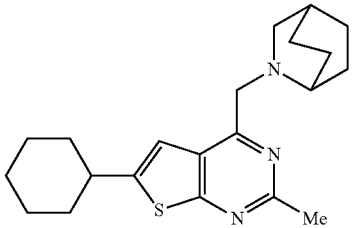 [SMILES: Cc1nc(CN2CC3CCC2CC3)c2cc(C3CCCCC3)sc2n1] |
| Ex76/ HCl | 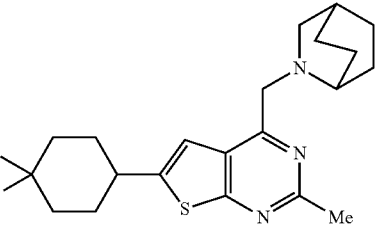 |
| Ex77/ HCl | 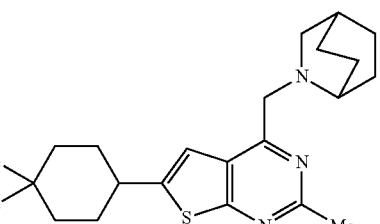 |
| Ex78/ HCl Chiral | 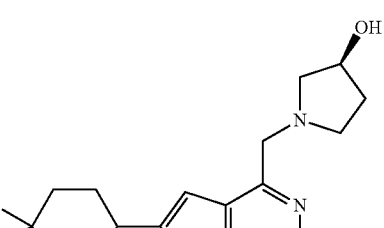 |
TABLE 27
| No./Inf | Str |
|---|---|
| Ex79/ HCl | 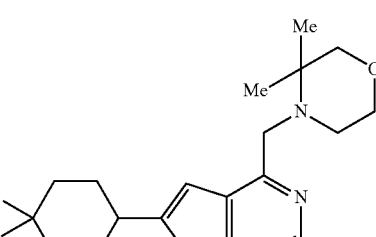 |

TABLE 27-continued

| No./Inf | Str |
|---|---|
| Ex80/HCl | |
| Ex81/HCl | |
| Ex82/2HCl | |
| Ex83/2HCl | |
| Ex84/HCl | |

TABLE 27-continued

| No./Inf | Str |
|---|---|
| Ex85 | |
| Ex86 | |
| Ex87 | |
| Ex88 | |

TABLE 28

| No./Inf | Str |
|---|---|
| Ex89 | |

TABLE 28-continued

| No./Inf | Str |
|---|---|
| Ex90 | (structure) |
| Ex91 | (structure) |
| Ex92 | (structure) |
| Ex93 | (structure) |
| Ex94 | (structure) |
| Ex95 | (structure) |
| Ex96/HCl | (structure) |
| Ex97/HCl | (structure) |
| Ex98/HCl | (structure) |

TABLE 29

| No./Inf | Str |
|---|---|
| Ex99/HCl | (structure) |
| Ex100/HCl | (structure) |

TABLE 29-continued

| No./Inf | Str |
|---|---|
| Ex101/HCl Chiral | (structure) |
| Ex102/HCl Chiral | (structure) |
| Ex103/HCl | (structure) |
| Ex104/HCl | (structure) |
| Ex105/HCl | (structure) |
| Ex106 | (structure) |
| Ex107/HCl | (structure) |
| Ex108 | (structure) |

TABLE 30

| No./Inf | Str |
|---|---|
| Ex109 Chiral | (structure) |
| Ex110 Chiral | (structure) |
| Ex111 HCl Chiral | (structure) |

TABLE 30-continued

| No./Inf | Str |
|---|---|
| Ex112 | (structure) |
| Ex113 | (structure) |
| Ex114 | (structure) |
| Ex115 | (structure) |
| Ex116/FUM | (structure) |
| Ex117/FUM Chiral | (structure) |
| Ex118/FUM | (structure) |

TABLE 31

| No./Inf | Str |
|---|---|
| Ex119/FUM | (structure) |
| Ex120/FUM | (structure) |
| Ex121/FUM | (structure) |
| Ex122/FUM | (structure) |
| Ex123/FUM | (structure) |

TABLE 31-continued

| No./Inf | Str |
|---|---|
| Ex124/FUM | (structure) |
| Ex125/FUM Chiral | (structure) |
| Ex126/FUM | (structure) |
| Ex127/FUM | (structure) |
| Ex128/FUM | (structure) |

TABLE 32

| No./Inf | Str |
|---|---|
| Ex129 | (structure) |
| Ex130/2HCl | (structure) |
| Ex131/HCl Chiral | (structure) |
| Ex132/HCl | (structure) |
| Ex133/2HCl | (structure) |
| Ex134/FUM Chiral | (structure) |

TABLE 32-continued
| No./Inf | Str |
|---|---|
| Ex135/FUM Chiral | 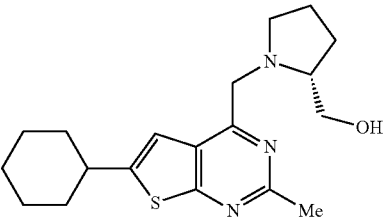 [SMILES: Cc1nc(CN2CCC[C@@H]2CO)c2cc(C3CCCCC3)sc2n1] |
| Ex136/FUM Chiral | 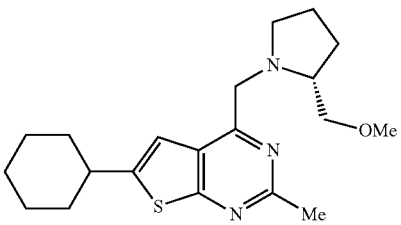 [SMILES: COC[C@H]1CCCN1Cc1nc(C)nc2sc(C3CCCCC3)cc12] |
| Ex137/FUM Chiral | 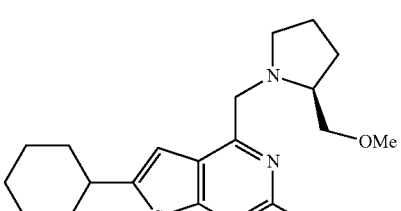 |
| Ex138/FUM Chiral | 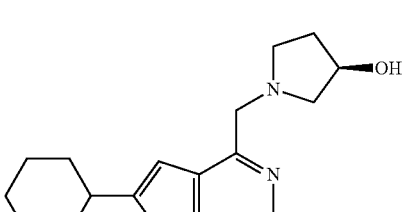 |
TABLE 33
| No./Inf | Str |
|---|---|
| Ex139/FUM Chiral | 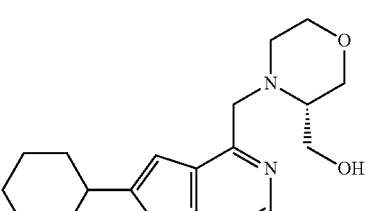 |
| Ex140 Chiral | 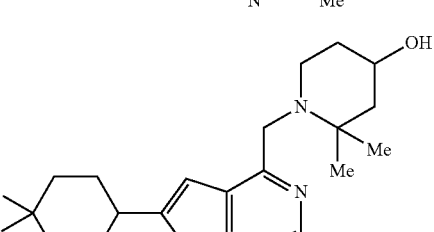 |
TABLE 33-continued
| No./Inf | Str |
|---|---|
| Ex141 Chiral | 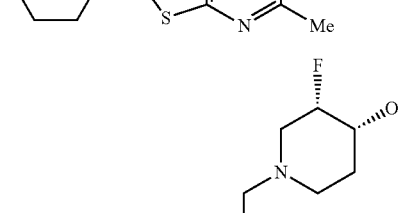 |
| Ex142 | 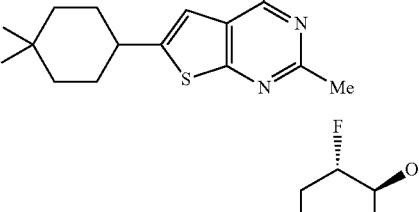 |
| Ex143 Chiral | 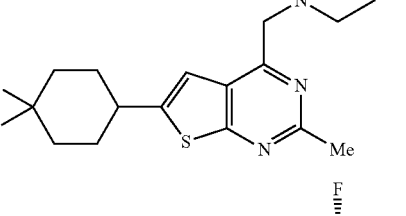 |
| Ex144 | 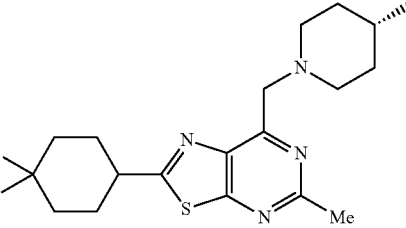 |
| Ex145 Chiral | 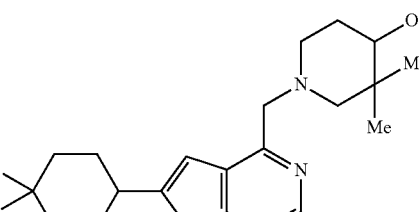 |
| Ex146/HCl | 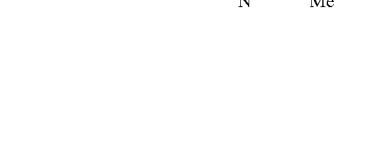 |

TABLE 33-continued
| No./Inf | Str |
|---|---|
| Ex147/HCl | 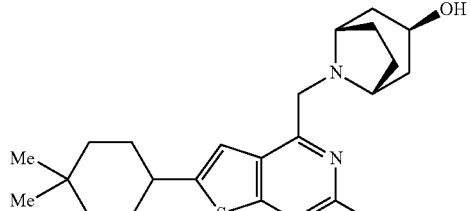 |
| Ex148/HCl | 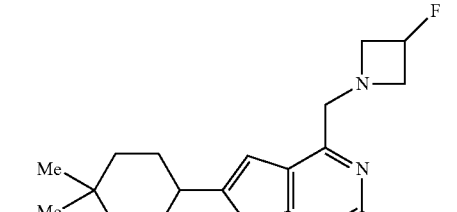 |
TABLE 34
| No./Inf | Str |
|---|---|
| Ex149/HCl | 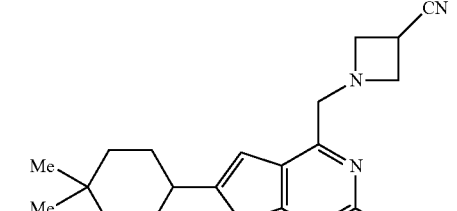 |
| Ex150/FUM | 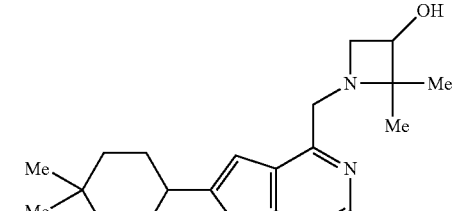 |
| Ex151/FUM | 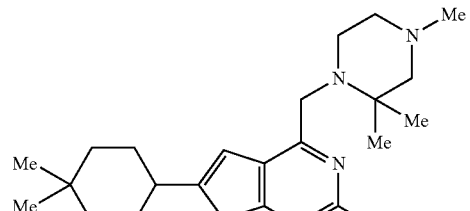 |
TABLE 34-continued
| No./Inf | Str |
|---|---|
| Ex152 | 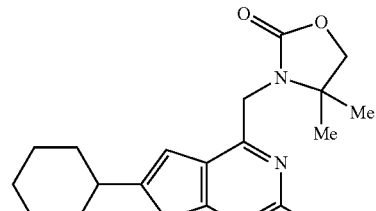 |
| Ex153/HCl |  |
| Ex154 | 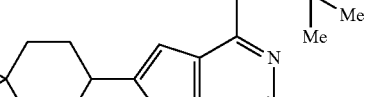 |
| Ex155 |  |
| Ex156 |  |

TABLE 34-continued

| No./Inf | Str |
|---|---|
| Ex157 | (structure) |
| Ex158 | (structure) |

TABLE 35

| No./Inf | Str |
|---|---|
| Ex159 Chiral | (structure) |
| Ex160 | (structure) |
| Ex161/ FUM Chiral | (structure) |

TABLE 35-continued

| No./Inf | Str |
|---|---|
| Ex162/ FUM | (structure) |
| Ex163 | (structure) |
| Ex164/ HCl | (structure) |
| Ex165/ HCl | (structure) |
| Ex166/ HCl | (structure) |
| Ex167/ HCl | (structure) |

TABLE 35-continued
| No./Inf | Str |
|---|---|
| Ex168 | 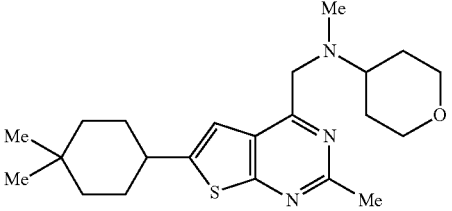 [SMILES: Cc1nc(CN(C)C2CCOCC2)c2cc(C3CCC(C)(C)CC3)sc2n1] |
TABLE 36
| No./Inf | Str |
|---|---|
| Ex169 | |
| Ex170 | |
| Ex171/HCl | |
| Ex172/HCl | |
| Ex173/HCl | |
TABLE 36-continued
| No./Inf | Str |
|---|---|
| Ex174/HCl | |
| Ex175/HCl | |
| Ex176/HCl | |
| Ex177/HCl | |
| Ex178/HCl | |
TABLE 37
| No./Inf | Str |
|---|---|
| Ex179/HCl | 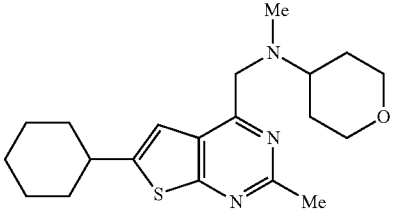 [SMILES: Cc1nc(CN(C)C2CCOCC2)c2cc(C3CCCCC3)sc2n1] |

TABLE 37-continued

| No./Inf | Str |
|---|---|
| Ex180/HCl | (structure) |
| Ex181/HCl | (structure) |
| Ex182/HCl | (structure) |
| Ex183/HCl | (structure) |
| Ex184/HCl | (structure) |
| Ex185/HCl | (structure) |
| Ex186 | (structure) |
| Ex187 | (structure) |
| Ex188 | (structure) |

TABLE 38

| No./Inf | Str |
|---|---|
| Ex189 | (structure) |
| Ex190/FUM | (structure) |
| Ex191/HCl | (structure) |

TABLE 38-continued
| No./Inf | Str |
|---|---|
| Ex192/HCl | 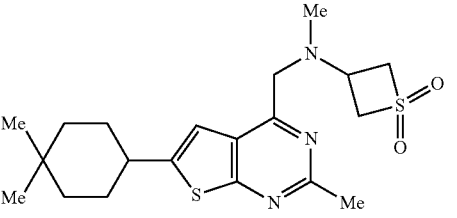 [SMILES: Cc1nc(CN(C)C2CS(=O)(=O)C2)c2cc(C3CCC(C)(C)CC3)sc2n1] |
| Ex193/HCl | 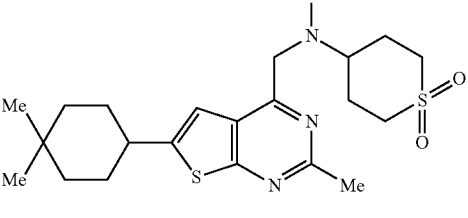 |
| Ex194 | 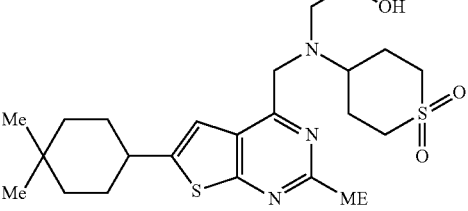 |
| Ex195 | 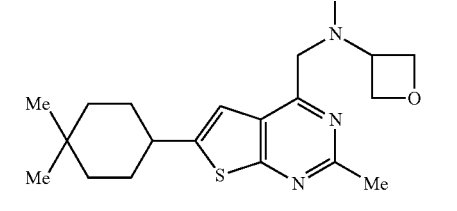 |
| Ex196 | 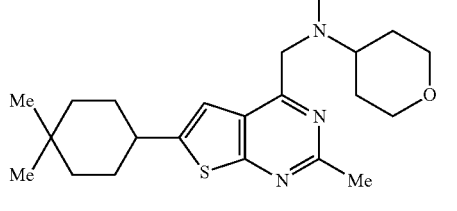 |
| Ex197/HCl | 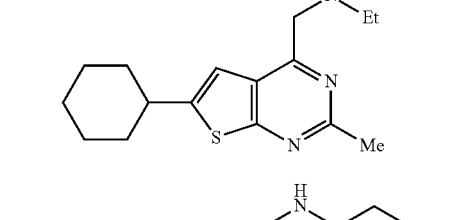 |
| Ex198/HCl | 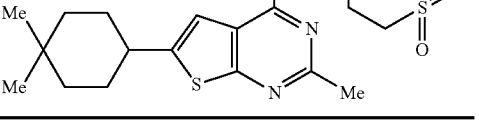 |
TABLE 39
| No./Inf | Str |
|---|---|
| Ex199/HCl Chiral | 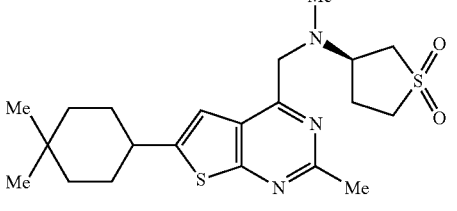 |
| Ex200/HCl Chiral | 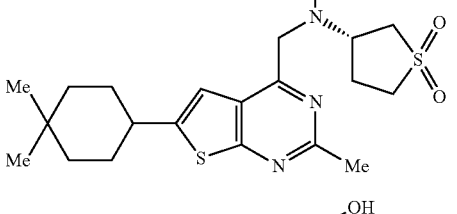 |
| Ex201 | 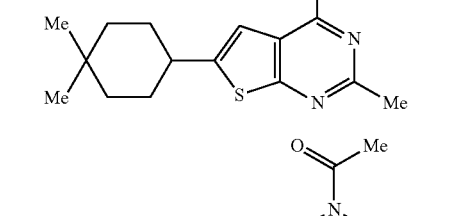 |
| Ex202 | 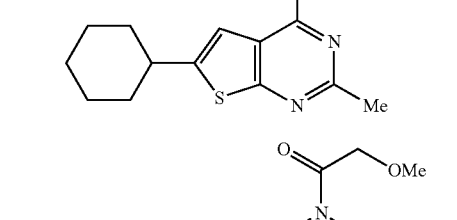 |
| Ex203 | 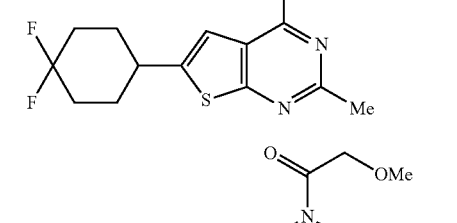 |
| Ex204 | 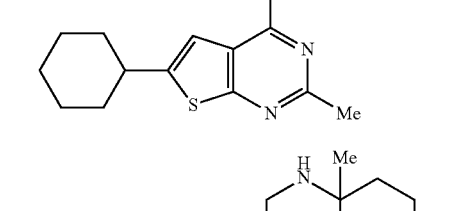 |
| Ex205/HCl | 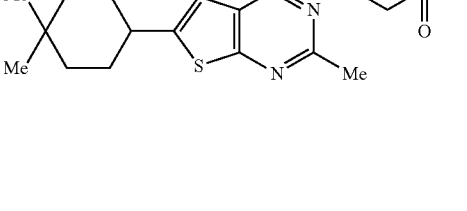 |

TABLE 39-continued
| No./Inf | Str |
|---|---|
| Ex206 | 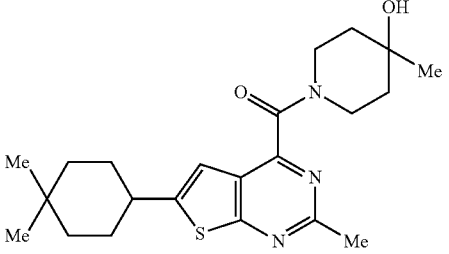 [SMILES: Cc1nc(C(=O)N2CCC(C)(O)CC2)c2cc(C3CCC(C)(C)CC3)sc2n1] |
| Ex207 | 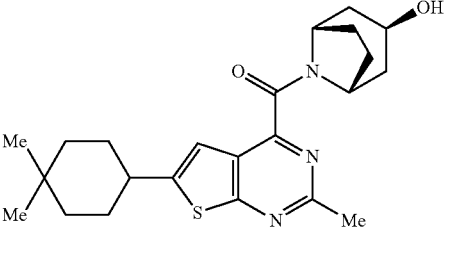 [SMILES: Cc1nc(C(=O)N2[C@@H]3CC[C@H]2C[C@@H](O)C3)c2cc(C3CCC(C)(C)CC3)sc2n1] |
| Ex208 | 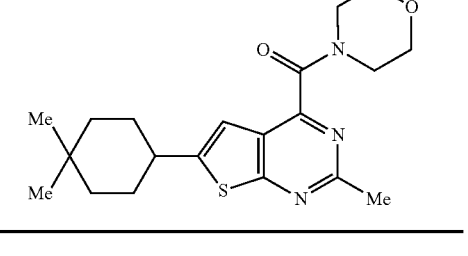 |
TABLE 40
| No./Inf | Str |
|---|---|
| Ex209 | 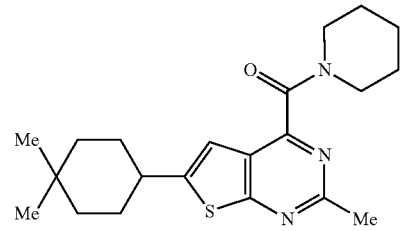 [SMILES: Cc1nc(C(=O)N2CCCCC2)c2cc(C3CCC(C)(C)CC3)sc2n1] |
| Ex210 | 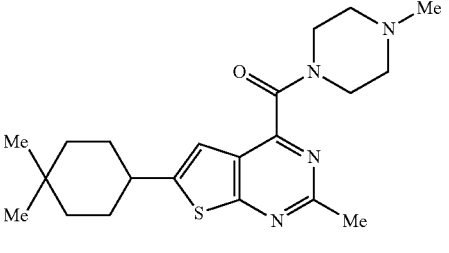 [SMILES: Cc1nc(C(=O)N2CCN(C)CC2)c2cc(C3CCC(C)(C)CC3)sc2n1] |
TABLE 40-continued
| No./Inf | Str |
|---|---|
| Ex211 | 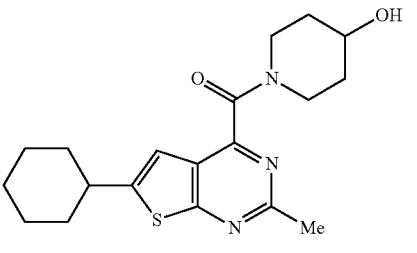 [SMILES: Cc1nc(C(=O)N2CCC(O)CC2)c2cc(C3CCCCC3)sc2n1] |
| Ex212 | 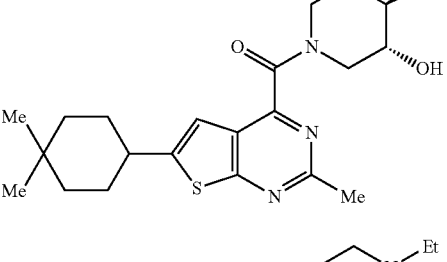 |
| Ex213 | 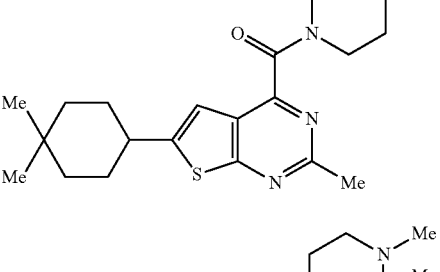 |
| Ex214 | 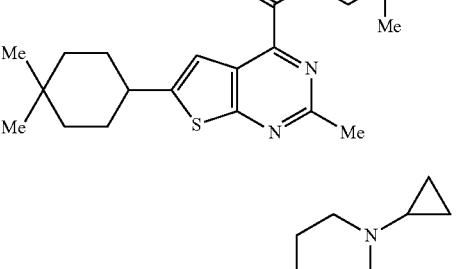 |
| Ex215 | 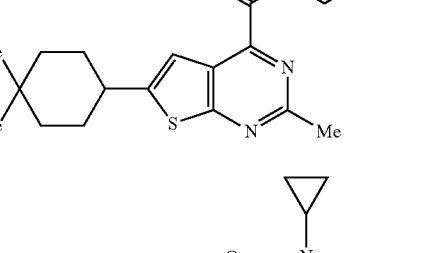 |
| Ex216 | 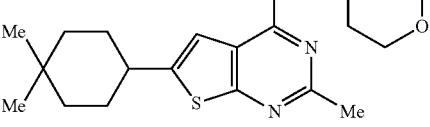 |

TABLE 40-continued
| No./Inf | Str |
|---|---|
| Ex217 Chiral | 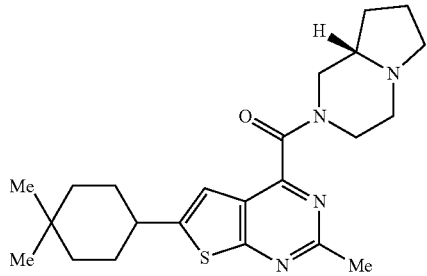 |
| Ex218 | 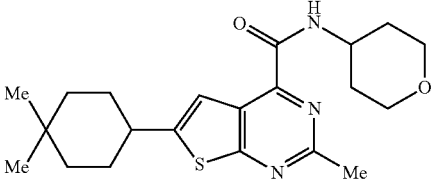 [SMILES: Cc1nc(C(=O)NC2CCOCC2)c2cc(C3CCC(C)(C)CC3)sc2n1] |
TABLE 41
| No./Inf | Str |
|---|---|
| Ex219 | 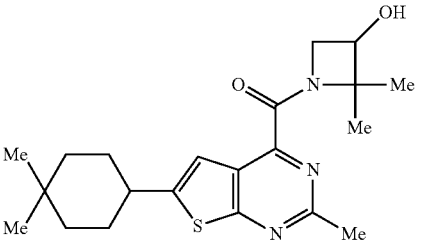 [SMILES: Cc1nc(C(=O)N2CC(O)C2(C)C)c2cc(C3CCC(C)(C)CC3)sc2n1] |
| Ex220 Chiral | 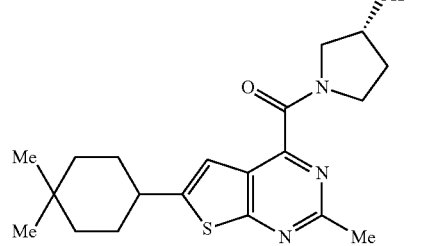 |
| Ex221 Chiral | 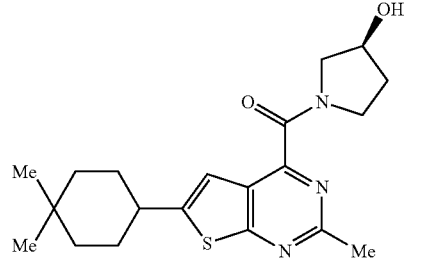 [SMILES: Cc1nc(C(=O)N2CC[C@H](O)C2)c2cc(C3CCC(C)(C)CC3)sc2n1] |
TABLE 41-continued
| No./Inf | Str |
|---|---|
| Ex222 | 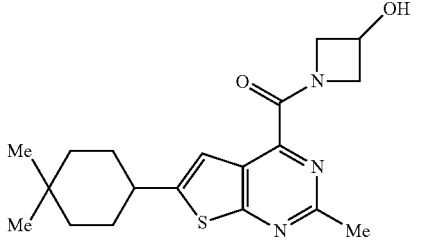 [SMILES: Cc1nc(C(=O)N2CC(O)C2)c2cc(C3CCC(C)(C)CC3)sc2n1] |
| Ex223 | 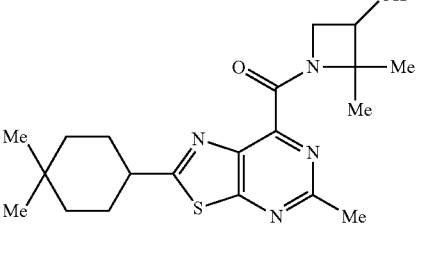 |
| Ex224 | 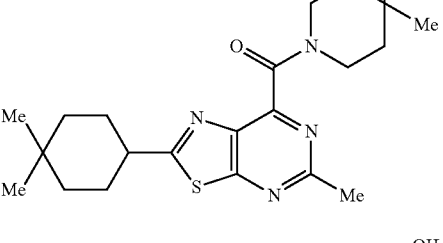 |
| Ex225 | 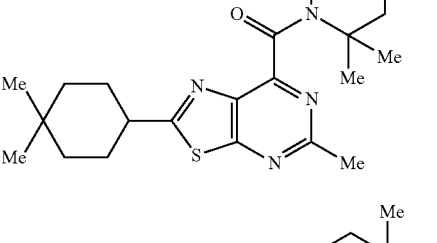 |
| Ex226 | 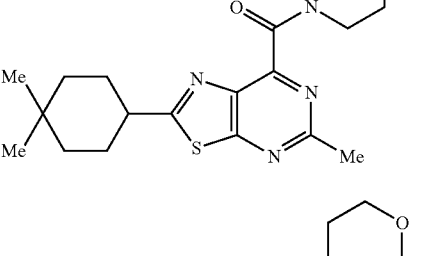 |
| Ex227 | 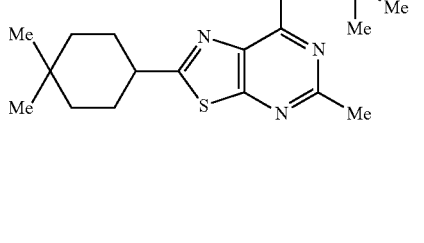 |

TABLE 41-continued

| No./Inf | Str |
|---|---|
| Ex228 Chiral | 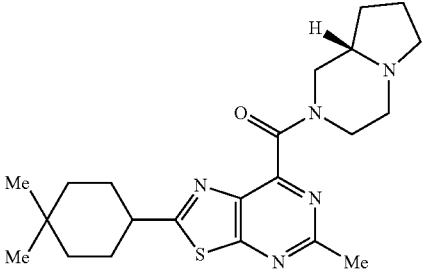 |

TABLE 42

| No./Inf | Str |
|---|---|
| Ex229 | |
| Ex230 | |
| Ex231 | |

TABLE 43

| No. | Ref | Data |
|---|---|---|
| Pr1 | Ex1 | ESI+: 418 |
| Pr1-1 | Ex1 | ESI+: 360 |
| Pr1-2 | Ex1 | ESI+: 360 |
| Pr1-3 | Ex1 | |
| Pr1-4 | Ex1 | ESI+: 358 |
| Pr1-5 | Ex1 | ESI+: 388 |
| Pr1-6 | Ex1 | ESI+: 388 |
| Pr1-7 | Ex1 | ESI+: 372 |
| Pr1-8 | Ex1 | ESI+: 344 |
| Pr1-9 | Ex1 | ESI+: 384 |
| Pr1-10 | Ex1 | ESI+: 386 |
| Pr1-11 | Ex1 | ESI+: 386 |
| Pr1-12 | Ex1 | ESI+: 418 |
| Pr1-13 | Ex1 | ESI+: 388 |
| Pr1-14 | Ex1 | ESI+: 402 |
| Pr1-15 | Ex1 | ESI+: 360 |

TABLE 43-continued

| No. | Ref | Data |
|---|---|---|
| Pr1-16 | Ex1 | ESI+: 361 |

TABLE 44

| No. | Ref | Data |
|---|---|---|
| Pr1-17 | Ex1 | ESI+: 361 |
| Pr1-18 | Ex1 | ESI+: 346 |
| Pr2 | Pr34 | |
| Pr2-1 | Pr34 | ESI+: 487 |
| Pr2-2 | Pr34 | ESI+: 392 |
| Pr2-3 | Pr34 | ESI+: 488 |
| Pr2-4 | Pr34 | ESI+: 472 |
| Pr3 | Pr3 | ESI+: 277 |
| Pr3-1 | Pr3 | ESI+: 285 |
| Pr4 | Pr4 | ESI+: 267 |
| Pr4-1 | Pr4-1 | ESI+: 295 |
| Pr4-2 | Pr4 | ESI+: 263, 265 |
| Pr4-3 | Pr4 | EI: 218, 220 |
| Pr4-4 | Pr4 | ESI+: 303, 305 |
| Pr4-5 | Pr4 | ESI+: 303 |
| Pr4-6 | Pr4-6 | ESI+: 296, 298 |
| Pr4-7 | Pr4 | ESI+: 268, 270 |
| Pr4-8 | Pr4 | ESI+: 320 |
| Pr4-9 | Pr4-6 | ESI+: 336, 338 |
| Pr4-10 | Pr4-6 | ESI+: 282, 284 |
| Pr5 | Pr5 | ESI+: 286 |
| Pr5-1 | Pr5 | ESI+: 294 |
| Pr6 | Pr6 | ESI+: 305 |
| Pr6-1 | Pr6-1 | ESI+: 333 |
| Pr6-2 | Pr6 | ESI+: 301, 303 |
| Pr6-3 | Pr6 | ESI+: 341 |
| Pr6-4 | Pr6 | ESI+: 341 |
| Pr7 | Pr7 | ESI+: 263 |
| Pr7-1 | Pr7-1 | ESI+: 291 |
| Pr7-2 | Pr7 | ESI+: 259, 261 |
| Pr7-3 | Pr7 | ESI+: 299 |
| Pr7-4 | Pr7 | APCI/ESI+: 299 |
| Pr8 | Pr8 | ESI+: 369 |

TABLE 45

| No. | Ref | Data |
|---|---|---|
| Pr8-1 | Pr8 | ESI+: 341 |
| Pr8-2 | Pr8 | |
| Pr8-3 | Pr8 | |
| Pr8-4 | Pr8 | |
| Pr8-5 | Pr8 | ESI+: 377 |
| Pr8-6 | Pr8-7 | ESI+: 356 |
| Pr8-7 | Pr8-7 | ESI+: 370 |
| Pr8-8 | Pr8 | |
| Pr8-9 | Pr8-7 | ESI+: 342 |
| Pr8-10 | Pr8-7 | ESI+: 410 |
| Pr9 | Pr9 | ESI+: 278 |
| Pr9-1 | Pr9 | ESI+: 250 |
| Pr9-2 | Pr9 | ESI+: 302 |
| Pr9-3 | Pr9 | ESI+: 318 |
| Pr9-4 | Pr9 | ESI+: 264 |
| Pr10 | Pr10 | ESI+: 396 |
| Pr10-1 | Pr10 | ESI+: 368 |
| Pr10-2 | Pr10 | ESI+: 420 |
| Pr10-3 | Pr10 | ESI+: 436 |
| Pr10-4 | Pr10 | ESI+: 382 |
| Pr11 | Pr11 | ESI+: 292 |
| Pr11-1 | Pr11 | ESI+: 264 |
| Pr11-2 | Pr11 | ESI+: 278 |
| Pr11-3 | Pr11 | ESI+: 332 |
| Pr12 | Pr12 | ESI+: 249 |
| Pr12-1 | Pr12 | ESI+: 285 |
| Pr13 | Pr13 | ESI+: 281, 283 |
| Pr14 | Pr14 | ESI+: 303 |
| Pr14-1 | Pr14 | ESI+: 331 |

TABLE 45-continued

| No. | Ref | Data |
| --- | --- | --- |
| Pr15 | Pr15 | ESI+: 387 |
| Pr15-1 | Pr15-1 | ESI+: 372 |
| Pr15-2 | Pr15-1 | ESI+: 388 |
| Pr16 | Pr16 | ESI+: 275 |

TABLE 46

| No. | Ref | Data |
| --- | --- | --- |
| Pr16-1 | Pr16 | ESI+: 303 |
| Pr17 | Pr17 | ESI+: 277 |
| Pr17-1 | Pr17 | ESI+: 305 |
| Pr17-2 | Pr17 | ESI+: 305 |
| Pr18 | Pr18 | ESI+: 305 |
| Pr18-1 | Pr18 | ESI+: 316 |
| Pr19 | Pr19 | ESI+: 306 |
| Pr20 | Pr20 | |
| Pr21 | Ex112 | ESI+: 461 |
| Pr22 | Pr22 | ESI+: 259, 261 |
| Pr23 | Pr23 | ESI+: 201, 203 |
| Pr24 | Pr24 | ESI+: 258 |
| Pr24-1 | Pr24 | ESI+: 294 |
| Pr24-2 | Pr24 | ESI+: 254, 256 |
| Pr25 | Pr25 | ESI+: 508 |
| Pr25-1 | Pr25 | APCI/ESI+: 460 |
| Pr25-2 | Pr25 | ESI+: 474 |
| Pr26 | Pr8 + Ex1 | ESI+: 376, 378 |
| Pr26-1 | Pr8 + Ex1 | ESI+: 362 |
| Pr27 | Pr15 | ESI+: 371 |
| Pr28 | Pr28 | ESI+: 404 |
| Pr29 | Ex1 | APCI/ESI+: 344 |
| Pr30 | Ex85 | ESI+: 384 |
| Pr30-1 | Ex85 | ESI+: 388 |
| Pr30-2 | Ex85 | ESI+: 388 |
| Pr31 | Pr31 | ESI+: 372 |
| Pr31-1 | Pr31 | ESI+: 374 |
| Pr31-2 | Pr31 | ESI+: 388 |
| Pr31-3 | Pr31 | ESI+: 394 |
| Pr31-4 | Pr31 | ESI+: 388 |
| Pr32 | Pr32 | ESI+: 416 |
| Pr32-1 | Pr32 | ESI+: 402 |
| Pr32-2 | Pr32 | ESI+: 432 |

TABLE 47

| No. | Ref | Data |
| --- | --- | --- |
| Pr32-3 | Pr32 | ESI+: 432 |
| Pr33 | Pr33 | ESI+: 330 |
| Pr33-1 | Pr33 | ESI+: 358 |
| Pr33-2 | Pr33 | ESI+: 358 |
| Pr34 | Pr34 | ESI+: 344 |
| Pr34-1 | Pr34 | ESI+: 360 |
| Pr34-2 | Pr34 | ESI+: 374 |
| Pr34-3 | Pr34 | ESI+: 380 |
| Pr34-4 | Pr34 | APCI/ESI+: 404 |
| Pr34-5 | Pr34 | ESI+: 358 |
| Pr34-6 | Pr34 | ESI+: 374 |
| Pr34-7 | Pr34 | ESI+: 346 |
| Pr35 | Ex130 | ESI+: 326 |
| Pr36 | Ex198 | ESI+: 394 |
| Pr37 | Pr37 | ESI+: 253 |
| Pr37-1 | Pr37 | ESI+: 261 |
| Pr37-2 | Pr37 | ESI+: 225 |
| Pr38 | Pr38 | ESI+: 295 |
| Pr39 | Pr39 | ESI+: 303 |
| Pr40 | Pr40 | ESI+: 316, 318 |
| Pr40-1 | Pr40 | ESI+: 288, 290 |
| Pr40-2 | Pr40 | ESI+: 356, 358 |
| Pr40-3 | Pr40 | ESI−: 300, 302 |
| Pr41 | Pr41 | ESI+: 340 |
| Pr42 | Pr42 | |
| Pr42-1 | Pr42 | ESI+: 330 |

TABLE 47-continued

| No. | Ref | Data |
| --- | --- | --- |
| Pr43 | Pr43 | CI+: 155 |
| Pr44 | Pr44 | ESI+: 216 |
| Pr45 | Pr45 | ESI+: 222 |
| Pr46 | Pr46 | ESI+: 127 |
| Pr47 | Pr47 | ESI+: 132 |

TABLE 48

| No. | Ref | Data |
| --- | --- | --- |
| Pr48 | Pr48 | ESI+: 254 |
| Pr49 | Pr49 | NMR(CDCl$_3$): 4.20(1H, dd, J = 6.8, 6.8 Hz), 3.64(1H, dd, J = 6.8, 8.9 Hz), 3.31(1H, dd, J = 6.8, 8.9 Hz), 1.30(3H, s), 1.27(3H, s) |
| Pr50 | Pr50 | |
| Pr51 | Pr51 | ESI+: 222 |
| Pr52 | Pr52 | ESI+: 132 |

TABLE 49

| No. | Ref | Data |
| --- | --- | --- |
| Ex1 | Ex1 | ESI+: 380 |
| Ex2 | Ex2 | ESI+: 408 |
| | | NMR(DMSO-d$_6$): 7.56(1H, d, J = 1.1 Hz), 4.03(2H, s, 3.18-3.07(4H, m), 3.04-2.97(4H, m), 2.93-2.85(1H, m), 2.66(3H, s), 1.94-1.86(2H, m), 1.71-1.59(2H, m), 1.53-1.44(2H, m), 1.42-1.30(2H, m), 0.95(6H, s) |
| Ex3 | Ex1 | ESI+: 360 |
| Ex4 | Ex1 | ESI+: 404 |
| Ex5 | Ex1 | ESI+: 390 |
| Ex6 | Ex1 | ESI+: 414 |
| Ex7 | Ex1 | ESI+: 418 |
| Ex8 | Ex1 | ESI+: 420 |
| Ex9 | Ex1 | ESI+: 422 |
| Ex10 | Ex1 | ESI+: 420 |
| Ex11 | Ex1 | ESI+: 360 |
| Ex12 | Ex1 | ESI+: 442 |
| Ex13 | Ex1 | ESI+: 375 |
| Ex14 | Ex1 | ESI+: 389 |
| Ex15 | Ex1 | ESI+: 403 |
| Ex16 | Ex1 | ESI+: 389 |
| Ex17 | Ex1 | ESI+: 389 |
| Ex18 | Ex1 | ESI+: 401 |

TABLE 50

| No. | Ref | Data |
| --- | --- | --- |
| Ex19 | Ex1 | ESI+: 391 |
| Ex20 | Ex1 | ESI+: 405 |
| | | NMR(DMSO-d6): 4.45(1H, d, J = 4.0 Hz), 4.15(1H, s), 4.00(2H, s), 3.21-3.15(1H, m), 3.13-3.05(1H, m), 2.71(3H, s), 2.70-2.64(1H, m), 2.55(1H, d, J = 10.2 Hz), 2.30-2.21(1H, m), 2.07(1H, d, J = 10.9 Hz), 2.03-1.94(2H, m), 1.83-1.65(3H, m), 1.53-1.28(5H, m), 1.02(3H, s), 0.96(3H, s), 0.94(3H, s) |
| Ex21 | Ex1 | ESI+: 433 |
| Ex22 | Ex1 | ESI+: 415 |
| Ex23 | Ex1 | ESI+: 375 |
| Ex24 | Ex1 | ESI+: 403 |
| Ex25 | Ex1 | ESI+: 421 |
| Ex26 | Ex1 | ESI+: 395 |
| Ex27 | Ex1 | ESI+: 429 |
| Ex28 | Ex1 | ESI+: 361 |
| Ex29 | Ex1 | ESI+: 333 |
| Ex30 | Ex1 | ESI+: 443 |
| Ex31 | Ex31 | ESI+: 390 |
| | | NMR(DMSO-d$_6$): 7.56(1H, d, J = 1.1 Hz), 4.67(2H, t, J = 4.4 Hz), 3.85(1H, d, J = 14.0 Hz), 3.78(1H, d, |

TABLE 50-continued

| No. | Ref | Data |
|---|---|---|
| | | J = 14.0 Hz), 3.25-3.08(2H, m), 2.91-2.75(2H, m), 2.74-2.67(1H, m), 2.65(3H, s), 2.07(1H, td, J = 11.6, 2.4 Hz), 1.95-1.85(3H, m), 1.77-1.58(3H, m), 1.51-1.44(2H, m), 1.41-1.31(3H, m), 0.95(3H, s), 0.94(3H, s) |
| Ex31-1 | Ex31 | ESI+: 390 |
| Ex32 | Ex31 | ESI+: 391 |
| | | NMR(CDCl$_3$): 4.19(1H, d, J = 14.0 Hz), 4.15(1H, d, J = 14.0 Hz), 3.68-3.60(1H, m), 3.56-3.48(1H, m), 3.15-3.08(1H, m), 3.04-2.92(2H, m), 2.83(3H, s), 2.62(1H, brs), 2.47-2.36(1H, m), 2.36-2.28(1H, m), 2.07-1.97(3H, m), 1.89(1H, brs), 1.88-1.75(2H, m), 1.74-1.62(1H, m), 1.6-1.5(2H, m), 1.43-1.32(2H, m), 0.99(6H, s) |
| Ex32-1 | Ex31 | ESI+: 391 |
| Ex33 | Ex33 | ESI+: 360 |
| Ex34 | Ex33 | ESI+: 360 |

TABLE 51

| No. | Ref | Data |
|---|---|---|
| Ex35 | Ex33 | ESI+: 346 |
| Ex36 | Ex33 | ESI+: 346 |
| Ex37 | Ex33 | ESI+: 358 |
| Ex38 | Ex33 | ESI+: 358 |
| Ex39 | Ex33 | ESI+: 388 |
| Ex40 | Ex33 | ESI+: 388 |
| Ex41 | Ex33 | ESI+: 372 |
| Ex42 | Ex33 | ESI+: 344 |
| Ex43 | Ex33 | ESI+: 384 |
| Ex44 | Ex33 | ESI+: 386 |
| Ex45 | Ex33 | ESI+: 386 |
| Ex46 | Ex33 | ESI+: 418 |
| Ex47 | Ex33 | ESI+: 388 |
| | | NMR(DMSO-d$_6$): 10.1(1H, brs), 7.55(1H, d, J = 1.1 Hz), 4.83(2H, brs), 4.08-3.58(2H, m), 3.46-3.20(3H, m), 2.93-2.82(1H, m), 2.76(3H, s), 1.96-1.82(4H, m), 1.73-1.61(4H, m), 1.53-1.45(2H, m), 1.43-1.33(2H, m), 1.30-1.16(3H, m), 0.96(3H, s), 0.95(3H, s) |
| Ex48 | Ex33 | ESI+: 402 |
| Ex49 | Ex33 | ESI+: 360 |
| Ex50 | Ex33 | ESI+: 418 |
| Ex51 | Ex33 | ESI+: 392 |
| Ex52 | Ex52 | ESI+: 374 |
| | | NMR(DMSO-d$_6$): 10.41(1H, brs), 7.57(1H, s), 5.25-4.95(1H, brs), 4.80(2H, brs), 4.04-3.04(5H, m), 2.94-2.80(1H, m), 2.76(3H, s), 2.08-1.87(4H, m), 1.82-1.60(4H, m), 1.54-1.44(2H, m), 1.44-1.31(2H, m), 0.96(3H, s), 0.95(3H, s) |
| Ex53 | Ex52 | ESI+: 330 |
| Ex54 | Ex52 | ESI+: 390 |
| Ex55 | Ex198 | ESI+: 394 |
| Ex56 | Ex198 | ESI+: 356 |
| Ex57 | Ex52 | ESI+: 346 |
| Ex58 | Ex52 | ESI+: 366 |
| Ex59 | Ex52 | ESI+: 330 |
| Ex60 | Ex52 | ESI+: 330 |
| Ex61 | Ex52 | ESI+: 408 |
| Ex62 | Ex52 | ESI+: 360 |

TABLE 52

| No. | Ref | Data |
|---|---|---|
| Ex63 | Ex52 | ESI+: 402 |
| Ex64 | Ex52 | ESI+: 332 |
| | | NMR(DMSO-d$_6$): 11.19(1H, brs), 7.54(1H, d, J = 1.1 Hz), 4.85(2H, brs), 3.91(4H, brs), 3.64-3.25(4H, brs), 3.01-2.89(1H, m), 2.75(3H, s), 2.12-2.03(2H, m), 1.86-1.76(2H, m), 1.76-1.67(1H, m), 1.55-1.35(4H, m), 1.32-1.20(1H, m) |
| Ex65 | Ex52 | ESI+: 359 |
| Ex66 | Ex52 | ESI+: 364 |
| Ex67 | Ex52 | ESI+: 365 |

TABLE 52-continued

| No. | Ref | Data |
|---|---|---|
| Ex68 | Ex52 | ESI+: 378 |
| Ex69 | Ex52 | ESI+: 379 |
| Ex70 | Ex52 | ESI+: 368 |
| Ex71 | Ex52 | ESI+: 368 |
| Ex72 | Ex52 | ESI+: 374 |
| Ex73 | Ex52 | ESI+: 374 |
| Ex74 | Ex52 | ESI+: 376 |
| Ex75 | Ex52 | ESI+: 356 |
| Ex76 | Ex52 | ESI+: 392 |
| Ex77 | Ex52 | ESI+: 384 |
| Ex78 | Ex52 | ESI+: 360 |
| Ex79 | Ex52 | ESI+: 388 |
| Ex80 | Ex52 | ESI+: 422 |
| Ex81 | Ex52 | ESI+: 346 |
| Ex82 | Ex52 | ESI+: 396 |
| Ex83 | Ex52 | ESI+: 396 |
| Ex84 | Ex52 | ESI+: 405 |
| Ex85 | Ex85 | ESI+: 376 |
| Ex86 | Pr8 + Ex85 | ESI+: 371 |
| Ex87 | Ex85 | ESI+: 409 |
| Ex88 | Ex85 | ESI+: 419 |
| Ex89 | Ex85 | ESI+: 391 |
| Ex90 | Ex85 | ESI+: 391 |
| Ex91 | Ex85 | ESI+: 405 |
| Ex92 | Ex85 | ESI+: 445 |
| Ex93 | Ex85 | ESI+: 377 |

TABLE 53

| No. | Ref | Data |
|---|---|---|
| Ex94 | Ex85 | ESI+: 431 |
| Ex95 | Ex85 | ESI+: 395 |
| Ex96 | Ex96 | ESI+: 388 |
| Ex97 | Pr8 + Ex96 | ESI+: 396 |
| Ex98 | Ex96 | ESI+: 366 |
| Ex99 | Pr8 + Ex96 | ESI+: 396 |
| Ex100 | Ex96 | ESI+: 422 |
| Ex101 | Ex96 | ESI+: 390 |
| Ex102 | Ex96 | ESI+: 390 |
| Ex103 | Ex96 | ESI+: 372 |
| Ex104 | Ex96 | ESI+: 404 |
| Ex105 | Ex105 | ESI+: 385 |
| Ex106 | Ex106 | ESI+: 346 |
| Ex107 | Ex107 | ESI+: 385 |
| Ex108 | Ex108 | ESI+: 406 |
| Ex109 | Ex109 | ESI+: 376 |
| Ex110 | Ex109 | ESI+: 376 |
| Ex111 | Ex109 | ESI+: 360 |
| Ex112 | Ex112 | APCI/ESI+: 344 |
| Ex113 | Ex112 | ESI+: 346 |
| Ex114 | Ex112 | APCI/ESI+: 330 |
| Ex115 | Ex112 | ESI+: 370 |
| Ex116 | Ex116 | ESI+: 348 |
| Ex117 | Ex116 | ESI+: 346 |
| Ex118 | Ex116 | ESI+: 374 |
| Ex119 | Ex116 | ESI+: 374 |
| Ex120 | Ex116 | ESI+: 388 |
| Ex121 | Ex116 | ESI+: 372 |
| Ex122 | Ex116 | ESI+: 373 |
| Ex123 | Ex116 | ESI+: 389 |
| Ex124 | Ex116 | ESI+: 415 |
| Ex125 | Ex116 | ESI+: 376 |
| Ex126 | Ex126 | ESI+: 372 |
| Ex127 | Ex126 | ESI+: 404 |
| Ex128 | Ex126 | ESI+: 391 |

TABLE 54

| No. | Ref | Data |
|---|---|---|
| Ex129 | Pr33 | ESI+: 358 |
| Ex130 | Ex130 | ESI+: 344 |

TABLE 54-continued

| No. | Ref | Data |
|---|---|---|
| Ex131 | Ex130 | ESI+: 376 |
| Ex132 | Ex130 | ESI+: 360 |
| Ex133 | Ex130 | ESI+: 360 |
| Ex134 | Ex134 | ESI+: 346 |
| Ex135 | Ex134 | ESI+: 346 |
| Ex136 | Ex134 | ESI+: 360 |
| Ex137 | Ex134 | ESI+: 360 |
| Ex138 | Ex134 | ESI+: 332 |
| Ex139 | Ex134 | ESI+: 332 |
| Ex140 | Pr8 + Pr34 | ESI+: 362 |
| Ex141 | Pr8 + Pr34 | ESI+: 362 |
| Ex142 | Pr34 | ESI+: 402 |
| Ex143 | Pr34 | ESI+: 392 |
| Ex144 | Pr34 | ESI+: 392 |
| Ex145 | Pr34 | ESI+: 393 |
| Ex146 | Ex198 | ESI+: 402 |
| Ex147 | Ex198 | ESI+: 400 |
| Ex148 | Ex198 | ESI+: 348 |
| Ex149 | Ex198 | ESI+: 355 |
| Ex150 | Ex150 | ESI+: 374 |
| Ex151 | Ex150 | ESI+: 401 |
| Ex152 | Ex152 | ESI+: 360 |
| Ex153 | Ex153 | ESI+: 429 |
| Ex154 | Ex153 | ESI+: 413 |
| Ex155 | Ex155 | ESI+: 445 |
| Ex156 | Ex155 | ESI+: 429 |
| Ex157 | Ex155 | ESI+: 438 |
| Ex158 | Ex155 | ESI+: 446 |
| Ex159 | Ex155 | ESI+: 430 |
| Ex160 | Ex155 | ESI+: 455 |
| Ex161 | Ex161 | ESI+: 361 |
| Ex162 | Ex161 | ESI+: 361 |
| Ex163 | Ex163 | ESI+: 371 |
| Ex164 | Pr13 + Ex52 | ESI+: 384 |

TABLE 55

| No. | Ref | Data |
|---|---|---|
| Ex165 | Pr13 + Ex52 | ESI+: 402 |
| Ex166 | Pr13 + Ex52 | ESI+: 368 |
| Ex167 | Pr13 + Ex52 | ESI+: 402 |
| Ex168 | Ex1 | ESI+: 388 |
| Ex169 | Ex1 | ESI+: 414 |
| Ex170 | Ex1 | ESI+: 332 |
| Ex171 | Ex33 | ESI+: 358 |
| Ex172 | Ex33 | ESI+: 372 |
| Ex173 | Ex33 | ESI+: 394 |
| Ex174 | Ex33 | ESI+: 388 |
| Ex175 | Ex33 | ESI+: 374 |
| Ex176 | Ex33 | ESI+: 416 |
| Ex177 | Ex33 | ESI+: 402 |
| Ex178 | Ex33 | ESI+: 432 |
| Ex179 | Ex33 | ESI+: 360 |
| Ex180 | Ex33 | ESI+: 388 |
| Ex181 | Ex33 | ESI+: 432 |
| Ex182 | Ex33 | ESI+: 344 |
| Ex183 | Ex52 | ESI+: 318 |
| Ex184 | Ex130 | ESI+: 378 |
| Ex185 | Ex52 | ESI+: 346 |
| Ex186 | Pr8 + Ex85 | ESI+: 334 |
| Ex187 | Ex187 | APCI/ESI+: 386 |
| Ex188 | Ex188 | ESI+: 416 |
| Ex189 | Ex190 | ESI+: 348 |
| Ex190 | Ex190 | ESI+: 398 |
| Ex191 | Ex191 | ESI+: 436 |
| Ex192 | Ex191 | ESI+: 408 |
| Ex193 | Ex191 | ESI+: 450 |
| Ex194 | Ex191 | ESI+: 466 |
| Ex195 | Ex191 | ESI+: 360 |
| Ex196 | Ex196 | ESI+: 418 |
| Ex197 | Ex130 | ESI+: 290 |
| Ex198 | Ex198 | ESI+: 422 |
| Ex199 | Ex198 | ESI+: 422 |
| Ex200 | Ex198 | ESI+: 422 |

TABLE 56

| No. | Ref | Data |
|---|---|---|
| Ex201 | Pr7-1 | ESI+: 291 |
| Ex202 | Ex187 | ESI+: 332 |
| Ex203 | Ex187 | ESI+: 398 |
| Ex204 | Ex187 | ESI+: 362 |
| Ex205 | Ex205 | ESI+: 436 |
| Ex206 | Ex206 | ESI+: 402 |
| Ex207 | Ex206 | ESI+: 414 |
| Ex208 | Ex206 | ESI+: 374 |
| Ex209 | Ex206 | ESI+: 372 |
| Ex210 | Ex206 | ESI+: 387<br>NMR(DMSO-$d_6$): 7.11(1H, d, 1.1 Hz), 3.74-3.67(2H, m), 3.29-3.24(2H, m), 2.94-2.84(1H, m), 2.70(3H, s), 2.46-2.40(2H, m), 2.27-2.22(2H, m), 2.20(3H, s), 1.92-1.84(2H, m), 1.71-1.58(2H, m), 1.51-1.43(2H, m), 1.40-1.29(2H, m), 0.94(6H, s) |
| Ex211 | Ex206 | ESI+: 388 |
| Ex212 | Ex206 | ESI+: 404 |
| Ex213 | Ex206 | ESI+: 401 |
| Ex214 | Ex206 | ESI+: 415 |
| Ex215 | Ex206 | ESI+: 413 |
| Ex216 | Ex206 | ESI+: 428 |
| Ex217 | Ex206 | ESI+: 413 |
| Ex218 | Ex206 | ESI+: 388 |
| Ex219 | Ex206 | ESI+: 388 |
| Ex220 | Ex206 | ESI+: 374 |
| Ex221 | Ex206 | ESI+: 374 |
| Ex222 | Ex206 | ESI+: 360 |
| Ex223 | Ex206 | ESI+: 389 |
| Ex224 | Ex206 | ESI+: 403 |
| Ex225 | Ex206 | ESI+: 417 |
| Ex226 | Ex206 | ESI+: 401 |
| Ex227 | Ex206 | ESI+: 403 |
| Ex228 | Ex206 | ESI+: 414 |
| Ex229 | Ex229 | ESI+: 436 |
| Ex230 | Ex229 | ESI+: 388 |
| Ex231 | Ex229 | ESI+: 402 |

INDUSTRIAL APPLICABILITY

The compound of the present invention is a PAM of a $GABA_B$ receptor, and can be used as an agent for preventing and/or treating schizophrenia, cognitive impairment, fragile X syndrome, autism spectrum disorder, spasticity, anxiety disorder, substance addiction, pain, fibromyalgia, Charcot-Marie-Tooth disease, or the like.

Furthermore, based on the knowledge obtained by the present invention, the PAM of the $GABA_B$ receptor can be used as a drug for preventing and/or treating schizophrenia, cognitive impairment, fragile X syndrome, autism spectrum disorder, spasticity, anxiety disorder, substance addiction, pain, fibromyalgia, Charcot-Marie-Tooth disease, or the like.

The invention claimed is:
1. A compound of the formula (I) or a salt thereof:

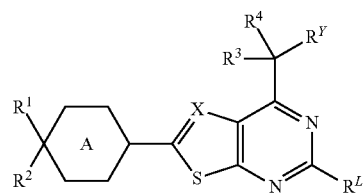

wherein
X is CH,
$R^1$ is lower alkyl,
$R^2$ is lower alkyl, in which $R^1$ and $R^2$ may form a cycloalkane together with carbon atoms to which they are bonded,
$R^3$ is —H,
$R^4$ is —H,
A ring is a cyclohexane ring,
$R^Y$ is —$NR^AR^B$,
$R^A$ and $R^B$ form cyclic amino which may be substituted, together with a nitrogen atom to which they are bonded,
in which the cyclic amino is a group represented by formula (III):

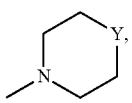

(III)

Y is NH, O, S, S(=O)$_2$, or CH$_2$, and
$R^L$ is lower alkyl.

2. The compound or a salt thereof according to claim 1, wherein
$R^Y$ is —$NR^AR^B$,
$R^A$ and $R^B$ form cyclic amino which may be substituted with $R^0$, together with a nitrogen atom to which they are bonded,
in which the cyclic amino is a group represented by the following formula (III):

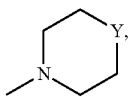

(III)

and
$R^0$ is a group selected from the following Group Z:
Group Z:
(1) =O,
(2) —OH,
(3) —O-lower alkyl,
(4) halogen,
(5) —CN,
(6) lower alkyl,
(7) halo-lower alkyl,
(8) lower alkylene-OH,
(9) lower alkylene-O-lower alkyl,
(10) —C(=O)-lower alkyl,
(11) —C(=O)-lower alkylene-OH,
(12) —C(=O)-lower alkylene-CN, and
(13) cycloalkyl.

3. The compound or a salt thereof according to claim 2, wherein the group selected from the Group Z is a group selected from:
Group Z1:
(1) —OH,
(2) lower alkyl, and
(3) —C(=O)-lower alkylene-OH.

4. The compound or a salt thereof according to claim 3, wherein Y is O, S, or S(=O)$_2$.

5. The compound or a salt thereof according to claim 4, wherein $R^L$ is CH$_3$.

6. The compound or a salt thereof according to claim 1, which is selected from the following compound group:
6-(4,4-dimethylcyclohexyl)-4-[(1,1-dioxo-1λ$^6$-thiomorpholin-4-yl)methyl]-2-methylthieno[2,3-d]pyrimidine,
trans-1-{[6-(4,4-dimethylcyclohexyl)-2-methylthieno[2,3-d]pyrimidin-4-yl]methyl}piperidine-3,4-diol,
1-{[6-(4,4-dimethylcyclohexyl)-2-methylthieno[2,3-d]pyrimidin-4-yl]methyl}piperidin-4-ol,
6-(4,4-dimethylcyclohexyl)-2-methyl-4-(thiomorpholin-4-ylmethyl)thieno[2,3-d]pyrimidine,
6-(4,4-dimethylcyclohexyl)-4-[(3,3-dimethylmorpholin-4-yl)methyl]-2-methylthieno[2,3-d]pyrimidine, and
1-{[6-(4,4-dimethylcyclohexyl)-2-methylthieno[2,3-d]pyrimidin-4-yl]methyl}-2,2-dimethylpiperidin-4-ol, or a salt thereof.

7. The compound or a salt thereof according to claim 6, which is 6-(4,4-dimethylcyclohexyl)-4-[(1,1-dioxo-1λ$^6$-thiomorpholin-4-yl)methyl]-2-methylthieno[2,3-d]pyrimidine, or a salt thereof.

8. The compound or a salt thereof according to claim 6, which is trans-1-{[6-(4,4-dimethylcyclohexyl)-2-methylthieno[2,3-d]pyrimidin-4-yl]methyl}piperidine-3,4-diol, or a salt thereof.

9. The compound or a salt thereof according to claim 6, which is 1-{[6-(4,4-dimethylcyclohexyl)-2-methylthieno[2,3-d]pyrimidin-4-yl]methyl}piperidin-4-ol, or a salt thereof.

10. The compound or a salt thereof according to claim 6, which is 6-(4,4-dimethylcyclohexyl)-2-methyl-4-(thiomorpholin-4-ylmethyl)thieno[2,3-d]pyrimidine, or a salt thereof.

11. The compound or a salt thereof according to claim 6, which is 6-(4,4-dimethylcyclohexyl)-4-[(3,3-dimethylmorpholin-4-yl)methyl]-2-methylthieno[2,3-d]pyrimidine, or a salt thereof.

12. The compound or a salt thereof according to claim 6, which is 1-{[6-(4,4-dimethylcyclohexyl)-2-methylthieno[2,3-d]pyrimidin-4-yl]methyl}-2,2-dimethylpiperidin-4-ol, or a salt thereof.

13. A pharmaceutical composition comprising the compound or a salt thereof according to claim 1 and a pharmaceutically acceptable excipient.

14. The pharmaceutical composition according to claim 13, which is a GABA$_B$ receptor positive allosteric modulator.

* * * * *